US006787300B2

(12) United States Patent
Guarente et al.

(10) Patent No.: US 6,787,300 B2
(45) Date of Patent: Sep. 7, 2004

(54) IDENTIFYING LIFESPAN-ALTERING AGENTS

(75) Inventors: Leonard P. Guarente, Chestnut Hill, MA (US); Nicanor Austriaco, Jr., Somerville, MA (US); Brian Kennedy, Arlington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 25 days.

(21) Appl. No.: 09/826,752

(22) Filed: Apr. 5, 2001

(65) Prior Publication Data

US 2001/0026930 A1 Oct. 4, 2001

Related U.S. Application Data

(60) Division of application No. 09/323,433, filed on Jun. 1, 1999, now Pat. No. 6,218,512, which is a division of application No. 08/396,001, filed on Feb. 28, 1995, now Pat. No. 5,919,618, which is a continuation-in-part of application No. PCT/US94/09351, filed on Aug. 15, 1994, which is a continuation-in-part of application No. 08/107,408, filed on Aug. 16, 1993, now abandoned.

(51) Int. Cl.$^7$ .................................................. C12Q 1/02

(52) U.S. Cl. ........................................ 435/4; 435/7.31

(58) Field of Search ...................... 435/4, 7.31, 254.11, 435/254.2

(56) References Cited

U.S. PATENT DOCUMENTS

| | | |
|---|---|---|
| 5,565,323 A | 10/1996 | Parker et al. |
| 5,705,350 A | 1/1998 | Mudryj et al. |
| 5,744,300 A | 4/1998 | Linskens et al. |
| 5,817,782 A | 10/1998 | Jazwinski |
| 5,840,493 A | 11/1998 | Davis et al. |
| 5,874,210 A | 2/1999 | Guarente et al. |
| 5,919,618 A | 7/1999 | Guarente et al. |
| 5,965,543 A | 10/1999 | Campisi et al. |
| 6,027,883 A | 2/2000 | Herrnstadt et al. |
| 6,146,831 A | 11/2000 | Davis et al. |
| 6,218,512 B1 | 4/2001 | Guarente et al. |
| 6,228,583 B1 | 5/2001 | Guarente et al. |
| 6,291,172 B1 | 9/2001 | Davis et al. |

FOREIGN PATENT DOCUMENTS

WO    WO 96/05850    2/1996

OTHER PUBLICATIONS

Fleming et al. Role of oxidative stress in Drosophila aging. Mutation Research vol. 275, pp. 267–279 (1992).*
Hirsch, "Accumulation of a Senescence Factor in Yeast Cells", *Experimental Gerontology*, 28(2):195–204 (1993).
Jazwinski, et al., "Replication Control and Differential Gene Expression in Aging Yeast," *Molecular Biology of Aging*, pp. 189–203 (1990).

Jazwinski, "Aging and senescence of the Budding Yeast *Saccharomyces cerevisiae*," *Molecular Microbiology*, 4(3):337–343 (1990).
Egilmez and Jazwinski, "Evidence for the Involvement of a Cytoplasmic Factor in the Aging of the Yeast *Saccharomyces cerevisiae*," *Journal of Bacteriology*, 171 (1):37–42 (1989).
Sainsard–Chanet and Begel, "Transformation of Yeast and *Podospora*: Innocuity of Senescence–Specific DNAs," *Mol Gen Genet*, 204:443–451 (1986).
Miura and Sato, "Cellular Senescence in Yeast Caused by Carbon–Source Starvation;" *J. Biochem.*, 76: 593–601 (1974).
Miura and Yanagita, "Cellular Senescence in Yeast Caused by Carbon–Source Starvation," *J. Biochem.*, 72(1): 141–148 (1972).
Longtine, et al., "Telomere–Mediated Plasmid Segregation in *Saccharomyces cerevisiae* Involves Gene Products Required for Transcriptional Repression at Silencers and Telomeres," *Genetics*, 133:171–182 (1993).
Lee and Gross, "Conditional Silencing: The *HMRE* Mating–Type Silencer Exerts a Rapidly Reversible Position Effect on the Yeast *HSP82* Heat Shock Gene," *Molecular and Cellular Biology*, 13(2): 727–738 (1993).
Sussel and Shore, "Separation of Transcriptional Activation and Silencing Functions of the *RAP1*–Encoded Repressor/Activator Protein 1: Isolation of Viable Mutants Affecting Both Silencing and Telomere Length," *Proc. Natl. Acad. Sci. USA*, 88: 7749–7753 (Sep. 1991).
Schnell, et al., "Genetic and Molecular Characterization of Suppressors of *SIR4* Mutations in *Saccharomyces cerevisiae*," *Genetics* 122:29–46 (May 1989).
Marshall, et al., "Functional Domains of SIR4, a Gene Required for Position Effect Regulation in *Saccharomyces cerevisiae*," *Molecular and Cellular Biology*, 7(12): 4441–4452 (1987).
Ivy, et al., "Map Positions of Yeast Genes *SIR1, SIR3* and *SIR4*," *Genetics III*: 735–744 (1985).
Aparicio, et al., "Modifiers of Position Effect are Shared Between Telomeric and Silent Mating–Type Loci in *S. cerevisiae*," *Cell*, 66:1279–1287 (1991).
Lundblad and Szostak, "A Mutant with Cell Defect in Telomere Elongation Leads to Senescence in Yeast," 57: 633–643 (1989).
Jazwinski, "Genes of Youth: Genetics of Aging in Baker's Yeast," *ASM News*, 59(4): 172–178 (1993).

(List continued on next page.)

Primary Examiner—John S. Brusca
(74) Attorney, Agent, or Firm—Fish & Richardson P.C.

(57) ABSTRACT

Methods of isolating mutant yeast cells with increased life span, as well as mutant yeast cells isolated by the methods, are disclosed. Also described are methods of identifying agents which increase life span of yeast cells, and methods of isolating genes which affect senescence in organisms.

48 Claims, 63 Drawing Sheets

OTHER PUBLICATIONS

D'Mello, et al., "Molecular Analysis of a Young–Specific Gene in the Yeast *Saccharomyces cerevisiae,*" *Abstracts of the 92nd General Meeting of the American Society for Microbiology*, Abstract H–284, p. 230 (May 26–30, 1992).

Egilmez, et al., "Specific Alterations in Transcript Prevalence During the Yeast Life Span," *The Journal of Biological Chemistry*, 264(24): 14312–14317 (1989).

Jazwinski, et al., "Replication Control and Differential Gene Expression in Aging Yeast," *Molecular Biology of Aging*, pp. 189–203 (1989).

Muller, et al., "Calendar Life Span Versus Budding Life Span of *Saccharomyces cerevisiae,*" Mechanisms of Ageing and Development, 12(1): 47–52 (1980).

Urrestarazu and Jauniaux, Protein Sequence Database, Accession No. S38114 (1994).

Allsopp et al., "Telomere length predicts replicative capacity of human fibroblasts", *Proc. Natl. Acad. Sci. USA* 89:10114–10118 (1992).

Angello et al., "Cell Enlargement: One Possible Mechanism Underlying Cellular Senescence", *J. Cell. Physiol.* 140:288–294 (1989).

Angello et al., "Proliferative Potential of Human Fibroblasts: An Inversive Dependence on Cell Size", *J. Cell. Physiol.* 132:125–130 (1987).

Bertrand et al., "An Extrachromosomal Plasmid Is the Etiological Precursor of kaIDNA Insertion Sequences in the Mitochrondial Chromosome of Senescent Neurospora", *Cell* 47:829–837 (1986).

Cabib et al., "A Molecular Model for Morphogenesis: The Primary Septum of Yeast", *Curr. Top. Cell. Regul.* 8:1–32 (1974).

Cristofalo and Kritchevsky, "Cell Size and Nucleic Acid Content in the Diploid Human Cell Line WI–38 During Aging", *Med. Exp.* 19:313–320 (1969).

Cristofalo et al., "Growth factors as probes of cell aging", *Exp. Gerontol.* :367–374 (1989).

Cummings et al., "Excision—Amplification of Mitochrondial DNA During Senescence in *Podospora anserina*", *J. Mol. Biol.* 185:659–680 (1985).

Cziepluch et al., "Sequencing analysis of a 40.2 kb fragment of yeast chromosome X reveals 19 open reading frames including *URA2* (5' end), *TRK1, PBS2, SPT10, GCD14, RPE1, PHO86, NCA3, ASF1, CCT7, GZF3,* two tRNA genes, three remnant delta elements and a Ty4 transposon", *Yeast* 12:1471–1474 (1996).

Egilmez et al., "Preparation and Partial Characterization of Old Yeast Cells", *J. Gerontol. Biol. Sci.* 45:B9–17 (1990).

Friedman and Johnson, "A Mutation in the *age–1* Gene in *Caenorhabditis elegans* Lengthens Life and Reduces Hermaphrodite Fertility", *Genetics* 118:75–86 (1988).

Guarente, "UASs and Enhancers: Common Mechanism of Transcriptional Activation in Yeast and Mammals", *Cell* 52:303–305 (1988).

Guarente and Kenyon, "Genetic pathways that regulate ageing in model organisms", *Nature* 408:255–262 (2000).

Harley et al., "Telomeres shorten during ageing of human fibroblasts", *Nature* 345:458–460 (1990).

Hayflick, "The limited in vitro lifetime of human diploid cell strains", *Exp. Cell Res.* 37:614–636 (1965).

Hayflick and Moorhead, "The serial cultivation of human diploid cell strains", *Exp. Cell Res.* 25:585–621 (1961).

Jazwinski, "Longevity, Genes, and Aging", *Science* 273:54–59 (1996).

Kenyon et al., "A *C. elegans* mutant that lives twice as long as wild type", *Nature* 366:461–464 (1993).

Koll et al., "A 1100–bp Sequence of Mitochondiral DNA Is Involved in Senescence Process in *Podospora*: Study of Senescent and Mutant Cultures", *Plasmid* 14:106–117 (1985).

Lazarus et al., "Amplification of a Mitochondrial DNA Sequence in the Cytoplasmically Inherited 'Ragged' Mutant of *Aspergillus amstelodami*", *Eur. J. Biochem* 106:663–641 (1980).

Lumpkin Jr., et al., "Existence of High Abundance Antiproliferative mRNA's in Senescent Human Diploid Fibroblasts", *Science* 232:393–395 (1986).

McConnell et al., "Temperate–sensitive Yeast Mutants Defective in Mitochondrial Inheritance", *J. Cell Biol.* 111:967–976 (1990).

Mortimer and Johnston, "Life Span of Individual Yeast Cells", *Nature* 183:1751–1752 (1959).

Müller, "Experiments on Ageing in Single Cells of *Saccharomyces cerevisiae*", *Arch. Mikrobiol.* 77:20–25 (1971).

Müller, "Parental age and the life–span of zygotes of *Saccharomyces cerevisiae*", *Antonie van Leeuwenhoek* 51:1–10 (1985).

Müller and Wolf, "A Correlation Between Shortened Life Span and UV–Sensitivity in Some Strain of *Saccharomyces cerevisiae*", *Mol. Gen. Genet.* 160:231–234 (1978).

Norwood et al., "Dominance of the Senescent Phenotype in Heterokaryons Between Replicative and Post–Replicative Human Fibroblast–Like Cells", *Proc. Natl. Acad. Sci. USA* 71:2231–2235 (1974).

Olovnikov, "A Theory of Marginotomy: The Incomplete Copying of Template Margin in Enzymic Synthesis of Polynucleotides and Biological Significance of the Phenomenon", *J. Theor. Biol.* 41:181–190 (1973).

Orgel, "Ageing of Clones of Mammalian Cells", *Nature* 243:441–445 (1973).

Palladino et al., "SIR3 and SIR4 Proteins Are Required for the Positioning and Integrity of Yeast Telomeres", *Cell* 75:543–555 (1993).

Pélissier et al., "*NCA3,* a nuclear gene involved in the mitochondrial expression of subunits 6 and 8 of the Fo–F1 ATP synthase of *S. cerevisiae*", *Curr. Genet.* 27:409–416 (1995).

Pereira–Smith and Smith, "Genetic analysis of indefinite division in human cells: Identification of four complementation groups", *Proc. Natl. Acad. Sci. USA* 85:604–60462 (1988).

Pohley, "A formal mortality analysis for populations of unicellular organisms (*Saccharomyces cerevisiae*)", *Mechanisms of Ageing and Development* 38:231–243 (1987).

Pringle et al., "Fluorescence Microscopy Methods for Yeast", *Methods in Cell Biology* 31:357–435 (1989).

* cited by examiner

```
1/1
AAG CTT TAA CGG GAT CTT CTA ACA ACA AAT ATA ACC AAA AAC CAG CTT CAG TGG
 K   L   *   R   D   L   L   T   T   N   I   T   K   N   Q   L   Q   W
 S   F   N   G   I   S   F   Q   Q   K   *   P   K   T   S   F   S   G
 A       T           R   A       N           31/11                  V
                                             AGC ATA
                                              S   I
                                              A   *
                                              H   N
61/21
GAT CAG CCT ATC GAC ACG CCT TTT TTA ACA CAA GTC TAA GCG TTT ATG TCG TAT GGA
 D   Q   P   I   D   T   P   F   L   T   Q   V   *   A   F   M   S   Y   G
 I   S   L   Y   R   H   A   F   F   L   N   C   L   R   L   C   V   V   W
     A       T           R       S       T   V   *   A       Y       R   M
121/41
ATT TCT ATA CTT GAC CCT ACC TTA TAT GCC TAT AAG GAT TTT CTC GAA AGA AAA
 I   S   I   L   D   P   T   L   Y   A   Y   K   D   F   L   E   R   K
 L   F   Y   L   *   P   Y   I   *   P   I   R   I   F   S   K   E   K
 Y   L   *   T   T   L   Y   Y   M   R   L   *   Y   F   *   R   K   K
                 151/51
                 GAA TAT GCC TAT GCC
                  E   Y   A   Y   A
                  N   M   P   L   Q
                  C   I   *   C   K
181/61
AGG GCT TCG GGA AAG AGG CGC CTC AGG CAA GCA AAA AAA AAA AAA AAA AGA AAA
 R   A   S   G   K   R   R   L   R   Q   A   K   K   K   K   K   R   K
 G   L   R   E   R   G   A   S   G   A   Q   K   K   K   K   K   E   K
 L   F   G   K   E   A   P   L   S   Q   K   K   K   K   K   K   R   K
          211/71
241/81
GAT TCC GGA AAG ATC TAT GAA AAA TTT ATG CAG CAA TGA GAG TTA TAA GGA TTT CTC TTT
 D   S   G   K   I   Y   E   K   F   M   Q   Q   *   E   L   *   G   F   L   F
 I   R   E   R   S   M   *   K   L   C   A   *   R   V   I   R   D   F   S   P
 F   W   L   D   L   *   R   E   A   D   S   N   *   E   V   K   I   L   L   L
            271/91
301/101                            331/111
TTA TGG TTA TAG GTT TCA TTC TAA AAT CAA GCA TAA AAT CAT TTG TGT TTT GTC CTC TTT
 L   W   L   *   V   S   F   *   N   Q   A   *   N   H   L   C   F   V   L   F
 Y   G   Y   R   F   H   S   K   I   S   H   I   K   S   C   V   F   S   S   F
 M   V   I           F   I   L   K   N   S   K   *   I   F   C   L   C   L   F
```

```
1201/401
TCA GCG CAC TAC CCC TTA GAG ATC TGG ATT ATA TCA AAC TTG CCA CTG ACC AGT TTG GCT
 S   A   H   Y   P   L   E   I   W   I   I   S   N   L   P   L   T   S   L   A
1231/411
                                        I   L   Y   I   K   L   C   A   H   T   D   Q   V   F   W   G   L
1261/421
GCC GTT TTC TTC AAA AAA AAT TAG AAA CCC ATA GTG AAT CCA ATA TGG TGA GAG ACT TGA
 A   V   F   F   K   K   N   *   K   P   I   V   N   P   I   W   *   E   T   *
                                        P   F   F   K   K   K   N   L   R   E   N   T   P   Q   N   M   V   G   D   L
1321/441
TGT ATG AAC AAA TTA AGC CAT TTT TCT TGG TTA TTT TGG ATC CGT TCG GTA ACT ATT
 C   M   N   K   L   S   H   F   S   W   L   F   W   I   R   S   V   T   I
                                        Y   E   Q   I   *   A   P   F   L   G   D   L   F   G   S   V   R   *   Y   L   F
1381/461                                1411/471
TGG TTC AAA AAC TAT GCG ATT ATT TAA CTG AAA AGA CAT TAT TAA TAC AAA CAA ATT
 W   F   K   N   Y   A   I   I   *   L   K   R   H   Y   *   Y   K   Q   I
                                        G   S   K   T   M   R   L   F   N   *   K   E   T   L   L   I   Q   T   N
1441/481
TAT ATC CAA ATG CTG TTT TCC AAA TAT ATC TTA TCA TCA GAA CTC GTT CCT TAC AGA AAA
 Y   I   Q   M   L   F   S   K   Y   I   L   S   S   E   L   V   P   Y   R   K
                                        I   S   P   N   C   F   P   N   I   S   Y   H   Q   N   S   F   L   T   E
1501/501                                1531/511
TTA TAG ACA CTC TCG TCG ATA ACG AAG TGG AGC ATC TCA TCG ATC TCA TTA TTA AGG GAT TTT CCC TAC AGA AAG
 L   *   T   L   S   S   I   T   K   W   S   I   S   S   I   S   L   L   R   D   F   P   Y   R   K
                                        D   T   L   R   R   *   R   S   G   A   S   H   R   S   H   Y   *   G   I   F   P   T   E   R
1561/521                                1591/531
AAT TTA CTT CGA TTG AGC AAG TGG TTA TAA ACG ATC TTA ATG GTA ACC ATG TGA
 N   L   L   R   L   S   K   W   L   *   T   I   L   M   V   T   M   *
                                        I   Y   F   D   *   A   S   G   Y   K   R   S   *   W   *   P   C   D
                                        F   T   S   I   E   Q   V   V   I   N   D   L   N   G   N   H   V   I
```

FIG. 16D

```
1621/541
TTC AAA AGT GTA TTT TCA AAT TCT CGC CAT CAA AAT TTG GTT TCA TAG ATG CTA TTG
 F   K   S   V   F   S   N   S   R   H   Q   N   L   V   S   *   M   L   L
                                                          1651/551
                                                          Q   K         I   D   A   I   C   V
1681/561
TAG AAC AAA ATA TCA ATA II I *  Y   I   F   Q   K   N   I   F   V   F   H   I   R   C   A   Y   T   Q   K
 *   N   K   I   S   I   Y   I   F   Q   K   N   I   F   V   F   H   I   R   C   A   Y   T   Q   K
 R   T   K                                                1711/571
                                                          K   F         P   L   Y   T
1741/581
AAT TAC TAA GCG TTT GTA CTC TAC AAC AAA CCC ATA AAC ATG GTT GTT GCG TAC TAC AAA TTG TGC AGT
 N   Y   *   A   F   V   L   Y   N   K   P   I   N   M   V   V   A   Y   Y   K   L   C   S
                                1771/591
                                H   K         F   S   K   N   I                       L   C   A   V   F
1801/601
TCC TTC CTG GAT TAA TCA ACG ATC AGT TCG ATT ATA TCA CAC TTT TAT TGA AAA TTG TGT TAG ATA
 S   F   L   D   *   S   T   I   S   S   I   I   S   H   F   Y   *   K   L   C   *   I
                                1831/611
                                F   Q   K         N   I   L   Y   I         E   K         *   R   D   Y   I
1861/621
TCA AAG AAT TAT CTT GTT TGA AGT TCT CAA CCT TAT TGG CTG AAA ATG GGG GTG CCT CCC AAA ATG AAT TAT
 S   K   N   Y   L   V   *   S   S   Q   P   Y   W   L   K   M   G   V   P   P   K   M   N   Y
                                                          1891/631
                                                          N   *   L   Y   I   F         V   L   D   Y   M
1921/641
GTC AAC TAT GTT TGT TGA AGT TCT CAA CCT TAT TGG CTG AAA ATG GGG GTG CCT CCC AAA ATG AAT TAT
1951/651
                                                          Q   K         P   Y   I   S   H   I   K   F   K   *   N   E
1981/661
TTA GAA TCA II I Y II I  * N  N  TCA TTA ATA TTA AAA AAT TAT
 L   E   S   I   I   Y   I   *   N   S   L   I   L   K   N   Y
 *   R                                                    2011/671
                                                          Y   H   I   K   *   N         L   K   I   L
2011/671
ACA ATG GGG GTG CCT CCC AAA GGA CTG CAG
 T   M   G   C   L   P   K   D   L   Q
     W   G   A         Q   R   T         C   S
             P   R         K         L   Q   V
```

```
2461/821
ATA AGA ACC CCC ATA ACA AAA ATA GTC ATA ATC ATA ATC ATA ATC ATA ACC ATG
 I  R  T  P  I  T  K  I  V  I  I  I  I  I  I  I  T  M
 *  K  E  P  P  H  *  Q  K  *  S  H  *  S  H  H  *  P  C
2521/841                                              2491/831
CTC ACA ATA ATA ATA ACA ATA ATC AAA AGA GTC ATA CCC GTC ATT TTT CTT TAC CAG
 L  T  I  I  I  Q  I  I  K  R  V  I  P  V  I  F  L  Y  Q
 S  Q  *  N  N  N  *  N  Q  K  S  Y  P  S  F  F  S  T  S
2581/861                                              2551/851
CTA ATG CTT ACC ATA GAA GAA GTA ACA GCT CTG TAA CCA ATA ATT TCT CAA ACC AAT ATG
 L  M  L  T  I  E  E  V  T  A  L  *  P  I  I  S  Q  T  N  M
 N  A  Y  H  *  K  K  *  Q  L  C  N  Q  *  F  L  K  P  I  C
2641/881                                              2611/871
CAC AAG ATC AGA AAA TTC ACT CTC CGC AAC ATA ATT CTC AAA CTA ACC CAC CAT TGG TAA GCC ATA ATC
 H  K  I  R  K  F  T  L  R  N  I  I  L  K  L  T  H  H  W  *  A  I  I
 T  R  S  E  N  S  L  S  A  T  *  N  Y  E  N  F  N  Q  N  A  Y  P
2701/901                                              2671/891
CCT CGA TGG GAG CAC CTT CTT CTT TGA ATT CTC AAA CTA ACC ATG TAA TGG CAC ATC CTA ATT CTG CTG
 P  R  W  E  H  L  L  L  *  I  L  K  L  T  M  *  W  H  I  L  I  L
 L  D  G  S  T  P  F  F  Q  N  S  Q  T  N  P  P  L  A  H  P  N  S  A  A
2761/921                                              2731/911
CGT TAC AAA ACT TCG ACA ACC AGT TTG CAA ATT TAA CAA ATT CTC AAG TGA ATC CTA ATG TTT CAA GGG
 R  Y  K  T  S  T  T  S  L  Q  I  *  Q  I  L  K  *  I  L  M  F  Q  G
 V  T  N  L  R  Q  P  V  C  K  F  N  N  L  S  S  N  S  *  N  V  S  R  G
2821/941                                              2791/931
CAC CAA TCC ATT CGT TCT CAT CAT CTA ACA ATG TGA ATC CTA CCA ATG TTT CAA GGG
 H  Q  S  I  R  S  H  H  L  T  M  *  I  L  P  M  F  Q  G
 T  N  P  F  V  L  I  I  *  H  Y  *  S  *  N  V  S  R  G
                                                      2851/951
```

```
3301/1101
TTT GAG CCG GAA AAA AAT GGT AAA GCA AAC TAT TGC CAT CTT TAT ATT TTG TAT TCT GTT
 F   E   P   E   K   N   G   K   A   N   Y   C   H   L   Y   I   L   Y   S   V
 L   *   S   R   K   M   V   K   Q   T   I   A   I   F   L   Y   I   L   F
     *   A   G   K   W   *   S   K   L   L   P   S   L   Y   F   C   V   F   C   F
3361/1121                                          3391/1131
TCC GAA CAC GTA TCC AAA ATC CTC CCA CTG CCT TTG CAG GGT TAG CAT TGC TCC CTA CCA
 S   E   H   V   S   K   I   L   P   L   P   L   Q   G   *   H   C   S   L   P
 P   N   T   Y   P   K   S   S   H   C   L   C   R   V   S   I   A   L   P   Y   Q
   R   T   R   I   Q   N   P   P   T   A   F   A   G   L   A   L   L   P   T   K
3421/1141                                          3451/1151
AAA TGA TCT AAT TTT TTT TTT TTG AAT CGT TTT TTG TC
 K   *   S   N   F   F   F   L   N   R   F   L
 N   D   L   I   F   F   F   *   I   V   F   C
   M   I   *   F   F   F   E   S   F   F   V
```

FIG. 16I

```
1/1
GTG TCT TCC ATG GAG TGA ATT GTG ATT TGT GAA TTA TAT CTG TCC AAT ACC GTT GCC TTG
 V   S   S   M   E   *   I   V   I   C   E   L   Y   L   S   N   T   V   A   L
                                                               31/11
  C   L   P   W   H   G   V   N   C   D   L   *   F   V   *   I   L   P   C   L   V
61/21
TTG GGA GCT CAG ATA GAA AAG ACA TCT TAA TTC CAG ACA GTC TAT TCT CTG TCT ATT TCT
 L   G   A   Q   I   E   K   T   S   *   F   Q   T   V   Y   S   L   S   I   S
                                   91/31
  W   E   L   R   *   K   R   D   I   L   N   S   R   Q   S   L   F   L   C   F   L
                                                              151/51
  G   S   D   R   K   D   I   L   I   P   D   S   L   F   S   V   Y   F   L
121/41
CTT TGT GAC TGC AAA TTT GTG ACG CCT TTT CTT ATT ACT CAT GTA TTT GTC ACT
 L   C   D   C   K   F   V   T   P   F   L   I   T   H   V   F   V   T
  F   V   T   A   N   L   C   D   A   L   F   L   L   Y   L   C   L   S   H   S
181/61
  L   *   L   Q   I   L   I   C   D   *   R   F   S   Y   Y   S   C   I   C   H   S
CTT GAC GAT TGT TTT TCT ATA TTT TTT TTG TTG TTC TGG CCT CCA GAG AAT AAA AAA
 L   D   D   C   F   S   I   F   F   L   L   F   W   P   P   E   N   K   K
  L   T   I   V   F   L   Y   F   F   L   F   C   G   L   Q   R   I   K   N
                                   271/91
  *   R   L   F   Y   I   F   F   F   V   L   G   S   S   R   E   *   K   I
241/81
TAA TGA TCA ATA TAG TAG ATA GTA TAG TTA TAT TCT TAT TCG TTG CAC CTT GTT TAA CAA
 *   *   S   I   *   *   I   V   *   L   Y   S   L   S   L   H   L   V   *   Q
                                                              331/111
  N   D   Q   Y   S   R   *   Y   I   V   I   L   Y   I   R   C   T   L   F   N   K
  M   I   N   I   V   D   S   I   V   *   S   Y   I   F   L   F   V   A   P   C   L   T   N
301/101
ATC ACT CAG ACT CAA AGA GAA TAT CGG TTG GTT ATC TCT CTC CGA AGG TGA ACA GCA AAC
 I   T   Q   T   Q   R   E   Y   R   L   V   I   S   L   R   R   *   T   A   N
  S   L   R   L   K   E   N   I   G   W   L   S   L   S   E   G   E   Q   Q   T
                                                              391/131
  H   S   D   S   K   R   I   S   V   G   Y   L   S   P   K   V   N   S   K   Q
361/121
AGT ACC TCA CGT CTT TTT GAA TAG TTT TTT TTG AAA CAG AAA AAA AAC TTT
 S   T   S   R   L   F   E   *   F   F   L   K   Q   K   K   N   F
  V   P   H   V   F   F   N   I   V   F   F   F   C   *   N   R   K   N   T   F
  Y   L   T   S   F   F   *   I   S   F   F   F   V   E   T   E   K   K   L   S
```

```
781/261
AAA CAG TCA ATT CTG CTT TAG AGC AGT TGC AAC TAG ATG ATC CAG AGG AAA ACG CCA CCT
 K   Q   S   I   L   L   *   S   S   C   N   *   M   I   Q   R   K   T   P   P
 N   S   Q   F   C   F   R   A   V   A   T   R   *   D   P   E   E   K   R   H   L
 T   V   N   S   A   L   E   Q   L   Q   L   D   D   P   E   E   N   A   T   S
                                        811/271
841/281
CTA ATG CAT TTG CGA ATA AAG TTT CTC AAG ATT CTC AAT TCG CTA ATG GCC CTC CGT CGC
 L   M   H   L   R   I   K   F   L   K   I   L   N   S   L   M   A   L   R   R
 *   C   I   *   E   *   K   S   F   S   R   F   S   I   R   *   W   P   S   V   A
 N   A   F   A   N   K   V   S   Q   D   S   Q   F   A   N   G   P   P   S   Q
901/301
AAA TGT TTC CAC ATC CAC AAA TGA GCT TCA GCT GAA TGG GTG GTT EWN G L H A S C P T L S Q M D
 K   C   F   H   I   H   K   *   A   S   A   E   W   V   V   G   L   H   A   S
 N   V   S   T   S   T   N   E   L   Q   L   N   G   W   *   W   A   L   H   P   Y   *   *   N   D
 M   F   P   H   P   Q   M   S   F   S   *   M   G   M   G   F   M   P   Y   L   *   N   D
                                        931/311
961/321
TGC AGG TTC CTC ATA ATC CTT GTC CAT TTT TTC CGC CCC CTG ATT TTA ATG ATC CAA CAG
 C   R   F   L   I   I   L   V   H   F   F   R   P   L   I   L   M   I   Q   Q
 A   G   S   S   *   S   L   *   S   I   F   S   A   P   *   F   *   *   S   N   S
 Q   V   P   H   N   P   C   P   F   F   P   P   P   D   F   N   D   P   T   A
                                        991/331
1021/341
CAC CAT TGA GTA GCT CGC CCT TGA ATG CAG GCG GTC CAC CAA TGT TAT TCA AGA ATG ACT
 H   H   *   V   A   R   P   *   M   Q   A   V   H   Q   C   Y   S   R   M   T
 T   I   E   *   S   L   A   L   E   C   R   R   S   T   N   V   I   Q   E   *   L
 P   L   S   S   P   L   N   A   G   P   P   M   L   F   K   N   D   S
                                        1051/351
1081/361
CAC TTC CAT TTC AAA TGC TGT CGG CTG CGG TAG CAA CTC AAG GTG GAC AAA ATC
 H   F   H   F   K   C   C   R   L   R   *   Q   L   K   V   D   K   I
 T   S   I   S   Q   M   L   S   A   V   F   G   A   V   A   N   S   R   W   T   K   S
 L   P   F   Q   N   A   V   L   R   C   C   Q   A   T   Q   G   G   Q   N   L
                                        1111/371
1141/381
TAA ACC CAT TGA TAA ATG ACA ATT CAA TGA AGG TAT TGC CAA TCG CAT CGG CTG ATC CGT
 *   T   H   *   *   M   T   I   Q   *   R   Y   C   Q   S   H   R   L   I   R
 K   P   I   D   K   *   Q   F   N   E   G   I   A   N   R   I   G   *   S   V
 N   P   L   I   N   D   N   S   M   K   V   L   P   I   A   S   A   D   P   L
                                        1171/391

FIG. 17C
```

1201/401
TAT GGA CTC ATT CAA ACG TAC CAG GAT CAG CAT CTG TAG CCA TTG AAG AAA CCA CCG CTA
 Y   G   L   I   Q   T   Y   Q   D   Q   H   L   *   P   L   K   K   P   P   L
 M   D   S   F   K   R   T   R   I   S   I   C   S   H   *   R   N   H   R   Y
 W   T   H   S   N   V   P   G   S   A   S   V   A   I   E   E   T   T   A   T
1261/421                                                    1291/431
CTC TAC AAG AAA GCC TAC CAT CTA AGG GCA GGG AGT CTA ATA ATA AGG CTA GTT CGT TCA
 L   Y   K   K   A   Y   H   L   R   A   G   S   L   I   I   R   L   V   R   S
 S   T   R   K   P   T   I   *   G   Q   G   V   *   *   *   G   *   F   V   Q
 L   Q   E   S   L   P   S   K   G   R   E   S   N   N   K   A   S   S   F   R
1321/441                                                    1351/451
GAA GAC AAA CTT TTC ATG CTT TAT CAC CAA CTG ACC TTA TCA ATG CGG CCA ACA ATG TAA
 E   D   K   L   F   M   L   Y   H   Q   L   T   L   S   M   R   P   T   M   *
 K   T   N   F   S   C   F   I   T   N   *   P   Y   Q   C   G   Q   Q   N   V  
 R   Q   T   F   H   A   L   S   P   T   D   L   I   N   A   A   N   N   V   T
1381/461                                                    1411/471
CCT TGT CAA AGG ACT TCC AAT CTG ACA TGC AGA ATT TTT CTA AGG CTA AGA AAC CGT CTG
 P   C   Q   R   T   S   N   L   T   C   R   I   F   L   R   L   R   N   R   L
 L   V   K   G   L   P   I   *   H   A   E   F   F   *   G   *   E   T   V   C
 S   L   S   E   D   F   Q   S   D   M   Q   N   F   S   E   A   K   K   P   S   V
1441/481                                                    1471/491
TAG GAG CTA ACA ATA CTG CAA AAA CCA GAA CTC AAT CCA TAT CTT TTG ATA ATA CTC CCT
 *   E   L   T   I   L   Q   K   P   E   L   N   P   Y   L   L   I   I   L   P
 R   S   *   Q   Y   C   K   N   Q   N   S   I   H   I   S   F   D   N   T   P   S
 G   A   N   N   T   A   K   T   R   T   Q   S   I   H   I   F   *   *   Y   S   L
1501/501                                                    1531/511
CCT CAA CGT CAT TTA TAC CCC CAA CCA ATA GTG TTT CTG AGA AAT TAT CCG ATT TCA AAA
 P   Q   R   H   L   Y   P   Q   P   I   V   F   L   R   N   Y   P   I   S   K
 P   N   V   I   Y   T   P   N   Q   *   C   F   *   E   I   I   R   F   Q   N
 L   N   T   S   F   I   P   P   T   N   S   V   S   *   E   K   L   S   D   F   K   I
1561/521                                                    1591/531
TAG AAA CCT CGA AGG AGG ATT TGA TTA ATA AAA CTG CAC CAG AAA AAG AGA GTC CTA
 *   K   P   R   R   R   I   *   L   I   K   L   H   Q   K   K   R   V   L
 R   N   L   E   G   G   F   D   *   *   N   C   T   S   *   K   K   E   S   Y
 E   T   S   K   E   D   L   I   N   K   T   A   P   A   K   K   R   S   P   T

```
2041/681
GGC TTT ATA GCA CTC CAC CTC CCT TCA ACG CAA TGG TTC CGC CTC ATT TGT TGG CTC AAA
 G   F   I   A   L   H   L   P   S   T   Q   W   F   R   L   I   C   W   L   K
 A   L   *   S   T   P   P   P   F   N   A   M   V   P   H   L   A   Q   N
2101/701                                                                      2131/711
ATC ATA TGC CGT TAA TGA ATA GCG CCA ATA ATC ATG GTC GTA ATA ACA ATA GCA
 I   I   C   R   *   *   I   A   P   I   I   M   V   V   I   T   I   A
 S   Y   A   V   N   E   *   R   Q   *   S   W   S   *   *   Q   *   H
 H   M   P   L   M   N   S   A   N   N   K   H   H   G   R   N   N   S   M
2161/721                                                                      2191/731
TGT CAA GTC ATA ATG ACA ATG ACA ACA TTG GTA ATT CTA ATT ACA ATA ACA ATA AAG ACA CAG
 C   Q   V   I   M   T   M   T   T   L   V   I   L   I   T   I   T   I   K   T   Q
 V   K   S   *   *   Q   *   Q   H   W   *   F   *   L   Q   *   Y   *   R   H   R
 S   S   H   N   D   N   D   N   I   G   N   S   N   Y   N   N   N   K   D   T   G
2221/741                                                                      2251/751
GTC GTT CTA ACG TTG GTA AAA TGA AAA ATA TGA AAA ACA GTT ATC ATG GCT ACT ATA ATA
 V   V   L   T   L   V   K   *   K   I   *   K   T   V   I   M   A   T   I   I
 S   F   *   R   W   *   K   N   E   K   Y   E   K   N   S   W   L   L   *   *
 R   S   N   V   G   V   K   M   K   N   M   K   N   S   Y   H   G   Y   Y   N
2281/761                                                                      2311/771
ACA ATA ATA ATA AAC GTA AAA TTG AGG AGT CGT CGA GAT TTG CGG ACG CAG TTT TAG
 T   I   I   I   N   V   K   L   R   S   R   R   D   L   R   T   Q   F   *
 Q   *   *   *   T   *   N   *   E   E   S   V   E   I   C   G   R   T   Q
 N   N   N   N   K   R   K   I   E   E   V   R   R   F   A   D   A   V   L   D
2341/781                                                                      2371/791
ACA GCG CGG AAA AAC GTA TTC ACT CAT TGT GTA AAG ACC AAC ATG GTT GTC GTT TTC TGC
 T   A   R   K   N   V   F   T   H   C   V   K   T   N   M   V   V   V   F   C
 Q   R   G   E   K   Q   *   N   I   V   *   R   P   T   W   G   R   F   L   *
 S   A   E   K   T   Y   I   E   S   *   S   K   T   E   H   G   C   V   F   L   Q
2401/801
ACC AAT ATA TCG GAA GTA TTC ACT CAT TGT GTA AAG ACC AAC ATG GTT GTC GTT TTC TGC
 T   N   I   S   E   V   F   T   H   C   V   K   T   N   M   V   V   V   F   C
 P   I   Y   R   K   Y   S   L   I   V   *   R   P   T   W   G   C   R   F   L
 Q   Y   I   G   S   I   H   S   L   C   K   D   Q   H   G   C   V   F   S   A   Q

```
3301/1101
TTG TGG CGC CTT TAC TGG TGG GCC CCA TAA GAA ATA CAC CTC ATG GTA AAA GAA TCA TCG
 L   W   R   L   Y   W   W   A   P   *   E   I   H   L   M   V   K   E   S   S
 C   G   A   F   L   V   G   P   I   R   N   T   P   H   G   K   R   I   I   G
 V   A   P   L   Y   G   G   P   *   K   Y   Y   T   S   W   *   K   N   H   R
3361/1121                                          3391/1131
GAA TGT TAC ATT TAG ATT CAT AGT TGA TAC ATA TAT CCT CAG TTT AGC TTT TTT TAC GTT
 E   C   Y   I   *   I   H   S   *   Y   I   Y   P   Q   F   S   F   F   Y   V
 N   V   T   F   R   F   I   V   D   T   Y   I   L   S   L   A   F   F   T   L
 K   L   H   L   D   S   S   *   L   I   H   I   S   S   V   *   L   F   L   R
3421/1141                                          3451/1151
AGC CTC ATA TAA TAT CTT TTG TAC AAT ATA CAT ACT AAA ATA CAT CAT TTT TTT TTT CGT
 S   L   I   *   Y   L   L   Y   N   I   H   T   K   I   H   H   F   F   F   R
 A   S   Y   N   I   F   C   T   I   Y   T   L   K   Y   T   I   F   F   F   V
 P   H   I   *   I   S   L   V   Q   Y   *   N   N   T   S   S   F   F   F   S
3481/1161                                          3511/1171
TCA AAT GAA TAT CCA AAG CAA ATA AGA GAA GGA GAT CGC CCT AGA AAA CAG AAT GTT CTT
 S   N   E   Y   P   K   Q   I   R   E   G   D   R   P   R   K   Q   N   V   L
 Q   M   N   I   S   K   A   K   K   K   R   K   I   A   L   E   N   R   M   F
 K   *   R   I   Q   S   N   K   R   R   R   R   S   P   *   K   T   E   C   S
3541/1181                                          3571/1191
AGT GTT GAA GAA ATA AGA GAA GGA GAT CGC CCT AGA AAA CAG AAT GTT CTT ATT TAA ATA
 S   V   E   E   I   R   E   G   D   R   P   R   K   Q   N   V   L   I   *   I
 V   L   K   K   *   E   K   E   I   A   L   *   K   T   E   C   S   Y   L   N
 C   *   R   N   K   R   R   R   S   P   *   K   T   E   C   S   Y   L   N   K
3601/1201                                          3631/1211
AGT AAA CTC AAA AGA AGA AAA AAA AGA AAA GGA TTT TTG AGA ACT TTT ATC TAT ACA AAC
 S   K   L   K   R   R   K   K   R   K   G   F   L   R   T   F   I   Y   T   N
 V   N   S   K   E   E   K   K   E   K   G   F   *   E   L   L   S   I   Q   T
 *   T   Q   K   K   R   K   R   K   R   D   F   *   N   F   Y   L   Y   K   R
3661/1221                                          3691/1231
GTA TAC GTT TAA CTA TCT GGA TAA ACG TCG CTC CAC AGG ATA CTG TAG AGG TCC TCA AGA
 V   Y   V   *   L   S   G   *   T   S   L   H   R   I   L   *   R   S   S   R
 Y   T   F   N   Y   L   D   K   R   R   S   T   G   Y   C   R   G   P   Q   D
 I   R   L   T   I   W   I   N   V   A   P   Q   D   T   V   E   V   L   K   I
```

FIG. 171

```
3721/1241                                                   3751/1251
TCA CCG TTA TTA ACA AAT TCA TCT AGT GTC CCC AAA TTA AAA CTA GTT GCA GAA AAA TTG
 S   P   L   L   T   N   S   S   S   V   P   K   L   K   L   V   A   E   K   L
 H   R   Y   *   Q   I   H   I   L   V   S   P   N   *   N   *   S   C   R   K   N   C
 T   V   I   N   K   F   I   *   C   P   I   K   T                   L       I   V
3781/1261                                                   3811/1271
TTA CTG TTG TTG TTA ATA TTG TTT TTA TTG TTT TTA TTG TTG CTT GTG TTG TTG ATT TCA
 L   L   L   L   L   I   L   F   L   L   F   L   L   L   L   V   L   L   I   S
 Y   C   C   C   C   *   Y   C   F   Y   C   F   I   V   F   I   V   F   H
 T   V   V   V   V   N   I                                   L   C   C   *   F   H
3841/1281                                                   3871/1291
TTT GTG TTC ATA AAT GGT ACT TGT ACT GAA GTG GGT ATT TGC TGA GCA TTG ATT GGT
 F   V   F   I   N   G   T   C   T   E   V   G   I   C   *   A   L   I   G
 L   C   S   *   M   V   L   L   *   K   W   V   F   A   E   H   *   L   V
 C   V   H   K   W   Y   L   Y   *   S   G   Y   L   L   S   I   D   W   F
3901/1301                                                   3931/1311
TTA TTA GAT TGG ACT TGC GAA TTA TTT TGC CCA TTT GTT GGT TGC GCG TAA TCG GAA TTG
 L   L   D   W   T   C   E   L   F   C   P   F   V   G   C   A   *   S   E   L
 Y   *   I   G   L   A   N   Y   F   A   H   L   F   A   V   L   R   V   G   L   *
 I   R   L   D   L   R   *   I   H   L   P   I   C   W   L   R   V   G   I   D
3961/1321
ATC ATA TCA GAC ACG GAT AAT GAC CTA AAT GAA GGC AAT T
 I   I   S   D   T   D   N   D   L   N   E   G   N
 S   Y   Q   T   R   I   M   T   *   M   K   A   I
 H   I   R   H   G   *   *   *   P   K   *   R   Q
```

```
421/141
tgc gtt cca tgg atg aac tga atc atg att ttc aag cac ttg ctc tgg agg gaa gag cga
 C   V   P   W   M   N   *   I   M   I   F   K   H   L   L   W   R   E   E   R
 A   F   H   G   D   E   L   N   *   Y   S   *   T   *   C   S   G   G   K   S   D
 R   S   M   D   E   *   T   *   I   H   D   F   Q   A   L   A   L   E   G   R   A   M
451/151
481/161
tgg gag agc agc tct tgc cag gta aaa agt ttt ggg aaa cag atg aat cca gca aag atg
 W   E   S   S   S   C   Q   V   K   S   F   G   K   Q   M   N   P   A   K   M
 G   R   A   A   L   L   P   G   K   *   K   V   L   G   N   R   *   I   Q   R   W
 G   E   Q   Q   F   *   A   R   G   K   F   W   E   T   D   E   S   K   D   G
541/181
571/191
gac caa aag gaa tat tcc tgg gtg atc aat ggc gag aca gtg cct ggg gaa cat cag atc
 D   Q   K   E   Y   S   W   V   I   N   G   E   T   V   P   G   E   H   Q   I
 T   K   R   N   I   P   G   *   S   M   A   R   Q   C   L   G   N   I   R   S
 P   K   G   I   F   L   G   D   Q   W   R   D   S   A   W   G   T   S   D   H
601/201
631/211
att cag ttt ccc agc caa tca gct ccc aga gac ctg ctg aga gtt tcc atg tga aca
 I   Q   F   P   S   Q   S   A   P   R   D   L   L   R   V   S   M   *   T
 F   S   F   P   A   N   H   G   A   E   K   T   W   S   E   F   P   C   E   Q
 S   V   S   Q   P   I   M   V   Q   R   R   P   G   Q   S   F   H   V   N   S
661/231
691/231
gtg agg tca att ctg tac tgt ccc cac gat cgg aga gtg ggg gac tag gcg tta gca tgg
 V   R   S   I   L   Y   C   P   H   D   R   R   V   G   D   *   A   L   A   W
 *   G   Q   F   C   T   V   P   T   I   G   E   W   G   T   L   G   *   H   G
 E   V   N   S   V   L   S   P   R   S   G   R   V   G   R   L   G   V   S   M   V
721/241
751/251
tgg agt atg tgt tga gct cat ccc cgg gcg att cct gtc taa gaa gag gat ttg gcc
 W   S   M   C   *   A   H   P   R   A   I   P   V   *   E   E   D   L   A
 G   V   C   V   E   L   I   P   V   R   F   L   S   K   K   R   I   W   P
 E   Y   V   L   S   S   P   G   R   S   C   L   R   K   G   F   G   P
```

FIG. 18B

```
781/261
caa ggg atg cag aca gtg atg aaa acg aca aag gtg aaa aga aga aca aag gta cgt ttg
 Q   G   M   Q   T   V   M   K   T   T   K   V   K   R   R   T   K   V   R   L
     K   G   C   R   D   S   D   E   N   K   R   D   K   G   E   *   K   E   E   Q   N   K   G   Y   T   F   D
841/281                                 811/271                                 871/291
atg gag ata agc tag gag att tga agg agg gtg atg tga atg * gtc atg tgg aca aga cca atg gtt
 M   E   I   S   *   E   I   *   R   R   V   M   *   C   D   V   M   D   K   T   N   G   L
 W   R   *   A   R   F   E   G   G   G   *   D   V   M   D   K   T   N   G   L
     G   D   K   L   G   D   L   K   E   E   G   D   V   M   D   K   T   N   G   L
901/301                                                 931/311
tac cag tgc aga atg gga ttg atg cag acg tca aag att tta gcc gta ccc ctg gta att
 Y   Q   C   R   M   G   L   M   Q   T   S   K   I   L   A   V   P   L   V   I
 T   S   A   E   W   D   *   C   R   R   F   *   S   R   T   P   G   N   C
     P   V   Q   N   G   I   D   A   D   V   K   D   F   *   S   R   T   P   G   N   C
961/321                                                 991/331
gcc aga act ctg cta atg aag tgg ato ttc tgg gtc caa aca atg gtt ctg agg gct
 A   R   T   L   L   M   K   W   I   F   W   V   Q   T   M   V   L   R   A
 P   E   L   C   *   N   E   V   D   L   S   G   S   K   P   N   Q   *   G   E   G   L
     Q   N   S   A   *   M   *   S   G   D   L   L   Q   P   N   Q   S   E   G   L
1021/341                                                1051/351
tag ccc agc tga cca gca cca atg gtg caa agc tgg agg att tct cca aca tgg agt
 *   P   S   *   P   A   P   M   V   Q   S   W   R   I   S   P   T   W   S
     S   P   A   D   Q   H   Q   W   C   A   K   P   V   E   D   F   S   N   M   E   S
         A   Q   L   T   S   T   N   G   Q   K   P   V   E   D   F   S   N   M   E   S
1081/361                                                1111/371
ccc aga gta tac cct tgg acc cca tgg aac atg tgg gca tgg gca ctc tto agt ctg att
 P   R   V   Y   P   W   T   P   W   N   M   W   A   W   S   L   F   S   L   I
 P   E   C   P   L   G   P   H   G   T   C   G   H   V   G   M   E   P   L   Q   F   D   Y
     Q   S   V   P   L   D   P   M   E   H   V   G   M   E   P   L   Q   F   D   Y
1141/381                                                1171/391
att cag gca gca cgc agg tac ctg tgg act cag cag caa ctg tgg gac ttt ttg act aca
 I   Q   A   A   R   R   Y   L   W   T   Q   Q   Q   L   W   D   F   L   T   T
 F   R   H   A   G   T   C   G   L   S   N   C   G   *   *   G   L   *   L   Q
     S   G   T   Q   V   P   V   D   P   S   A   A   A   T   V   G   L   F   D   Y   N
```

FIG. 18C

```
1201/401
att ctc aac aac agc tgt tcc aaa gac cta atg aag cga ttg ctg tcc agc agt tga cag ctg
 I   L   N   S   C   S   K   D   L   M   K   R   L   L   S   S   S   *   Q   L
1261/421                                          1291/431
ctc agc agc agt atg atg cac tgg cag ctg ctc atc aga agc ctg atc aga agc ctc cca
 L   S   S   S   M   H   W   Q   L   L   I   R   S   L   I   R   S   L   P
1321/441                                          1351/451
ctg agt ttg tcc cca atc cat aca tca gcg gtg atc ccc cag gga cgg acc cct aca
 L   S   L   S   P   I   H   T   S   A   V   I   P   Q   G   R   T   P   T
1381/461                                          1411/471
cag gtg gat tgg ctg cag cag cga cac tag gcc tag ctg tgg tcc ctc acc agt att atg
 Q   V   D   W   L   Q   Q   R   H   *   A   *   L   W   S   L   T   S   I   M
1441/481                                          1471/491
gag tta ctc cct ggg gag tct acc ctg cca gtc ttt tcc agc agc aag ctg ccg
 E   L   L   P   G   E   S   T   L   P   V   F   S   S   S   K   L   P
1501/501                                          1531/511
ctg cag caa att cag cta atc aac aga ccc cac agg gtc agc cac agg ctg agc
 L   Q   Q   I   Q   L   I   N   R   P   H   R   V   S   H   R   L   S
1561/521                                          1591/531
agg tta tcc gtg gag gag cca aac gcc aac gtc ctt tga cca caa acc aga acc
 R   L   S   V   E   E   P   N   A   N   V   L   *   P   Q   T   R   T

```
2461/821                    2491/831
cca gcc tct tca gcc cga gca gca ctc ttt tat ctt cct ctc gtt tgc gat atg gaa tgt
 P   A   S   L   Q   A   R   A   L   F   Y   L   P   L   V   C   D   M   E   C
2521/841                    2551/851
ctg atg tca tgc att ctg agc ttc agc ttc tgg aag att tta gaa aca acc ggt aca
 L   M   S   C   I   L   S   F   S   F   W   K   I   L   E   T   T   G   T
2581/861                    2611/871
cca att tac aac tgc ggg aga ttg ctg gac ata taa tgg aat ttt ccc aag acc agc atg
 P   I   Y   N   C   G   R   L   L   D   I   *   W   N   F   P   K   T   S   M
2641/881                    2671/891
gtt cca gat tca ttc agc tga aac tgg aga cac cag ctg agc gcc agc ttg tct
 G   P   D   S   F   S   *   N   W   G   H   Q   L   S   A   S   L   S
2701/901                    2731/911
tca atg aaa tcc tca agg ctg cct acc aac toa tgg tgg atg tgt gac gtg ttt gca gaa agg cag aac tgg cag aac gga tta
 S   M   K   S   S   R   L   P   T   N   S   W   W   M   C   D   V   W   Q   N   G   F
2761/921                    2791/931
ttc aga agt tct ttg aat ttg gca gtc ttg gca gtg ttg aac gtc ttg gca gtc ttg aac gtc ttg aac gtc ttg agc agc tgg ctt cag aac tgg cag aac gga tta
 F   R   S   S   L   N   L   A   V   S   L   *   E   Q   K   T   E   A   L   A   L   A   E   R   I   R
2821/941                    2851/951
gag gcc acg tcc tgt cat tgg cac tac aga tgt atg gat gcc gtg tta tcc aga aag ctc
 E   A   T   S   C   H   W   H   Y   R   C   M   Y   G   C   N   A   A   L   P   C   R   V   I   Q   K   S   A   L
```

FIG. 18G

2881/961
ttg agt tta ttc ctt cag acc aga atg aga atg ttc ggg aac tag atg gcc atg tct
L  S  L  V  Y  F  L  Q  T  R  P  A  E  *  N  R  W  F  G  N  *  H  W  P  C  L

2911/971
E  F  I  P  S  D  Q  T  S  R  M  *  R  D  G  S  G  T  R  W  P  V  L

2941/981
tga agt gtg tga agt ctt tgc aat tta tca tag atg cgt tta agg gac agg tat ttg cct tat cca
*  S  V  *  S  L  C  N  L  S  *  M  R  L  R  D  R  Y  L  P  Y  P

2971/991
E  V  C  V  K  D  Q  N  G  N  H  V  V  Q  *  K  C  I  E  C  V  Q

3001/1001
agc cac agt ctt tgc aat tta tca tag atg cgt tta agg gac agg tat ttg cct tat cca
S  P  S  L  C  N  L  S  *  M  R  L  R  D  R  Y  L  P  Y  P

3031/1011

3061/1021
cac atc ctt atg gct gca gag tga tta aga gaa tcc tgg agc act gtc tcc ctg acc aga
H  I  L  M  A  A  E  *  L  R  E  S  W  S  T  V  S  L  T  R

3091/1031

3121/1041
H  P  Y  G  C  R  V  I  Q  R  I  L  E  H  C  L  P  D  Q  T

3151/1051
cac tcc cta ttt tag agg agc agc agc aca cag agc gtc gtc ctg agg ata aaa gca aaa ttg
H  S  L  F  *  R  S  S  S  T  Q  S  V  V  L  R  I  K  A  K  L

3181/1061
T  P  Y  F  R  G  A  S  H  Q  H  T  E  Q  L  V  Q  D  Q  Y  G

3211/1071
gaa att atg taa tcc aac atg tac tgg aga acg gtc gtc ctg agg ata aaa gca aaa ttg
E  I  M  *  S  N  M  Y  W  R  T  V  L  R  I  *  K  Q  N  C

3241/1081
K  L  C  N  P  T  C  H  V  L  E  H  G  A  R  S  P  E  D  K  S  K  I  V

3271/1091
tag cag aaa tcc gag gca atg tac ttg tat tga gtc agc aca aat ttg caa gca atg ttg
*  Q  K  S  E  A  M  Y  L  Y  *  V  S  A  Q  I  C  K  Q  C  L

```
3301/1101
tgg aga agt gtg tta ctc acg cct cac gta cgg agc gcg ctg tgc tca tcg atg agg tgt
 W   R   S   V   L   L   T   P   H   V   R   B   A   L   C   S   S   M   R   C
      E   K   C   V   Y   T   H   A   S   R   T   Y   G   A   R   A   V   L   I   D   E   V   C
3361/1121
gca cca tga acg acg gtc ccc aca gtc cct tat aca cca tga tga agg acc agt atg cca
 A   P   *   T   T   V   P   T   V   P   Y   T   P   *   R   T   S   M   P
      H   H   E   R   R   S   P   H   Q   S   L   I   H   H   D   E   G   P   V   C   Q
                                    3331/1111
                                    3391/1131
3421/1141
act acg tgg tcc aga aga tga ttg acg tgg cgg aga cag gcc aga gaa tcg tca tga
 T   T   W   S   R   R   *   L   T   W   R   G   Q   A   R   E   S   S   C
      L   R   G   P   E   D   *   I   D   V   A   E   P   G   A   R   K   I   V   H   A
3451/1151
3481/1161
ata aga tcc ggc ccc aca tcg caa ctc gta agt aca cct atg gca aga aca tct gtg gac ccc
 I   R   S   G   P   T   S   Q   L   V   S   T   P   M   A   S   T   F   W
      Y   V   Q   K   M   I   D   L   F   V   *   V   H   L   W   Q   K   H   L   A
                                    3511/1171
3541/1181
cca agg tgg aga agt act aca tga aga acg gtg ttg act tag gga cca tct gtg gac ccc
 P   S   W   R   S   T   T   *   R   T   V   L   T   *   G   P   S   V   A   P
      Q   A   G   E   V   L   H   Y   M   K   N   G   C   *   L   R   A   H   L   C   G   P   P
3571/1191
3601/1201
cta atg gta tct gag gca gtg cca gat gtt ccc tca ttc cgg ctg ttc ccc tga acc tca ctg
 L   M   V   S   E   A   V   P   D   V   P   S   F   R   L   F   P   *   T   S   L
      *   W   Y   L   R   Q   C   H   P   L   F   P   H   S   R   *   P   D   L   T   G
3631/1211
3661/1221
gcc cac tgg caa atc caa gca acc aga aat gtt cta gtg tag agt ctg aga cgg gca
 A   H   W   Q   I   Q   A   T   R   N   V   L   V   *   S   L   R   R   A
      P   L   A   N   P   S   N   Q   Q   P   A   T   E   M   F   *   C   R   V   *   S   E   T   G   Q   K
                                    3691/1231
```

```
1/1                                                                          31/11
GGA AGT TAA AGG CAA AAA GCA ATT CAC AGG AAA GAC AGC ACA AGA AAA AAA
 G   S   *   R   Q   K   A   I   H   R   K   D   S   T   R   K   K
 R   V   K   G   K   S   N   S   E   G   R   T   A   Q   E   K   N
 K   L   K   E   K   K   Q   F   T   K   E   R   Q   H   K   K   T
61/21                                                                        91/31
CAG ATT TCA TAA AAA GAC ATT TCA TGA TTC TGG TTC AAA GAC ATT TCC AAC AAG GAA AGT TGC
 Q   I   S   *   K   D   I   S   *   F   W   F   K   D   I   S   N   K   E   S   C
 R   F   F   K   R   H   F   H   D   F   G   S   K   T   F   P   T   R   K   V   A
 D   F   I   K   N   I   V   I   L   V   L   Q   R   H   F   P   Q   Q   G   K   L   L
121/41                                                                       151/51
TAA AGA AGG TGG ACC TAA AGT CAC ATC TAG TGA GAA CTT TGA GAA AAG TAT CAC AAA ACT TGG
 *   R   R   W   T   *   S   H   I   *   E   L   *   E   K   Y   H   K   T   W
 K   E   G   G   P   K   V   T   S   M   R   N   F   R   K   S   I   T   K   L   G
 R   K   V   D   L   K   S   H   L   *   E   E   T   L   E   K   V   S   Q   N   L   G
181/61                                                                       211/71
GAA AAA GGG TGT AAA GCA GTT CAA GAA TAA AGC AGG GGA CAA ATC ACC AAA GAA CAA
 E   K   G   C   K   A   V   Q   E   *   S   R   G   Q   I   T   K   E   Q
 K   K   G   V   K   Q   F   K   N   K   Q   G   D   K   S   P   K   N   K
 K   R   V   *   S   S   R   I   S   K   A   R   W   T   N   H   Q   R   T   N
241/81                                                                       271/91
ATT CCA CCC GGC AAA AAA CAA CAG AAA ATT CAA CAA ATT CCA GCC AGA TGG TAG AAG CGA
 I   P   P   G   K   N   Q   Q   K   I   Q   Q   I   P   A   R   W   *   K   R
 F   Q   P   A   N   K   I   Q   K   F   N   N   S   S   Q   P   D   G   R   S   D
 S   S   R   Q   Q   E   E   K   R   E   N   S   T   R   R   E   A   M
```

FIG. 19A

```
301/101
TGA ATC AGC AGC CAA GAA GCC CAA ATG GGA TGA CTT CAA AAA GAA GAA AGA ACT GAA
 *   I   S   S   Q   E   A   Q   M   G   *   L   Q   K   E   E   R   T   E
     S   A   A   P   R   S   P   K   W   D   F   K   K   R   K   N   *   K
     H   Q   Q   K   K   P   N   G   M   T   S   K   R   K   E   L   K   S
331/111
361/121
GCA AAG CAC ACA ACT CAG TGA CAT TGT TCG GGC AAA GCA GAT
 A   K   H   T   T   Q   *   H   C   S   G   K   A   D
 Q   S   T   Q   L   S   D   I   V   R   A   Q   R   I
 K   A   D   N   S   V   I   L   F   G   S   R   C
391/131
421/141
GTG GGA GAT TTT AAG AAG AAA AGA CTG TGA AAT GTT AAT GAG TGA
 V   G   D   F   K   K   K   R   L   *   N   V   N   E   *
 W   E   I   L   R   R   K   D   C   K   S   K   *   S   V   D
 G   R   F   *   E   E   K   T   V   K   R   V   K   M   S   I
451/151
481/161
TTT GCA GAA GTT GAT TCA AGC GAA AAT TAA AAC TAT TCC ATT TGC ACA CGA TTC AAC TCG
 F   A   E   V   D   S   S   E   N   *   N   Y   S   I   C   T   R   F   N   S
 L   Q   K   L   I   Q   A   K   I   K   T   I   H   F   A   H   T   I   Q   L
 C   R   S   *   F   K   G   K   L   K   L   L   H   L   H   T   D   S   T   R   V
511/171
```

FIG. 19R

541/101
TGT GAT CCA GTC TTA CAT TCA GTA TGG TAA ACA GAG AAA ACA GGC TTT TGA AGA
 C   D   P   V   L   H   S   V   W   *   T   E   K   T   G   F   *   R
 V   I   Q   S   Y   I   F   S   K   N   R   E   K   Q   R   L   L   E
 *   S   S   V   T   Y   *   V   G   Y   *   R   K   N   A   F   E   N
                                        571/191
601/201
ATT GCG AGA TGA TTT GGT TGA GTT AAG TAA ATA TTC GAG AAA TAT TGT TAA GAA
 I   A   R   *   F   G   *   V   K   *   I   F   E   K   Y   C   *   E
 L   R   D   D   L   V   E   L   S   K   Y   S   R   N   I   V   K   K
 *   E   M   I   W   L   *   V   K   V   N   I   R   E   I   L   L   R
                                        631/211
661/221
ATT TCT CAT GTA TGG AAG TAA AAT CAG AAG TTT TAA AGG CCA
 I   S   H   V   W   K   *   N   Q   K   F   *   R   P
 F   L   M   Y   G   S   K   T   R   S   F   L   K   A
 C   E   M   *   V   E   V   K   *   E   V   L   K   T
                                        691/231
ATT TCT CAT GTA TGG AAG TAA AAT CAG AAG TTT TAA AGG CCA
ATC CGT GGA GTA CGC ATA CAA TGA
 I   R   G   V   R   I   Q   *
 S   V   E   Y   A   Y   N   D
 P   S   W   S   T   H   T   T
721/241
CGT GAG GAA GAT GCT GCG GCA TGC GGA AGC CAT CGT GGA GTA CGC ATA CAA TGA
 R   E   E   D   A   A   A   C   G   S   H   R   G   V   R   I   Q   *
 V   R   K   M   L   R   H   A   E   A   I   V   E   Y   A   Y   N   D
 *   G   R   C   C   G   K   H   R   K   P   S   W   S   T   H   T   T
           751/251

FIG. 19C

```
781/261
CAA AGC CAT TTT GGA GCA GAG GAA CAT GCT GAC GGA AGA GCT CTA TGG GAA CAC ATT TCA
 Q   S   H   F   G   A   E   E   H   A   D   G   R   A   L   W   E   H   I   S
 K   A   I   L   E   Q   R   N   H   C   *   T   E   E   K   S   H   G   T   F   Q
                                        811/271
841/281
GCT TTA CAA CTC AGC AGA TCA CCG AAC AGT GTT AGA GGT ACA GCC AGA AAA
 A   L   Q   L   S   R   S   P   N   S   V   R   G   T   A   R   K
 L   Y   K   S   A   D   H   R   T   E   L   *   E   V   Q   P   E   K   N
 F   T   Q   V   Q   I   T   E   L   W   T   K   *   R   Y   S   Q   K
                    901/301                                871/291
ATT AGA ACT TAT TAT GGA TGA AAT GAA ACA GAT TCT AAC TCC AAT GGC CCA AAA GGA AGC
 I   R   T   Y   Y   G   *   N   E   T   D   S   N   S   N   G   P   K   G   S
 L   E   L   I   L   W   M   K   *   H   R   I   L   T   P   M   A   Q   K   E   A
 *   N   L   L   *   D   E   M   K   N   R   F   *   L   Q   W   P   K   R   K   L
                                                931/311
961/321
TCT GAT TAA GCA CTC ATT GGT GCA TAA AGT AAG TAC CTA CCT GGC CTA CCT GGT CTA CCT
 S   D   *   A   L   I   G   A   *   S   K   V   P   Y   L   P   G   L   P   G   L   P
 C   D   *   A   L   I   G   V   C   I   K   *   S   H   P   A   P   P
 V   I   K   H   S   L   V   C   I   K   V   S   T   F   L   P   M   A   P   P
         1021/341                                 991/331
CAA ACT CAG ATC AGA AAT GAT TGA AGC CAT CCG CGA GGC CAT GGT GTA GGT ACA CAC
 Q   T   Q   I   R   N   D   *   S   H   P   R   E   A   M   V   *   V   T   H
 K   L   R   S   E   M   I   E   A   I   R   E   K   P   W   C   R   Y   T
 N   *   D   Q   K   *   L   K   P   S   A   K   N   H   G   V   G   T   H   T
 1051/351
```

FIG. 19D

```
1081/361
ACA CGA TGG CCC CAG AGT GGC CAT GCA CTG CCA CTG CAC GCC CAA GGA CAG GAA
 T   R   W   P   Q   S   G   H   A   L   P   L   H   A   Q   G   Q   E
                                        1111/371
                                CCT GTG GCA TGG CAC GCC CAA GGA CAG GAA
                                 P   V   A   W   H   A   Q   G   Q   E
                                 L   W   H   G   T   P   K   D   R   K
                                 C   G   M   A   R   P   R   T   G   K
1141/381
AGT GAT TGT GAA AAC AAT GAA GAC TTA TGT TGA AAA GGT GGC TAA ATA CTC CCA
 S   D   C   E   N   N   E   D   L   C   *   K   G   G   *   W   P   L   P   H
                                        1171/391
                                            TGA AAA GGT GGC TAA ATA CTC CCA
                                             *   K   G   G   *   I   L   P
                                             E   K   V   A   N   T   S   P
                                             K   R   W   L   M   Y   S   Q   I
1201/401
TTT GGT TTT ACT GGC GGC ATT TGA TAT TGA TAC TAA GCT TGT GAA GCA GAT AAT
 F   G   F   T   G   G   I   *   Y   *   Y   *   A   C   E   A   D   N
                                        1231/411
                                            TGA TAC TAA GCT TGT GAA GCA GAT AAT
                                             *   Y   *   A   C   E   A   D   N
                                             L   L   V   K   Q   I   I
                                             C   I   L   S   R   *   S   *
1261/421
CAT ATC AGA AAT TAT CAG TTC ATT GCC TAG CAT AGT AAA TGA CAA ATA TGG AAG GAA GGT
 H   I   R   N   Y   Q   F   I   A   *   H   S   K   *   Q   I   W   K   E   G
                                        1291/431
                                                    CAT AGT AAA TGA CAA ATA TGG AAG GAA GGT
                                                     H   S   K   *   Q   I   W   K   E   G
                                                     I   V   N   D   K   Y   G   R   K   V
                                                     *   M   T   N   M   E   G   R   S
1321/441
CCT ATT GTA CTT ACT AAG CCC CAG AGA TCC TGC ACA TAC AGT ACG AGA AAT CAT TGA AGT
 P   I   V   L   T   K   P   Q   R   S   C   T   Y   S   T   R   N   H   *   S
                                        1351/451
                                                        TAC AGT ACG AGA AAT CAT TGA AGT
                                                         Y   S   T   R   N   H   *   S
                                                         T   V   R   E   I   I   E   V
                                                         L   *   Y   E   K   S   L   K   P
```

FIG. 19E

```
1381/461
TCT GCA AAA AGG AGA TGG AAA TGC ACA CAG TAA GAA AGA TAC AGA GGT CCG CAG ACG GGA
 S   A   K   R   R   W   K   C   T   Q   *   E   R   Y   R   G   P   Q   T   G
 L   Q   K   G   D   G   N   A   H   T   V   K   D   T   E   V   R   R   R   E
 C   K   E   M   E   M   I   T   S   K   R   K   I   Q   R   S   A   D   G   S
1441/481
GCT CCT AGA ATC CAT TTC TCC AGC TTT GTT AAG CTA CCT GCA AGA ACA CGC CCA AGA AGT
 A   P   R   I   H   F   S   S   F   V   K   L   P   A   R   T   R   P   R   S
 L   L   E   S   I   S   P   A   L   C   *   T   C   K   N   T   A   Q   E   V
 S   *   N   P   F   L   Q   L   C   V   S   Y   L   Q   E   H   A   P   K   *
1501/501
GGT GCT AGA TAA GTC TGC GTG TGT GGT GGT TGA CAT TCT GGG ATC TGC CAC TGG AGA GAT
 G   A   R   *   V   C   V   C   G   G   *   H   S   G   I   C   H   W   R   D
 V   L   D   K   S   A   C   V   V   V   D   I   L   G   S   A   T   G   E   T
 C   *   I   S   L   R   V   C   W   C   L   T   F   W   D   L   P   L   E   *
1561/521
CCT TCA GCC TAC CAT GAA TGC CAT CGC CAG CTT GGC AGC AAC AGG ACT GCA TCC TGG TGG
 P   S   A   Y   H   E   C   H   R   Q   L   G   S   N   R   T   A   S   W   W
 R   Q   P   T   M   N   A   I   A   S   L   A   A   T   G   L   H   P   G   G
 L   S   P   *   *   M   P   S   P   A   W   Q   Q   Q   D   C   I   L   V   A
1591/531
CGT TGA CAT CGC CAG CTT GGC AGC AAC AGG ACT GCA TCC TGG TGG
```

```
1621/541
CAA GGA CGG AGA GCT TCA CAT TGC AGA ACA TCC TGC AGA ACA TCT AGT TCT GAA GTG GTT
 Q   G   R   R   A   S   H   C   R   T   S   C   R   T   S   S   S   E   V   V
 K   D   G   E   L   H   I   A   E   H   P   A   G   H   L   V   F   K   W   L
 R   T   *   R   L   F   *   T   L   Q   N   I   L   Q   D   I   *   S   G   *

1681/561
AAT AGA CCA AGA TAA AAA GAT GAA AGA AAA TGG GAG AGA AGG TTG TTT TGC AAA AAC ACT
 N   R   P   R   *   K   D   E   R   K   W   E   R   R   L   F   C   K   N   T
 I   E   Q   D   K   K   M   K   E   N   G   E   E   R   L   F   A   K   T   L
 *   S   K   I   K   R   *   *   K   K   M   G   R   K   V   L   L   Q   K   H

1741/581
TGT AGA CCA TGT TGG TAT GAA CCT GAA GAA CCT GGC TAG TGT AAA TCG AGG TGC CAT
 C   R   P   C   W   Y   E   P   E   E   P   G   *   C   K   S   R   C   H
 V   E   H   V   G   M   N   L   K   N   L   A   S   V   N   R   G   A   I
 *   S   T   W   *   V   *   T   *   R   T   W   L   V   *   I   E   V   P   L

1801/611
TAT TCT TTC TAG CCT CCT CCA GAG TTG TGA CCT GGA AGT TGC AAA CAA AGT CAA AGC TGC
 Y   S   F   *   P   P   P   E   L   *   P   G   S   C   K   Q   S   Q   S   C
 I   L   S   L   L   P   P   R   V   V   P   G   S   C   K   Q   S   K   V   K   A   A
 F   F   *   S   S   L   Q   S   C   D   L   E   V   L   Q   T   K   S   K   L   H

1861/621
ACT GAA AAG CTT GAT TCC TAC ACT GGA AAA AAC CAA AAG CAC CAG CAA AGG AAT AGA AAT
 T   E   K   L   D   S   Y   T   G   K   N   Q   K   H   Q   Q   R   N   R   N
 L   K   S   L   I   P   T   L   E   K   T   K   S   T   S   K   E   *   E   I
 *   K   A   *   F   L   H   W   K   K   P   K   A   P   A   K   E   I   K   F
```

```
1921/641
TCT ACT TGA AAA ACT GAG CAC ATA GGT GGA AAG AGT TAA GAG CAA GAT GGA ATG ATT TTT
 S   T   *   K   T   E   H   I   G   G   K   S   *   E   Q   D   G   M   I   F
         L   K   L   *   A   H   I   *   V   E   R   V   K   S   R   W   *   F   F
             Y   N   *   S   S   R   Y   R   W   K   E   L   R   A   M   E   D   F
1981/661                                                            1951/651
TCT CTT CTC TGT TCT GTT TCC CAA TGC AGA GAA GGG GTA GGG TCC ACC ATA CTC GTA
 S   L   L   C   S   V   S   Q   C   R   E   G   V   G   S   T   I   L   V
     L   F   L   C   V   L   P   N   A   E   K   G   *   R   V   P   Y   W

```
                                                                              50
Pile.1 (Nca3)    MCFLLETSAS PRSKLSKDFK PQFTLLSSVT KKKKKKVRPH NFQCIISLNF
Pile.1 (Uth1)    .......... .......... .......... .......... ..........
Pile.1 (Sag1)    .......... .......... .......... .......... ..........
Consensus        ---------- ---------- ---------- ---------- ----------

100
Pile.1 (Nca3)    VYFLFIHSFL FEYNQLLVLP LNKNLPSLNF .......... ..........
Pile.1 (Uth1)    .......... .......... .......... ....MKISA ALILSSLSSV
Pile.1 (Sag1)    .......... .......... SRNSSMKLSA LLALS..... ..........
Consensus        ---------- ---------- ---------- ---MK-S--- ----------

150
Pile.1 (Nca3)    AFSAPAPAPA DSHHEDHHKD EKPAV..... V TVTQYID... ..........
Pile.1 (Uth1)    ASTAVLAAPA VIHSDNHHIN DKRAV..... V TVTQYVNADG AVVIPAA...
Pile.1 (Sag1)    ALVSALPIVD VHQEDAHQH. .KRAVAYKYV YETVVVDSDG HTVTPAASEV
Consensus        A--------- ----H----- -K-AV----V --T------- ----------

200
Pile.1 (Nca3)    .......... .......SN AATSTVES.A ATTTL..... ..........
Pile.1 (Uth1)    .......... ...TTATSA AADGKVESVA AATTLSSTA LAANTSAAAS
Pile.1 (Sag1)    ATAATSALTT TSVLAPTSSA AAADSSASTA VSSAALAKNE KISDAAASAT
Consensus        ---------- -------S-- AA-------- ----L----- ----------

250
Pile.1 (Nca3)    ...SSSEKD TSEQKRDGGF QDGTVKC... .......... ..........
Pile.1 (Uth1)    SSSSSSSSSS SSSSVGSGDF EDGTISC... .......... ..........
Pile.1 (Sag1)    ASTSQGASSS SSSSSATSTL ESSSVSSSSE EAAPTSTVVS TSSATQSSAS
Consensus        ---------- -S-------- ---------- ---------- ----------
```

FIG. 22A

```
                    251
Pile.1 (Nca3)    ..........  ..........  ...SDFPSV  NGIVSLDWLG  FGGWASVMDM  DANTSSECKD
Pile.1 (Uth1)    ..........  ..........  ...SDFPSG  QGAVSLDWLG  LGGWASIMDM  NGNTATSCQD
Pile.1 (Sag1)    SATKSSTSST  SPSTSTSTST  SSTSSSSSSS  SSSSSSSSNT             DTSTGGSCKE
Consensus        ----------  ----------  -------S--  -S--------  ----S-----  ---T---C--
                                                                                       300

301
Pile.1 (Nca3)    GYYCSYACEP  GMSKTQWPSD  QPSDGKSVGG  LYCKNGYLYR  TNTDTSDLCS
Pile.1 (Uth1)    GYYCSYACSP  GYAKTQWPSE  QPSDGRSVGG  LYCKNGKLYR  SNTDTNSLCV
Pile.1 (Sag1)    GSYCSYSCQP  GMSKTQWPSD  QPSDGRSVGG  LLCKNGYLYR  SNTDADYCLE
Consensus        G-YCSY-C-P  G--KTQWPS-  QPSDG-SVGG  L-CKNG-LYR  -NTD---LC-
                                                                           350

351
Pile.1 (Nca3)    TDETSAKAIN  KKSDSIALCR  TDYPGSENMV  IPTVVDGGDS  QPISVVDEDT
Pile.1 (Uth1)    ECOGSAOAVN  KVSGGSIAICG  TDYPGSENMV  VPTVVGAGSS  QPINVIKEDS
Pile.1 (Sag1)    WGVEAAYVVS  KLSKGVAICR  TDYPGTENMV  IPTYVEGGSS  LPLTVVDDDT
Consensus        ----A----   K-S---A-C-  TDYPG-ENMV  -PT-V--G-S  -P--V---D-
                                                                           400

401
Pile.1 (Nca3)    YYQWQGKKTS  AQYYINNAGV  SAEDGCIWGT  SGSDVGNWAP  LVLGAGSTNG
Pile.1 (Uth1)    YYQWQGKKTS  AQYYVNNAGV  SVERGCIWGT  EGSGVGNWAP  VVLGAGYTDG
Pile.1 (Sag1)    YFTWEGKKTS  AQYYVNNPGV  SVEDGCIWGT  SGSGIGNWAP  LNFGAASTGG
Consensus        Y--W-GKKTS  AQYY-NN-GV  S--E-GCIWGT  -GS--GNWAP  ---GA--T-G
                                                                           450
```

FIG. 22B

```
              451
Pile.1 (Nca3)  ETYLSLIPNP NSNQAANFNV KIVASDG.AN VQGSCAYEDG SFTGDGSDGC
Pile.1 (Uth1)  ITYLSIIPNP NNKEAPNFNI KIVATDG.ST VNGACSYENG VYSGSGSDGC
Pile.1 (Sag1)  VTYLSLIPNP NNSDALNYNV KIVAADDSSN VIGECVYENG EFSG.GADGC
Consensus      -TYLS-IPNP N---A-N-N- KIVA-D---- V-G-C-YE-G ---G-G-DGC
Sun4           ....SLIPNP NNGNALNFNV KIVAADDSST VNGECIYENG SFSSGGSDGC 501         515                                    500
Pile.1 (Nca3)  TVSVLSGSAE FVFYZ
Pile.1 (Uth1)  TVSVTSGSAN FVFYZ
Pile.1 (Sag1)  TVSVTSGKAH FVLYN
Consensus      TVSV-SG-A- FV-Y-
Sun4           TVSVTAGKAK FVLY.
```

FIG. 22C

EIGHT REPEATS IN UTH4
```
193    LatDqFGcrFLQKkLE
231    LilDpFGnyLVdKicD
267    IsinqYGtrsLQKiID
310    LinDInGnhVIQKcIf
348    IstHkhGccVLQKiLs
384    LinDqFGnyIIQfiLD
422    LsclkFssnVVeKfIK
487    LirDnFGnyALQtlLD
```
 HYDROPHOBIC      CHARGED
FIG. 23

|          |                  |   |
|----------|------------------|---|
| UTH4     | LatDqFGCRFLQKkLE |   |
| YGL023   | LckDqHGCRFLQKqLD | 1 |
| PUMILIO  | FsqDqHGSRFIQQkLE |   |
| HUMAN    | FsqDqHGSRFIQLkLE |   |

|   |                  |   |
|---|------------------|---|
|   | LilDpFGNYLIQKiCD |   |
|   | LmtDsFGNYLIQKiLE | 2 |
|   | LmtDvFGNYVIQKfFE |   |
|   | LmrDvFGNYVIQKfFE |   |

|   |                  |   |
|---|------------------|---|
|   | IsiNqYGTRSLQKiID |   |
|   | IslNpHGTRALQKlIE | 3 |
|   | LalQmYGLRVIQKaLE |   |
|   | LalQmYGLRVIQKaLE |   |

|   |                  |   |
|---|------------------|---|
|   | LinDlNGNHVIQKcIF |   |
|   | LskDlNGNHVIQKcLQ | 4 |
|   | CvkDqNGNHVVQKcIE |   |
|   | CvkDqNGNHVVQKcIE |   |

|   |                  |   |
|---|------------------|---|
|   | IstHkHGCCVLQKlLS |   |
|   | IatHrHGCCVLQRcLD | 5 |
|   | LstHpYGCRVIQRiLE |   |
|   | LstHpYGCRVIQRiLE |   |

|   |                  |   |
|---|------------------|---|
|   | LinDqFGNYIIQFiLD |   |
|   | LtlDpFGNYVVQYiIT | 6 |
|   | LiqDqYGNYVIQHvLE |   |
|   | LvqDqYGNYVIQHvLE |   |

|   |                  |   |
|---|------------------|---|
|   | LscIkFSSNVVEKfIK |   |
|   | LsiHkFGSNVIEKiIK | 7 |
|   | LsqHkFASNVVEKcVT |   |
|   | VlsQhFASNVVEKcVT |   |

|   |                  |   |
|---|------------------|---|
|   | LirDnFGNYALQTlLD |   |
|   | LlnDsYGNYVLQTaLD | 8 |
|   | MmkDqYANYVVQKmID |   |
|   | MmkDqYANYVVQKmID |   |

FIG. 24

IDENTIFYING LIFESPAN-ALTERING AGENTS

RELATED APPLICATIONS

This application is a divisional of U.S. Ser. No. 09/323,433 filed Jun. 1, 1999, now U.S. Pat. No. 6,218,512, which is a divisional of U.S. Ser. No. 08/396,001, filed Feb. 28, 1995, now U.S. Pat. No. 5,919,618, which is a continuation-in-part of Serial Number PCT/US94/09351, filed Aug. 15, 1994, which is a continuation-in-part of U.S. Ser. No. 08/107,408, filed Aug. 16, 1993, now abandoned, the entire teachings of which are incorporated herein by reference.

GOVERNMENT SUPPORT

The invention was supported, in whole or in part, with U.S. Government support under Contract Number NIH-5R01-GM30454 and NIG-1R01-AG11119 awarded by the National Institutes of Health. The Government has certain rights in the invention.

BACKGROUND OF THE INVENTION

Aging is a process in which all individuals of a species undergo a progressive decline in vitality leading to death. In metazoans, aging at the level of the whole organism is clearly evident. Whether the aging of an organism is genetically programmed, or represents the effects of entropy over time is not clear. Consistent with the possibility of a genetic program are mutations which alter the aging process. In humans the genetic diseases progeria and Werner's syndrome cause premature aging in affected individuals. In the earthworm *C. elegans*, a gene, age-1, has been described which directly or indirectly affects the life span of the animal (Friedman, D. B. and Johnson, T. E., *Genetics* 18:75–86 (1988)). A further issue open to speculation is how the aging of the entire organism relates to the aging of individual cells and cell types within the organism.

That individual cells within mammals do senesce was demonstrated in the findings of Hayflick, who showed that primary human diploid fibroblasts (HDFs) would grow in culture for about 50 population doublings, and then all the cells in the population would stop dividing (Hayflick, L. and Moorhead, P. S., *Exp. Cell Res.* 25:585–621 (1961); Hayflick, L., *Exp. Cell Res.* 37:614–636 (1965)). Cells arrest in the G1 phase of the cell cycle and contain a 2N chromosomal complement (Cristofalo, V. J., et al., *Exp. Gerontol.* 24:367 (1989)). This in phase, or clonal, senescence of the HDFs is accompanied by a characteristic morphological change; cells enlarge as they senesce (Angello, J. C., et al., *J. Cell. Physiol.* 132:125–130 (1987) and Cristofalo, V. J. and Kritchevsky, D., *Med. Exp.* 19:313–320 (1969)). In fact, this direct correlation between cell size and senescence can be demonstrated by incubating young HDFs in low serum-medium, in which they enlarge, but do not leave the G1 phase of the cell cycle (Angello, J. C., et al., *J. Cell. Physiol.* 140:288–294 (1989)). When these cells are returned to medium containing adequate serum for cell division, their program of senescence has been advanced compared to smaller cells which have divided the same number of times.

Cell fusion studies between old and young HDFs indicate that senescence is dominant. In short term hybrids, initiation of DNA synthesis in the young nucleus is inhibited after the young cell has been fused to a senescent HDF (Norwood, T. H., et al., *Proc. Natl. Acad. Sci. USA* 71:2231 (1974)). In fact, injection of polyA+ RNA from the senescent HDF into the young cell inhibits DNA synthesis (Lumpkin, C. K., Jr., et al., *Science* 232:393 (1986)), suggesting that the senescent HDF activated a gene or genes that encoded dominant inhibitory proteins. In complementation studies that involve fusing various "immortal" cell lines, four genes were identified which were involved in immortalization (Pereira-Smith, O. M. and Smith, J. R., *Proc. Natl. Acad. Sci. USA* 785:6042 (1988)). The dominance of senescence appears to conflict with the view that shortening of telomeres, a phenomenon observed during passage of fibroblasts (Harley, C. B., et al., *Nature* 345:458 (1990)), causes senescence.

In several lower eukaryotes, senescence has been demonstrated and linked to changes in mitochondria. In Podospora, cell senescence is strongly associated with the excision and amplification of segments of mitochondrial DNA (Cummings, D. J., et al., *J. Mol. Biol.* 185:659–680 (1985) and Koll, F. et al., Plasmid 14:106–117 (1985)). In *Neurospora* (Bertrand J., et al., *Cell* 47:829–837 (1986)) and *Aspergillus* (Lazarus, C. M., et al., *Eur. J. Biochem* 106:663–641 (1989)), senescent cells also contain rearrangements in their mitochondrial DNA. In all of the above examples, the senescent phenotype is dominant and is inherited cytoplasmically.

In the budding yeast, *Saccharomyces cerevisiae*, cells divide asymmetrically, giving rise to a large mother cell and a small daughter cell. By micromanipulating the daughter away from the mother at each cell division, it was shown that the mother divided a fixed number of times, and then stopped (Mortimer, R. K. and Johnston, J. R., *Nature* 183:1751–1752 (1959)). Life span was thus defined by the number of divisions mother cells had undergone, and not by chronological time. Further, a number of cell divisions in the life span of the mother, while fixed (varying over a Gompertz distribution (Pohley, J.-J. *Mech. Ageing Dev.* 38:231–243 (1987)), could differ from strain to strain (ranging from about 15 to 30) (Egilmez, N. K. and Jazwinski, S. M., *J. Bacteriol.* 171:37–42 (1989)). Thus, senescence in budding yeast as in HDFs is not a stochastic process, but has some underlying genetic basis.

Senescence in yeast is like senescence in HDFs in other ways as well. Like HDFs, yeast mother cells have been shown to enlarge with age (Mortimer, R. K. and Johnston, J. R., *Nature* 183:1751–1752 (1959) and Egilmez, N. K., et al., *J. Gerontol. Biol. Sci.* 45:B9-17 (1990)). In addition to their large size, aging mother cells also divide more slowly than young cells (Egilmez, N. K. and Jazwinski, S. M., *J. Bacteriol.* 171:37–42 (1989)). A further analogy to HDFs is that the senescent phenotype is also dominant in yeast. Mating a young yeast cell to an old one generates a diploid with a limited potential for cell division (Muller, I., *J. Microbiol. Serol.* 51:1–10 (1985)). In addition, daughters of old mothers display elongated cycling times for the first few divisions after separation from the old mother (Egilmez, N. K. and Jazwinski, S. M., *J. Bacteriol.* 171:37–42 (1989)). Evidently, the senescence substance is inherited by the daughter cell and slowly degraded or diluted in subsequent cell cycles.

The senescence of yeast mother cells thus has similarities to what occurs in primary HDFs; however, there is one important difference. In yeast at each cell division the daughter cell has regained the capacity for a full life span, whether derived from a younger or older mother cell (Muller, I., *Arch. Mikrobiol.* 77:20–25 (1971)). This "resetting" in daughters may be intertwined with the mechanism that generates asymmetry at cell division. In any case, "resetting" argues against one category of hypothesis for aging; namely that aging results from the accumulation of errors in protein synthesis, the error catastrophe theory (Orgel, L. E. *Nature* 243:441 (1973)). Because daughter cells derived from old mothers have functional mitochondria (Muller, I. and Wolf, F., *Mol. Gen. Genet.* 160:231–234 (1978)), this resetting also shows that senescence is not due to rearrangements in the mitochondrial genome.

By varying the growth rate of cells, it was demonstrated that the key parameter in determining the life span in yeast is number of divisions, and not chronological time (Muller, I., et al., *Mech. Ageing Dev.* 12:47–52 (1980)). This finding led to the idea that senescence could be due to an accumulation of bud scars in mother cells. Bud scars are deposits of chitin that stay with the mother cell after each cell division (Cabib, E., et al., *Curr. Top. Cell. Regul.* 8:1–32 (1974), and Pringle, J. R., et al., *Meth. Cell Biol.* 31:357–435 (1989)). Several lines of evidence have argued against the idea that bud scars cause aging. First, varying the surface to volume ratio of isogenic yeast strains by varying their ploidy did not affect life span (Muller, I., *Arch. Mikrobiol.* 77:20–25 (1971)). Second, increasing the surface area by mating an old cell to a young one did not endow the diploid with an increased potential for division (Muller, I., *J. Microbiol. Serol.* 51:1–10 (1985)). Third, induction of chitin synthesis and deposition in the cell wall did not decrease the life span of cells (Egilmez, N. K. and Jazwinski, S. M., *J. Bacteriol.* 171:37–42 (1989)). Thus, senescence in yeast has gross features similar to the aging process in mammalian cells. It is therefore reasonable to speculate that the molecular mechanisms of aging might be similar in yeast and mammalian cells, particularly in light of striking parallels in basic cellular mechanisms in yeast and mammalian cells. In the field of transcription, for example, there has emerged strong mechanistic similarities in the function of transcription factors: the yeast and mammalian TATA box binding factor TFID, are interchangeable in the basal in vitro transcription reaction (Buratowski, S., et al., *Nature* 334:37–42 (1988)). Further, yeast and certain mammalian transcriptional activators will function normally in the heterologous host cells (see Guarente, L., et al., *Cell* 52:303–305 (1988) for review). Therefore, further study of aging in yeast cells may yield information concerning genes which are involved in senescence, and ultimately may shed light on the aging process in mammalian cells.

SUMMARY OF THE INVENTION

The present invention pertains to life span-determining genes which affect senescence in eukaryotic cells, such as budding yeast, and to mutated forms of the life span-determining genes. The genes of the present invention affect senescence either by contributing to aging or by conferring an extended life span upon the eukaryotic cell. Mutated genes of the present invention differ from wild type or naturally-occuring genes in that there is an addition, deletion, substitution or other alteration of the nucleic acid sequence, with the result that the encoded protein differs from the protein encoded by the non-mutated (wild-type) gene in at least one amino acid.

As described herein, it was discovered that the SIR4 gene (silent information regulator) contributes to extended life span: when the SIR4 gene is deleted, the resulting mutant yeast cells have a significantly shorter life span than yeast cells which contain the SIR4 gene. However, when mutant yeast cells are generated by a specific mutation in the SIR4 gene, the resultant mutant cells have a life span that is significantly longer than the life span of the non-mutant strain. The mutation is an amber mutation that removes 121 residues from the 1358 residue SIR4 protein.

It has also been discovered that the UTH4 gene affects senescence in a manner similar to that of SIR4. That is, a particular mutation in the UTH4 gene confers extended life span on mutant yeast cells.

As further described herein, it was discovered that the UTH1 gene effects senescence by contributing to the aging process. In particular, deletion of the UTH1 gene confers extended life span on the mutant yeast cell compared with the life span exhibited by yeast cells which contain the UTH1 gene.

Additional genes have been identified which show strong homology to the UTH4 and UTH1 genes. In particular, the yeast YGL023 and Drosophila PUMMILIO gene, as well as the human D43951 and D13645 genes, show strong homology to UTH4. The yeast NCA3 gene and the SAG1 gene show strong homology to the UTH1 gene. Deletion of either the NCA3 or SAG1 gene result in shortened yeast cell life span compared with wild-type (non-deleted) yeast cells. This indicates that NCA3 and SAG1 are genes which contribute to extended life span in yeast.

As a result of these discoveries, methods of isolating mutant yeast cells with increased life span, and the mutant yeast cells isolated by these methods, are now available. Also available are methods to identify agents which enhance the life span of yeast cells; methods to isolate genes involved in senescence, as well as the genes isolated thereby, and the proteins encoded by the genes.

As described in detail below, the current invention comprises several methods of isolating yeast cells with increased life spans (a life span longer than the known life span of the non-mutagenized yeast strain). In each method, a sample of yeast cells from a budding yeast strain, for which the life span is known or has been calculated, is exposed to a mutagen, and then the mutagen-exposed yeast cells are cultured. In one embodiment of the current invention, mutant yeast cells are identified first by the related phenotype of starvation resistance. The yeast cells are plated on minimal medium, replica-plated on starvation medium, and grown. The plate with starvation medium is replica-plated to enriched medium; those colonies which grow are starvation resistant. The starvation-resistant colonies are then examined to isolate cells with longer life spans.

In a second embodiment, the cell surface of yeast cells are labelled with a fluorescent marker. New cells remain unlabelled. After a period of growth greater than the known life span of the yeast strain, the cells are subjected to fluorescence-activated cell sorting to isolate the fluorescent-labelled cells, which are then plated. Only those cells with longer life spans grow. In another embodiment, a temperature-sensitive budding yeast strain, in which the daughter cells die at the non-permissive temperature, is used. When cells from the temperature-sensitive strain are grown at the non-permissive temperature, they form microcolonies in which the number of cells in the microcolony is equivalent to the number of generations in the life span of the yeast strain. Larger microcolonies, which are comprised of cells with a longer life span, are identified. Cells with increased life spans, isolated by any of these methods, are also part of the current invention.

The current invention also comprises methods of identifying agents which increase life span. Cells from a budding yeast strain with a known life span are exposed to the agent to be tested; the cells are then cultured and examined to determine whether they have longer life spans, using any of the methods described above. The presence of cells having longer life spans is indicative of the ability of the agent to increase life span of the cells.

In addition, the current invention pertains to genes which are involved in senescence of organisms, including yeast, bacteria and vertebrates, particularly mammals. Genes can be isolated by complementation analysis. For example, a genomic DNA library is constructed for the organism of interest, and is transformed into a mutant yeast strain having a mutated gene which contributes to longer life span, such as a mutant SIR4 gene. The DNA from the organism of interest is then isolated from those transformants which have the usual life span (i.e., those cells from the mutant yeast strain which no longer have a longer life span).

Alternatively, genes which are homologous to and/or hybridize to a gene that is known to affect senescence, such as SIR4, can be identified and/or isolated. The isolated genes, and the proteins encoded by the genes, are also the subject of the current invention. The subject invention also relates to DNA which encodes a protein which affects senescence in an organism (eukaryotes such as yeast and mammals, including humans, and prokaryotes). This includes UTH1 (SEQ ID NO. 1), DNA which is homologous to and/or hybridizes to UTH1, such as NCA3 (SEQ ID NO. 11) and SAG1 (SEQ ID NO. 13), and DNA which encodes the same amino acid sequence as that encoded by UTH1, NCA3 or SAG1. This invention also relates to UTH1, NCA3 or SAG1 DNA which has been mutated, including mutations which cause non-expression of the encoded protein, DNA which is homologous to and/or hybridizes to the mutant UTH1, NCA3 or SAG1 DNA, and DNA which encodes the same amino acid sequence as that encoded by mutant UTH1, NCA3 or SAG1 DNA. This invention also includes proteins encoded by UTH1, NCA3 or SAG1 DNA and similar DNA sequences, as well as to proteins encoded by mutated UTH1, NCA3 or SAG1 DNA.

This invention also pertains to the UTH4 gene (SEQ ID NO. 3), DNA which is homologous to and/or hybridizes to UTH4, such as YGL023 (SEQ ID NO. 5), D43951 (SEQ ID NO. 7, FIGS. 18A–G) and D13645 (SEQ ID NO. 9), and DNA which encodes the same amino acid sequence as that encoded by UTH4, YGL023, D43951 or D13645. Also included is UTH4, YGL023, D43951 and D13645 DNA which has been mutated, including mutations which cause non-expression of the encoded protein or mutations which encode a stop codon, DNA which is homologous to and/or hybridizes to the mutant UTH4, YGL023, D43951 or D13645 DNA, and DNA which encodes the same amino acid sequence as that encoded by mutant UTH4, YGL023, D43951 or D13645 DNA. Further included are proteins encoded by UTH4, YGL023, D43951 and D13645 DNA and similar DNA sequences, as well as to proteins encoded by mutated UTH4, YGL023, D43951 or D13645 DNA.

Further, this invention includes DNA which is homologous to and/or hybridizes to SIR4 and DNA which encodes the same amino acid sequence as that encoded by SIR4. It also relates to mutant SIR4 DNA (which includes a stop codon at amino acid 1237 of the encoded protein), DNA which is homologous to and/or hybridizes to the mutant SIR4 DNA, and DNA which encodes the same amino acid sequence as that encoded by mutant SIR4 DNA. The present invention also relates to proteins encoded by mutant SIR4 DNA and the similar mutant SIR4 DNA sequences.

BRIEF DESCRIPTION OF THE FIGURES

FIGS. 15A–15B are a depiction of the nucleic acid sequence (SEQ ID NO. 1), and the encoded amino acid sequence (SEQ ID NO. 2), of the UTH1 gene.

FIGS. 16A–16I are a depiction of the nucleic acid sequence (SEQ ID NO. 3), and the encoded amino acid sequence (SEQ ID NO. 4), of the yeast UTH4 gene.

FIGS. 17A–17J are a depiction of the nucleic acid sequence (SEQ ID NO. 5), and the encoded amino acid sequence (SEQ ID NO. 6), of the yeast YGL023 gene.

FIGS. 18A–18M are a depiction of the nucleic acid sequence (SEQ ID NO. 7), and the encoded amino acid sequence (SEQ ID NO. 8), of the human D43951 gene.

FIGS. 19A–19H are a depiction of the nucleic acid sequence (SEQ ID NO. 9), and the encoded amino acid sequence (SEQ ID NO. 10), of the human D13645 gene.

FIGS. 20A–20B are a depiction of the nucleic acid sequence (SEQ ID NO. 11), and the encoded amino acid sequence (SEQ ID NO. 12), of the yeast NCA3 gene.

FIGS. 21A–21B are a depiction of the nucleic acid sequence (SEQ ID NO. 13), and the encoded amino acid sequence (SEQ ID NO. 14), of the yeast SAG1 gene.

FIGS. 22A–22C are an illustration of the consensus sequence (SEQ ID NO. 15) from the SUN domains of the UTH1, NCA3 and SAG1 genes (SEQ ID NO. 2, SEQ ID NO. 12 and SEQ ID NO. 14, respectively), as well as a comparison of the consensus sequence and a partial sequence of the SUN4 gene (SEQ ID NO. 16).

FIG. 23 depicts a comparison of the amino acid sequences of the eight repeat boxes of UTH4 (SEQ ID NOS. 17–24). Capital letters indicate conserved amino acids.

FIG. 24 depicts a comparison of the amino acid sequences of the eight repeat boxes of the UTH4, YGL023, Drosophila PUMILIO and human D43951 genes (SEQ ID NOS. 17–24, SEQ ID NOS. 25–32, SEQ ID NOS. 33–40, and SEQ ID NOS. 41–48, respectively). Capital letters indicate conserved amino acids.

DETAILED DESCRIPTION OF THE INVENTION

The present invention derives from the discovery that a particular gene is involved in senescence in yeast, and that a particular mutation in the gene causes an increase in life span of the yeast cells. As described below, longer-lived mutant yeast cells have been isolated in which the SIR4 gene has been mutated to generate a stop codon at amino acid 1237 of the encoded protein. As a result of this finding, it is now possible to identify and/or isolate yeast cells with longer life spans, as well as to identify agents which contribute to longer life span. It is further possible to isolate genes involved in (which have an effect on) senescence, as well as the proteins encoded by these genes, and genes encoding proteins that contribute to longer life span.

The following is a description of the discovery of a phenotype correlating with life span; the isolation of mutant yeast strains with longer life spans; the isolation and characterization of the mutant gene affecting life span; the requirements of other genes to lengthen life span; the effects of the mutant gene on telomeres; extension of life span expression of the carboxyl-terminus of the gene; a framework for relating silencing, aging, stress, and telomeres; methods of isolating strains with longer life spans; methods of identifying agents which affect life span; and methods of isolating genes involved in cellular senescence.

Identification of a Phenotype Correlating with Life Span

Because budding yeast cells divide asymmetrically into a large mother cell and a small daughter cell, the life span of any given mother cell in a particular colony can be measured. By visualizing growing cells in a microscope and micromanipulating away the daughter cell after each division, it is possible to follow a pedigree from each starting cell. The end of the life span for a given cell is indicated by a cessation of cell division. Life span is thus equated with the number of generations, or divisions, which give rise to daughter cells. The life span of a particular strain can be identified by the mean number of generations in several colonies. The chronological life span, therefore, is the approximate time necessary for one cell division, or for one generation to arise, multiplied by the number of divisions (generations) in the mean life span. A longer life span, as described herein, is measured as an increase in the mean life span of one strain as compared with the mean life span of a second strain.

Figure 1:
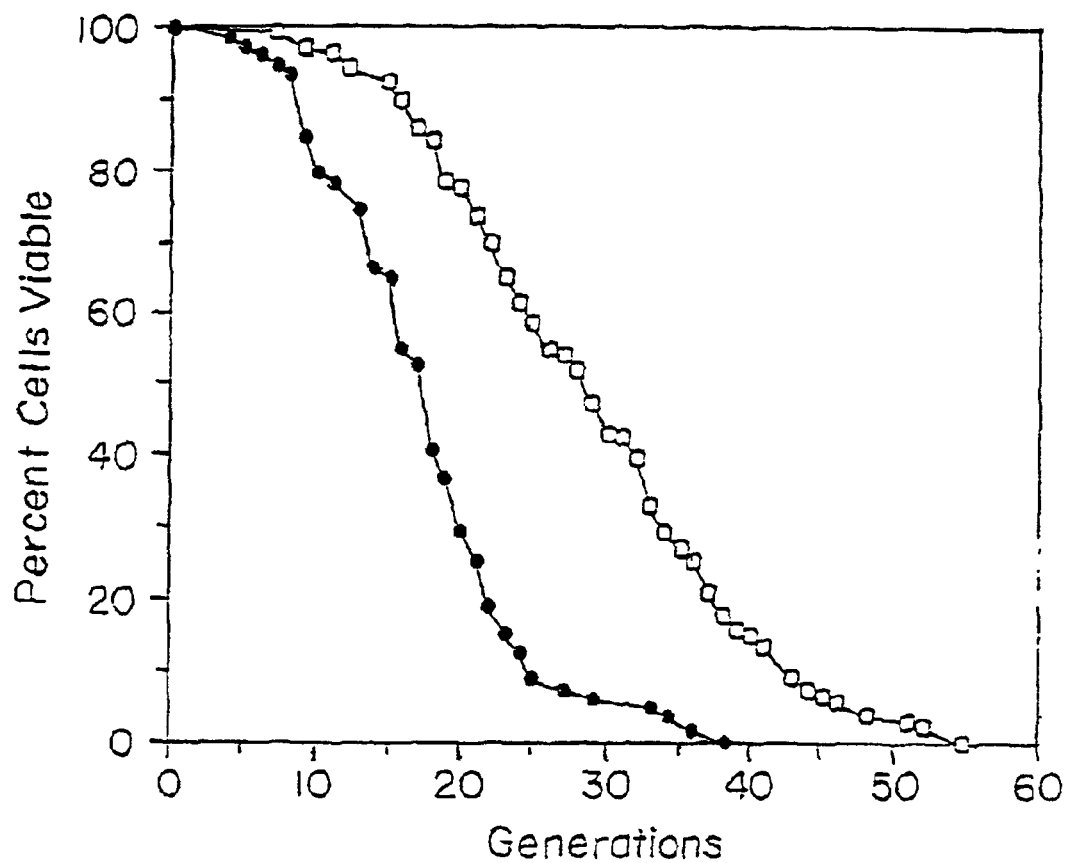
FIG. 1 is a graphic representation of the mortality curves for two strains of S. cerevisiae, BWG1-7A (closed symbols), and PSY142 (open symbols).
Figure 2A:
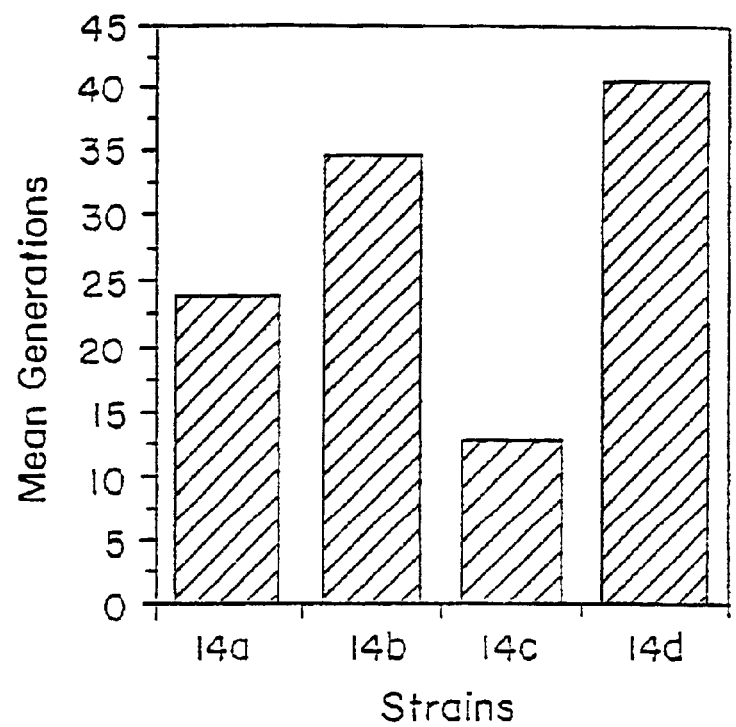
FIGS. 2A and 2B are a graphic representation of the mean life spans of the four strains in the tetrad BKx1-14.
Figure 2B:
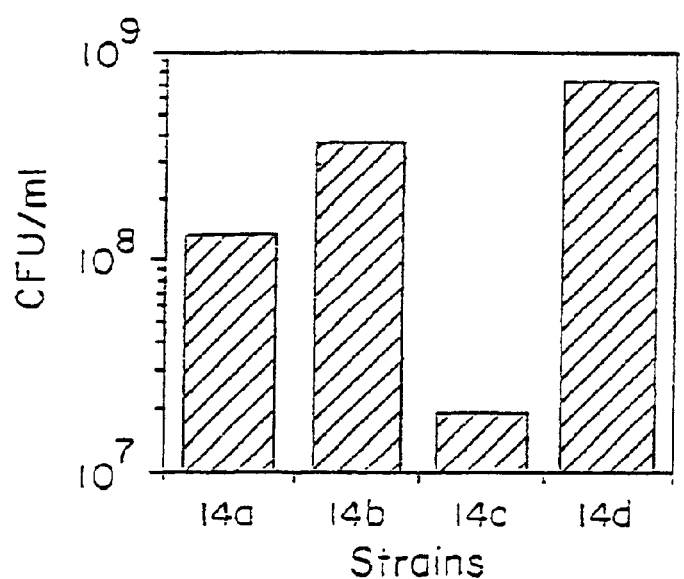
Figure 3:
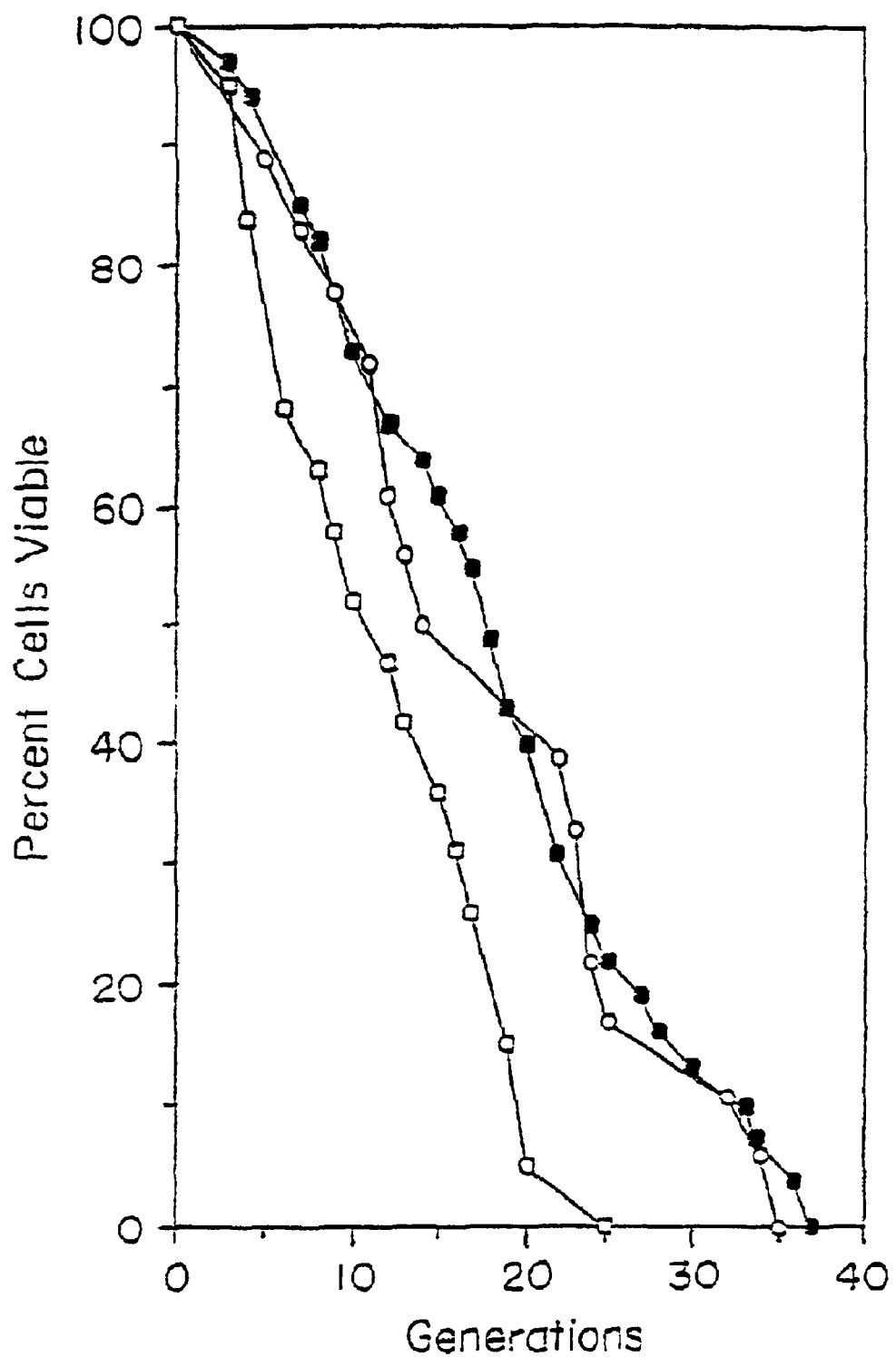
FIG. 3 is a graphic representation of the viability of the tetrad strains after 7 days of starvation.

To facilitate the identification of strains with altered life spans, a phenotype was sought which correlated with life span, yet which could be studied at the level of populations of cells (i.e., at a colony level). To this end, two parental strains were used, BWG1-7A (Guarente, L. et al., Cell 36:503–511 (1984)), and PSY142 (laboratory strain). These two strains had different mean life spans (18 generations for BWG1-7A, and 29 generations for PSY142), as shown in FIG. 1. Four strains of Saccharomyces cerevisiae were generated by crossing the parental strains BWG1-7A and PSY142 and sporulating the diploid. These four segregants of this cross, known collectively as the tetrad BKx1-14 strains and individually as 14a, 14b, 14c, and 14d, have varying life spans (see FIG. 2). When the tetrad strains were starved for nitrogen and carbon, it was discovered that starvation contributed to cell death, and that the rate of cell death when starved was inversely proportional to the life span of the particular strain. That is, longer-lived strains were more resistant to starvation-induced death than shorter-lived strains (see FIG. 3). Furthermore, strains with longer life spans yielded a greater recovery of viable cells after storage at 4° C. for 4.5 months.

Isolation of Longer-Lived Mutant Yeast Strains

To isolate longer-lived mutants, the shorter-lived strain 14c, which was relatively sensitive to starvation-induced cell death, was utilized. The yeast strain 14c has been deposited with the American Type Culture Collection, 12301 Parklawn Drive, Rockville, Md., 20852, USA, under the Budapest Treaty on the International Recognition of the Deposit of Microorganisms for the Purposes of Patent Procedure, on Aug. 13, 1993; the accession number is 74236. All restrictions on the availability to the public of the deposited material will be irrevocably removed upon the granting of the patent. 14c yeast cells were mutagenized with ethylmethane sulfonate (EMS) (approximately 60% of cells killed); colonies were plated on supplemented minimal plates (yeast nitrogen base, 2% glucose, and those amino acids and nucleotides required for the strain) and replica-plated to plates lacking nitrogen and carbon (the starvation plates) (contents identical to supplemented minimal, without nitrogen and carbon). After incubation of the starvation plates at 30° C. for five to ten days, the plates were replicated back to rich media plates (YPD) (1% yeast extract, 2% peptone, 2% dextrose). Most of the colonies consisted of dead cells, and thus did not grown on YPD; however, rare colonies contained living cells when plated back onto YPD (the "starvation resistant" colonies). Of 38,000 colonies, 39 were starvation resistant. Of these, eight had an extended life span (extended 20–55%). To determine the life span, cells were taken from logarithmically growing liquid cultures and plated at low density on complete medium. The plates were incubated at 30° C. for approximately three hours. At this time, daughter cells were isolated as buds that had emerged from mother cells, and moved with a Zeiss Micromanipulator to uninhabited regions of the plate. The life spans of these cells were determined by noting and removing all subsequent daughters they generated. The plates were incubated at 30° C. during working hours and shifted to 4° C. overnight. Life spans generated by this incubation schedule do not differ significantly from those generated by incubating cells continuously at 30° C. (data not shown).

To determine whether the mutants were dominant or recessive, the eight starvation resistant mutants were crossed with an isogeneic derivative of 14c, BKy5, with the opposite mating type, sporulated, and shown to segregate 2:2 for stress-related phenotypes in more than 10 tetrads each. Genetic analysis indicated that seven were recessive and one was dominant. Complementation analysis showed that the recessive mutations fell into three genes (UTH 1, 2, and 3).

Figure 4:
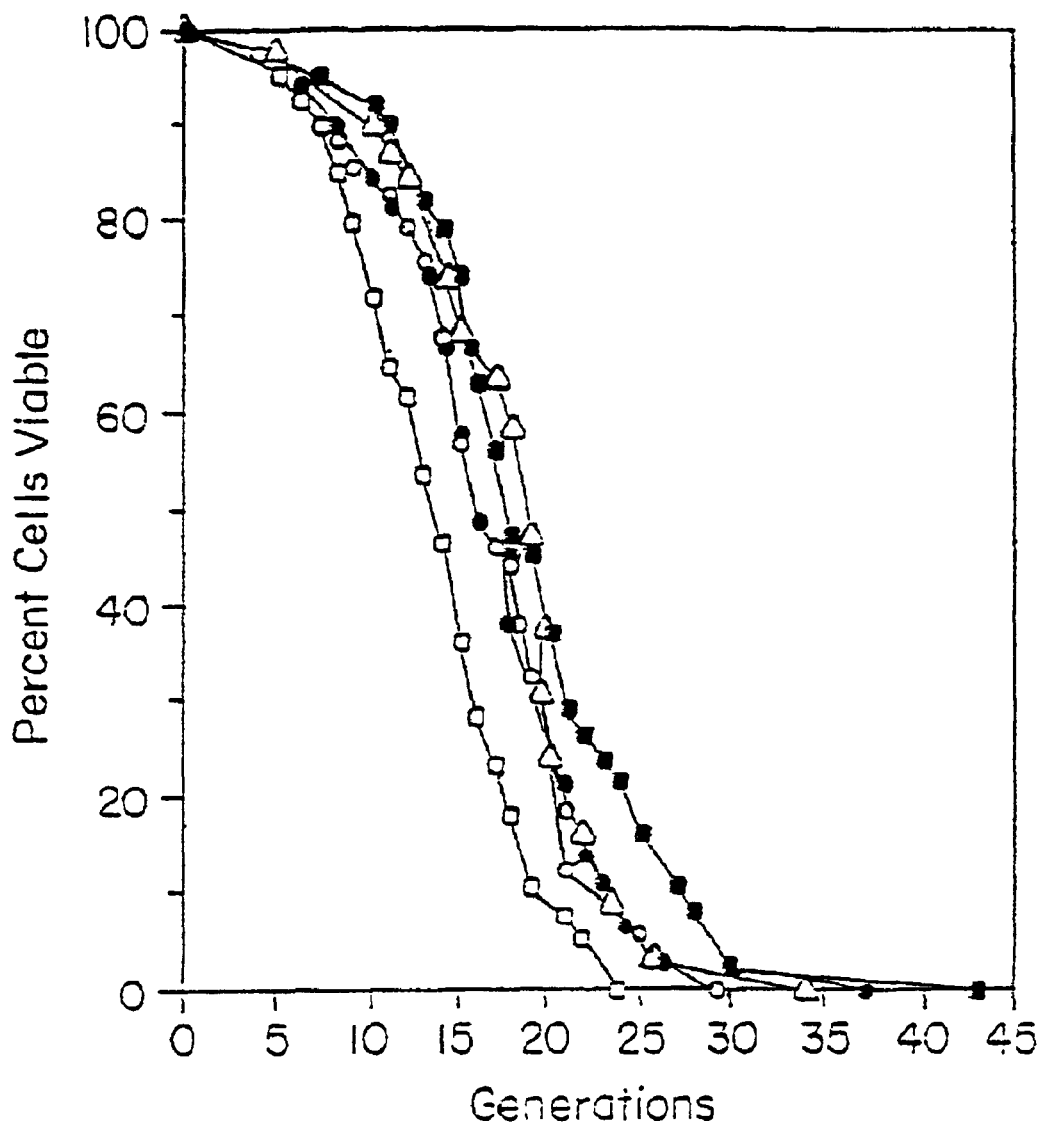
FIG. 4 is a graphic representation of mortality curves for UTH1 mutants. Sample sizes were 37 cells (uth1-324, closed circles), 38 cells (uth1-328, open triangles)), 38 cells (uth1-330, closed squares), 34 cells (uth1-342, open circles), and 40 cells (14c, open squares).
Figure 5:
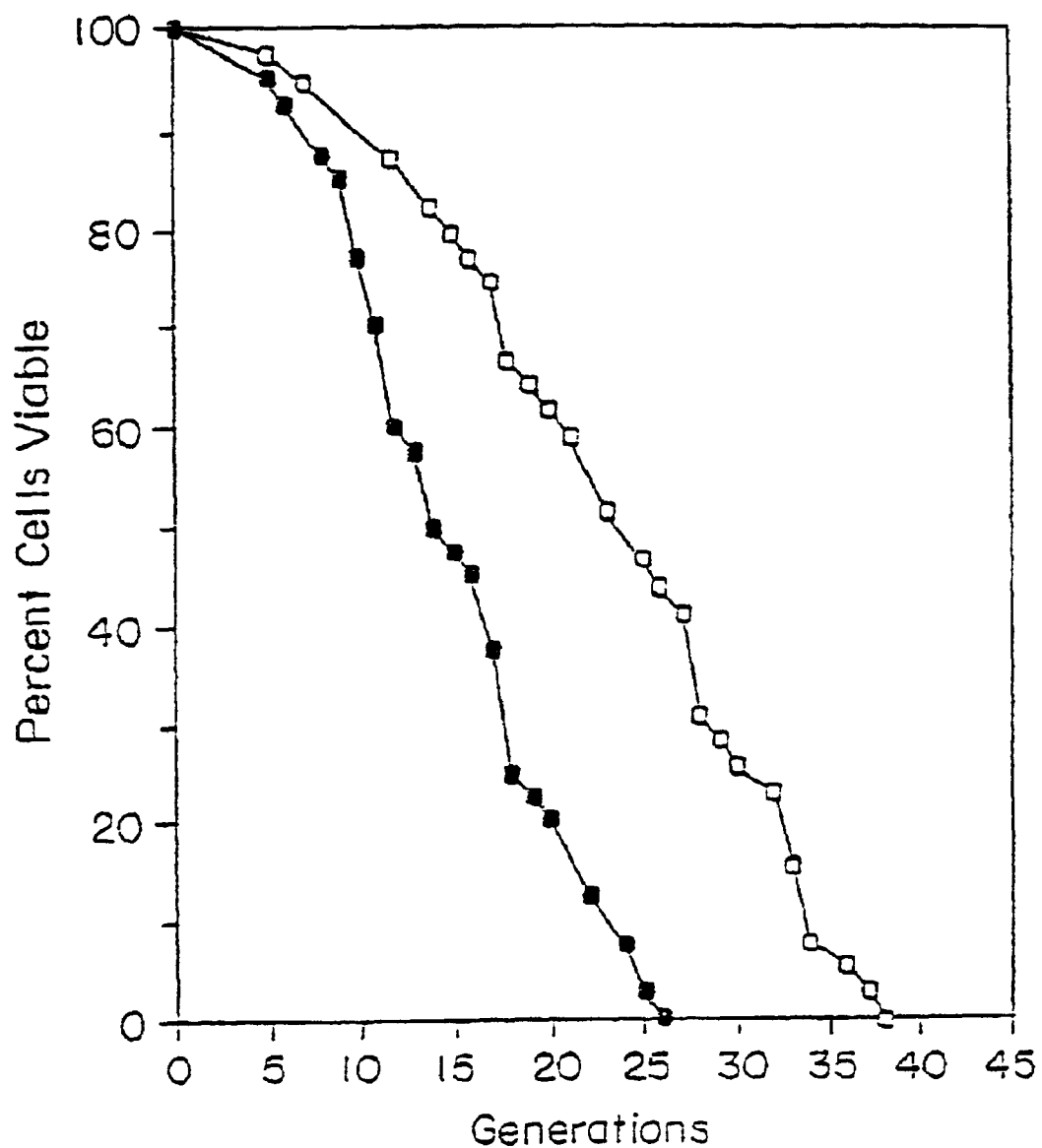
FIG. 5 is a graphic representation of mortality curves for UTH2 mutants. Sample sizes were 40 cells (uth2-42, closed figures), and 40 cells (14c, open figures).
Figure 6:
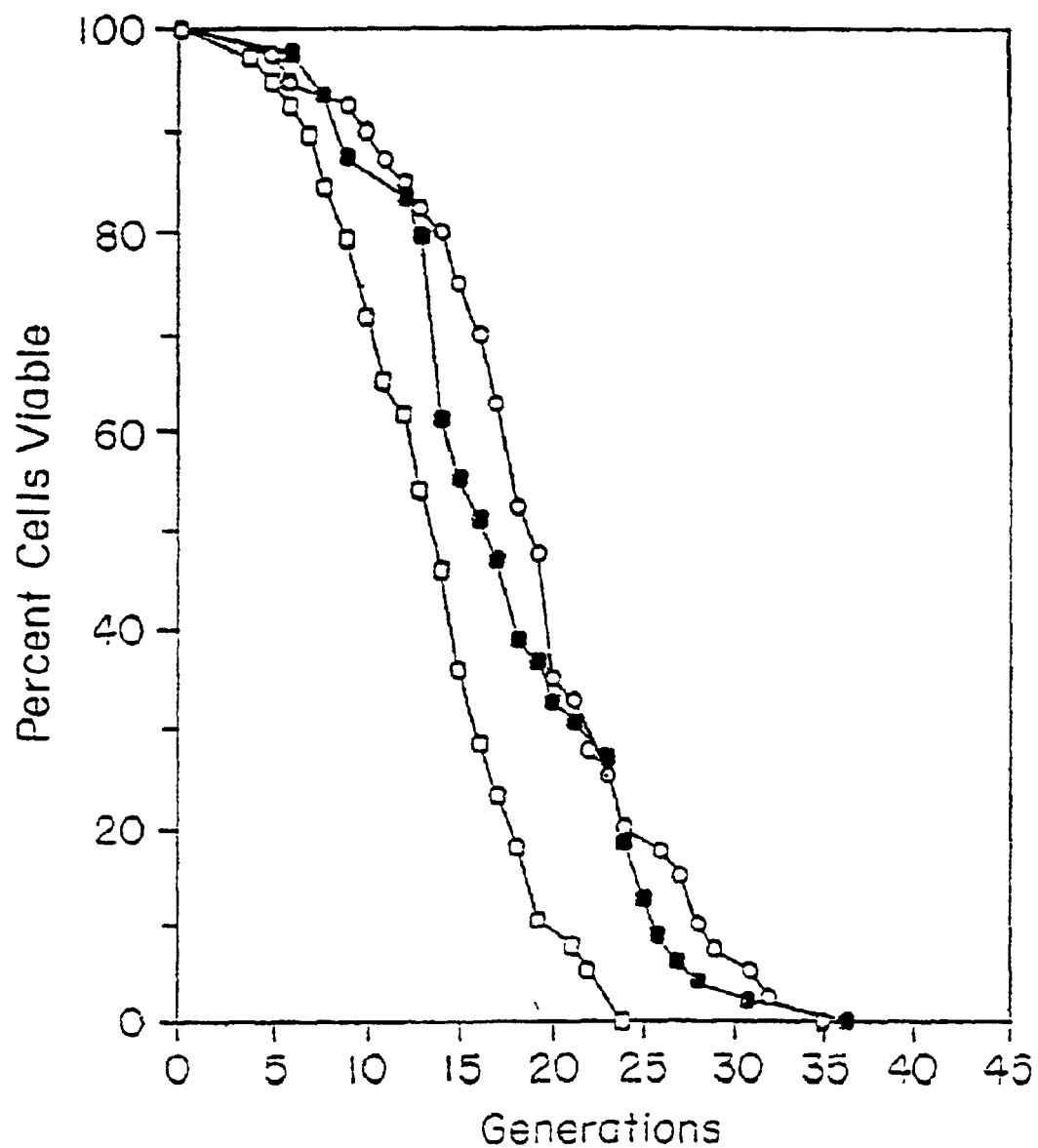
FIG. 6 is a graphic representation of mortality curves for UTH3 mutants. Sample sizes were 49 cells (uth3-26, closed squares), 40 cells (uth3-335, open circles), and 40 cells (14c, open squares).
Figure 7:
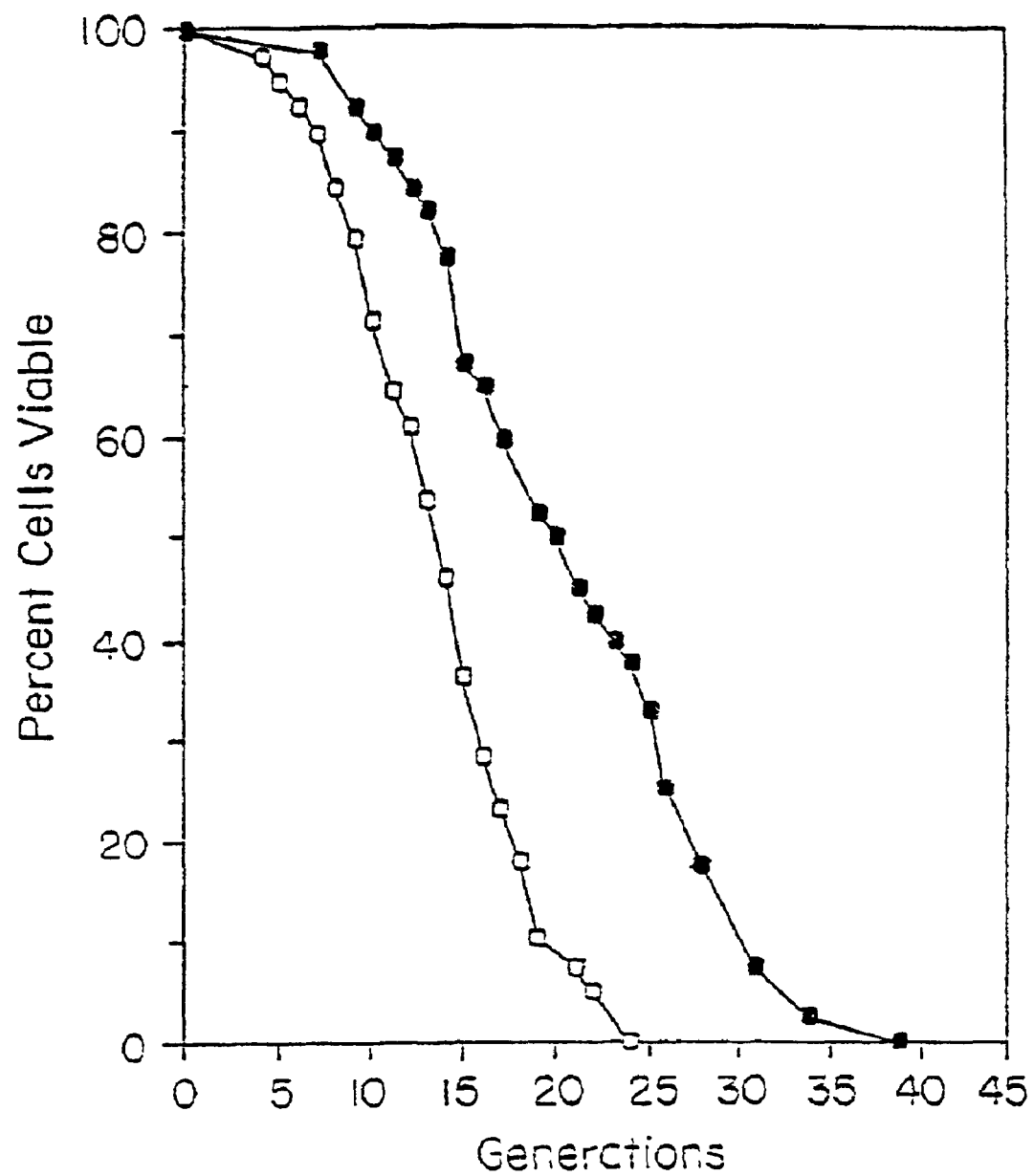
FIG. 7 is a graphic representation of mortality curves for UTH4 mutants. Sample sizes were 40 cells (uth4-326, closed squares), and 40 cells (14c, open squares).

The dominant mutation was not linked to representatives of any of these groups, and representatives of each group were not linked to each other. The dominant mutation was identified as a fourth gene (UTH4, SEQ ID NO. 3, FIGS. 16A–E). Mortality curves for each complementation group (UTH 1-4) are shown in FIG. 4 (UTH1), FIG. 5 (UTH2), FIG. 6 (UTH3), and FIG. 7 (UTH4). The differences in life span were statistically significant by a Wilcoxen signed rank test.

Several different phenotypes were examined. To determine starvation resistance, haploid cells were grown in rich media to log phase, collected by centrifugation, and resuspended in minimal sporulation media for a period of seven to nine days. After starvation, cells were again collected by centrifugation and plated on rich media to measure colony forming units (cfu)/ml. Colonies could be assayed for ability to withstand starvation by utilizing sporulation plates instead of liquid culture. Saturation density was measured by suspending logarithmically growing cells in rich medium liquid culture at a density of $10^6$ cells/ml. Cultures were incubated for a period of five days with the number of cells/ml counted in a hemacytometer on a periodic basis. Control experiments indicated that the media was completely saturated after this time period. Heat shock resistance was determined by collecting logarithmically growing cells and plating them at a known concentration on rich media plates. The cells were heat-shocked at 55° C. for periods varying from five minutes to one hour. Plates were then incubated at 40° C. for three days and the number of colonies was counted. Growth on ethanol was measured by directly streaking a strain on either rich media containing ethanol or synthetic media supplemented with necessary nutrients and containing ethanol as the sole carbon source.

All eight mutants had phenotypes that were different from the parental 14c strain: better stress survival rate (resistance to nitrogen starvation); extended life span (as shown by more divisions); growth to a higher saturation density; heat shock resistance; enhanced growth on ethanol (a carbon source that induces the heat shock response in S. cerevisiae) (Plesset, Biochem. Biophys. Res. Comm. 108:1340–1345 (1982)); caffeine resistance; and paraquat sensitivity. In addition, one mutant, designated uth2-42, displayed two additional phenotypes: it mated poorly, and exhibited a pseudohyphal-like growth pattern. The latter phenotype has been observed in diploids that were starved for nitrogen (Gimeno, C. et al., Cell 68:1077–1090 (1992)). Sterility and pseudohyphal-like growth both cosegregated with stress tolerance. Moreover, in three complete tetrads it was found that a lengthened life span also cosegregated with the other mutant phenotypes.

Isolation and Characterization of Genes Affecting Life Span

Isolation of the UTH2 gene was conducted by the ability of UTH2 to restore mating to the uth2-42 strain, assayed by replica-plating transformants to a lawn of a tester strain of opposite mating type (CKy21). The uth2-42 mutant was transformed with a standard yeast genomic library, CT3, on a URA3 plasmid (Thompson, C., et al., Cell 73:1361–1375 (1993)), by standard methods (Guthrie, C. and G. Fink, Methods in Enzymology, 1991), and Ura+colonies which were resistant to paraquat were selected. Transformed colonies were tested for their ability to complement the mating detect in the uth2-42 mutant. Plates containing library-transformed colonies were replica-plated onto permissive plates containing a lawn of strain CKy21. Cells were incubated at room temperature for one day to allow mating and then were replica-plated to plates selective for diploid growth. Colonies were picked which clearly grew on the selective plates. Plasmids were recovered from these colonies by standard methods and re-transformed into uth2-42 mutant cells. One plasmid restored the mating efficiency of the uth2-42 mutant. This plasmid, pBK40, also conferred heat shock sensitivity and starvation sensitivity to uth2-42, making it a good candidate for the UTH2 gene. pBK40 contained an insert of about 8 kb.

A 1.6 kb fragment located entirely within the pBK40 library insert was random primed by manufacturer's protocol (U.S. Biochemical), and used to probe a panel of lambda clones containing yeast DNA ((Riles, L. et al., Genetics 134:81–150 (1993)). Only one clone, the lambda clone that hybridized contained SIR4, showed a distinguishable signal.

SIR4 is a component of the yeast silencing complex that represses copies of MATα and MATα information and HML and HMR (Hartwell, L. H. J. Cell. Biol. 85:811–822 (1980); Laurenson, P. and J. Rine, Microbiol Rev. 56:543–560 (1992); Rine, J. and I. Herskowitz, Genetics 116:9–22 (1987)). Restriction mapping of pBK40 indicated that it contained SIR4 and at least 1 kb of flanking DNA to either side. To determine linkage, the insert was transferred to a LEU2-containing integrating vector and targeted to the SIR4 locus in BKy5. This integrant (BKy30) was mated with uth2-42 (containing pBK40 to allow mating), and after eviction of pBK40, the diploid sporulated. Thirteen of thirteen tetrads contained 2 Leu+, fertile:2 Leu−, sterile segregants, showing that SIR4 is tightly linked to the uth2-42 mutation. It was concluded that UTH2 was SIR4; therefore, uth2-42 was designated sir4-42.

The SIR4 gene is one of a series of genes (SIR1-4) involved in mating type switching. The SIR1-4 genes silence reserve copies of a and α information at the HML and HMR loci which are located to the left and right of the MAT mating type locus (see Rine, J. and Herskowitz, I., Genetics 116:9–22 (1987), for overview). The SIR1-4 genes also silence genes located at the telomeres of yeast chromosomes (Aparicio, O. M. et al., Cell 66(6): 1279–1287 (1991)). No other functions had previously been attributed to these genes.

Figure 8:
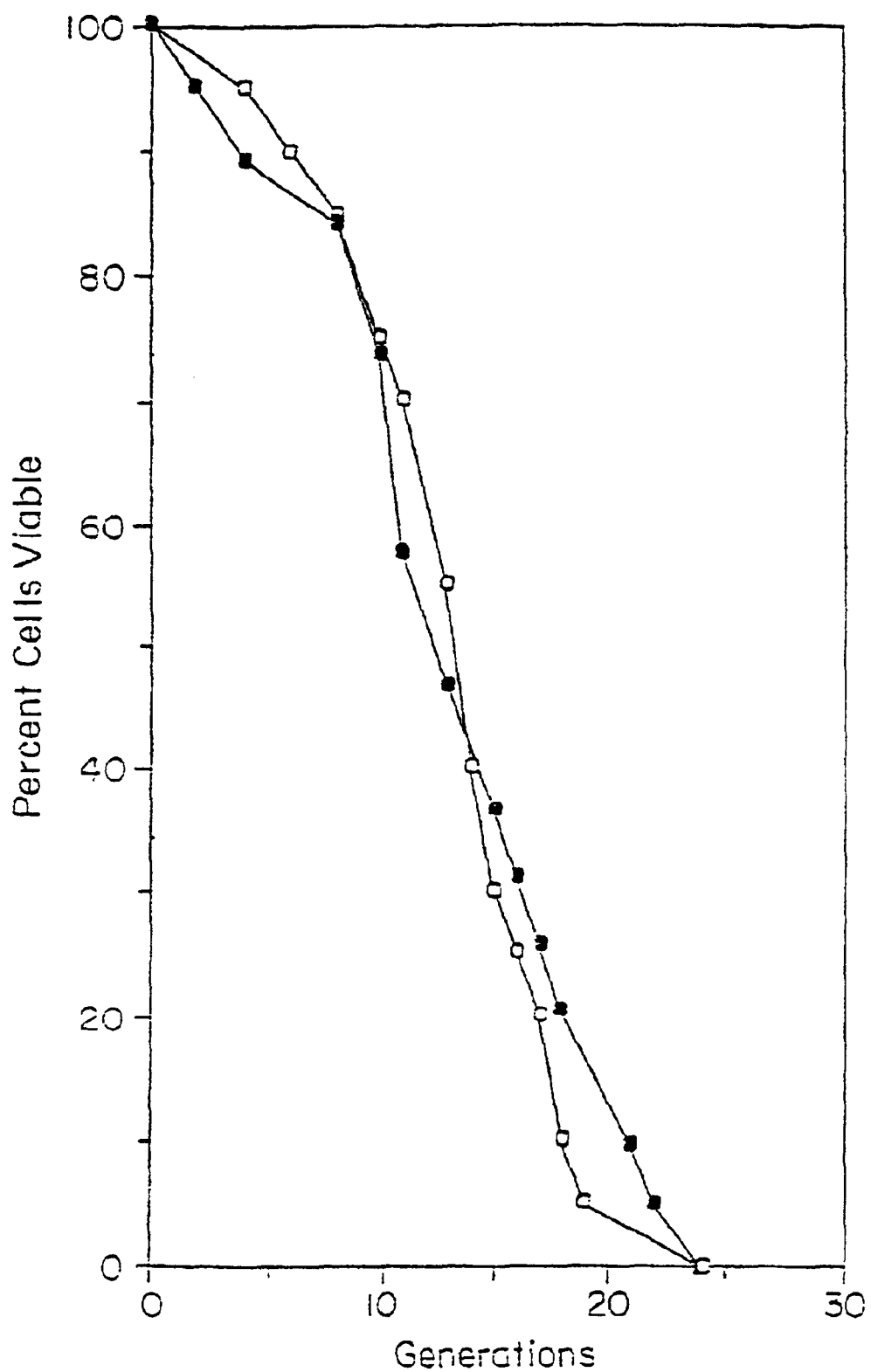
FIG. 8 is a graphic representation of the life span of haploid 14c (open squares) and diploid 14c (closed diamonds).

The SIR4 mutant is sterile because it expresses a and α information simultaneously. The effect of the SIR4 deletion was not simply because cells simultaneously expressed a and α information: the isogeneic diploid of 14c, BKy6, did not live longer than the haploid parents (14c and BKy5) (see FIG. 8). To generate BKy5, strain 14c was transformed with a (GAL-HO) plasmid and plated on galactose medium to induce mating type switching (Guthrie, C. and G. Fink, Methods in Enzymology, 1991). Colonies were tested by mating to CKy20 or CKy21 to determine their mating type; a MATa colony was picked and the GAL-HO plasmid was segregated using 5-FOA (Boeke, J. D. et al., Meth. Enzymol. 154:164–175 (1987)). This strain, BKy5, was mated to 14c and zygotes were isolated by micromanipulation to generate BKy6. To verify that BKy6 was a diploid, the strain was shown to be sporulation-competent.

Figure 9:
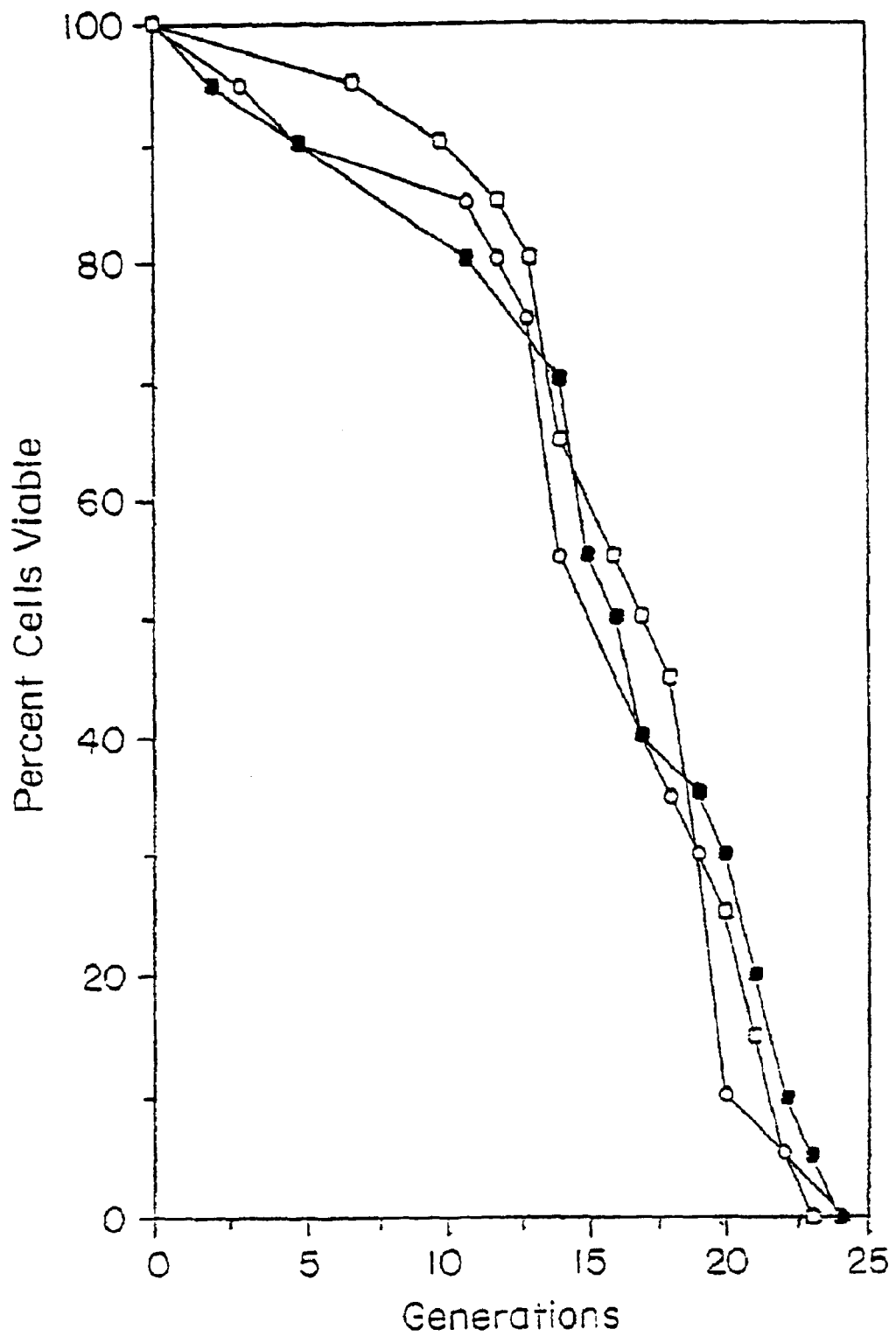
FIG. 9 is a graphic representation of the life span of 14c (open squares), 14c with a disruption in the STE4 gene (closed diamonds), and 14c with a disruption in the STE12 gene (closed circles).

Further, sterility per se was not the cause of the longer life span. Disrupting STE4 or STE12, genes involved in aspects of mating different than those of SIR4, did not affect life span (see FIG. 9). The disruption of STE4 was carried out as described in Whiteway, M. et al., Cell 56:467–477 (1989).

In addition, introduction of a plasmid which expressed MATα into BKy5 did not lengthen life span. The effects of sterility on life span are shown in Table 1, below. The maximum life span indicates the number of daughters produced by the oldest mother cell.

TABLE 1

THE EFFECTS OF STERILITY ON MEAN LIFE SPAN

| Strain | Sample Size | Mean Life Span | Maximum Life Span |
|---|---|---|---|
| BKy1-14c | 20 | 15.6 | 25 |
| BKy5 | 20 | 14.5 | 20 |
| BKy6 | 20 | 15.3 | 27 |
| BKy100 (ste4Δ) | 20 | 15.9 | 24 |
| BKy101 (ste12Δ) | 20 | 16.5 | 24 |
| BKy5 + Matα | 20 | 14.6 | 26 |

Figure 10:
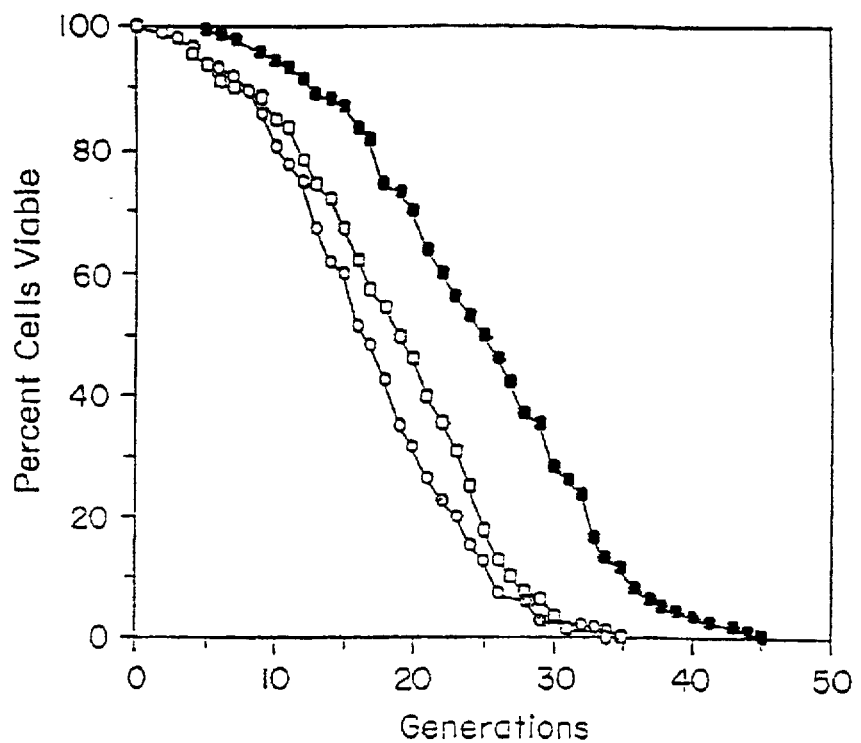
FIG. 10 is a graphic representation of mortality curves for 14c (SIR4, open squares), sir4-42 (closed diamonds), and BKy104 (sir4, open circles). Sample sizes were 139 cells (14c), 139 cells (sir4-42), and 136 cells (BKy104).

Because the stress and mating phenotypes of sir4-42 were recessive, it was surmised that the phenotype of a SIR4 null mutation would mimic that of sir4-42. The entire SIR4 gene was deleted in 14c: the region from 153 base pairs 5' to SIR4 through the entire open reading frame was deleted and replaced with the URA3 gene using the plasmid pAR59 provided by J. Broach (Marshall, M. et al, *Mol. Cell. Biol.* 7:4441–4452 (1987)). The sir4 deletion was confirmed by southern analysis. The resultant deleted strain, BKy104, was indeed stress tolerant and sterile (data not shown). Importantly, however, it did not have a lengthened life span; in fact, the deletion shortened life span by a small, but statistically significant, degree (see FIG. 10).

Figure 11:
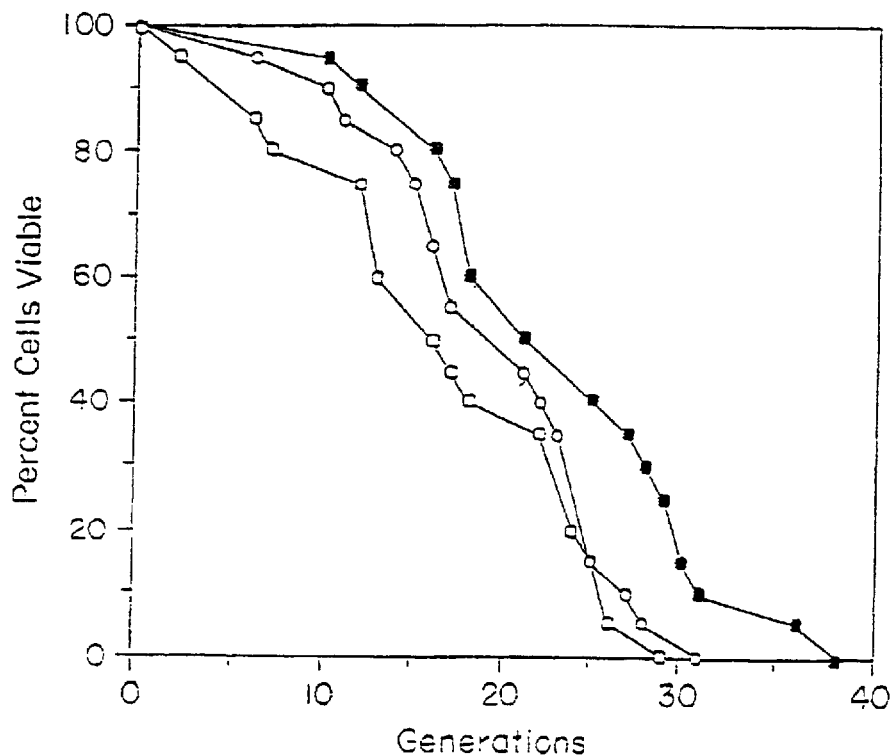
FIG. 11 is a graphic representation of mortality curves for 14c (SIR4, open squares), sir4-42 (sir4, closed diamonds), and BKy109 (sir4-42+SIR4, open circles). Sample sizes were 20 cells for all strains.

These data suggested that the effect of sir4-42 on life span, unlike its effects on stress and mating, might be due to a gain of function. To test this, it was investigated whether the sir4-42 allele was dominant to SIR4 for the phenotype of lengthened life span. The wild type SIR4 was transferred to an integrating vector and targeted to URA3 in the sir4-42 mutant. The integration plasmids were generated by subcloning the entire library insert containing SIR4 from pBK40 into pRS305 or pRS306 by a NotI SalI double digest (Sikorski, R. S. and P. Hieter, *Genetics* 122:19–27 (1989)). Integration was directed to the URA3 locus by a StuI digest, and was verified by Southern analysis. The resulting SIR4-sir4-42 haploid (BKy109) was stress sensitive and mated efficiently, as expected. However, the life span of this strain was intermediate between the SIR4 parent, 14c, and the sir4-42 mutant, as shown in FIG. 11. Statistical analysis determined that the mean life span of BKy109 was significantly different from the means of both sir4-42 and 14c. The sir4-42 mutation therefore is semi-dominant with respect to life span.

As a second test for dominance, mating was used to construct isogenic diploids, SIR4/SIR4 (BKy6), SIR4/sir4-42 (BKy17), and sir4-42/sir4-42 (BKy28) (using the SIR4 plasmid, pBK40, to permit mating in sir4-42 mutants). BKy19 was generating by mating the sir4-42 mutant containing pBK40 to 14c and subsequently removing the plasmid with 5-FOA. BKy17 was sporulated and a MATα sir4-42 segregant (BKy21) was used to generate the homozygous sir4-42 diploid (BKy28). BKy21 carrying pBK40 was mated to the sir4-42 mutant also carrying pBK40 and diploids were isolated. The homozygous diploids have life spans similar to their haploid parents, and the heterozygous diploid displayed a life span intermediate between the homozygotes (data not shown). These findings clearly show that the extended life span in the sir4-42 mutant is semi-dominant, and therefore, due to a gain of function mutation.

Gap repair was utilized to clone both the wild type SIR4 allele from 14c and the sir4-42 allele from the SIR4 mutant strain (Guthrie, C. and G. Fink, *Methods in Enzymology*, 1991). A SmaI AatII double digest was performed to remove the coding region of SIR4 from pBK40. The linear plasmid was gel purified and transformed into either 14c or the sir4-42 mutant. Ura+ colonies were picked and the plasmids were recovered by standard methods. Restriction digests were conducted to determine if the gap repair event was successful. To localize the mutation within SIR4, digests were conducted with AatII, SmaI, and SphI, all of which have one site in the SIR4 gene and another within the pBK40 insert, either 5' or 3' to SIR4. These linearized plasmids were transformed into sir4-42 and transformants were tested for their ability to complement the sir4-42-associated mating defect. This analysis localized the mutation to the region spanning codons 743 to the UAA stop at the end of the 1358 residue SIR4 open reading frame. The clone was shown to contain the mutation by a functional test in which it was transferred to an integrating vector, and targeted to LEU2 in strain BKy104 (Δsir4). Integration was directed to the LEU2 locus by a XcmI digest, and verified by Southern analysis. The resulting strain had an extended life span, indicating that the integrating vector contained the sir4-42 allele (data not shown). The SmaI fragments from the mutant or wild type SIR4 gene, which contained the region spanning 743 to the UAA stop at the end of the 1358 residue SIR4 open reading frame, were subcloned into Bluescript (Stratagene). Sequencing primers were made approximately 200 base pairs apart for this entire region, and it was sequenced by the single-strand approach (Sequenase version 2, U.S. Biochemicals). A single difference was found in the mutant which generated a stop codon at amino acid 1237 of the encoded protein, removing 121 residues from the SIR4 gene product.

A second gene involved in senescence in yeast, corresponding to UTH1 described above, has been identified. The UTH1 mutation, described above, rendered 14c sensitive to paraquat. The UTH1 gene was cloned from the CT3 library by its ability to confer resistance to paraquat. The sequence was obtained using standard methods. The nucleic acid sequence (SEQ ID NO. 1), and the encoded amino acid sequence (SEQ ID NO. 2), are shown in FIG. 15.

Furthermore, two additional *S. cerevisiae* genes, NCA3 (SEQ ID NO. 11, FIGS. 20A–B) and SAG1 (SEQ ID NO. 13, FIGS. 21A–B), which show a strong homology to UTH1 across a region referred to herein as the SUN domain, have been identified by screening a computerized database with the UTH1 sequence. A comparison of the sequences of the three genes reveals that they show 61 percent identitiy across the SUN domains (FIGS. 22A–B). The SUN domain of the UTH1 gene extends from nucleotide 236 to nucleotide 451, the SUN domain of the NCA3 gene extends from nucleotide 123 to nucleotide 338, and the SAG1 SUN domain extends from nucleotide 211 to nucleotide 426. The SUN domains are the regions of the genes which show the greatest homology. A partial sequence of a third gene with homology to UTH1, designated SUN4 (SEQ ID NO. 15), has also been identified. Deletion of either the NCA3 gene or the SAG1 gene results in a shortened life span compared with the wild-type yeast strain, indicating that these genes contribute to extended life span. This suggests that senescence may be controlled by a family of proteins which interact to regulate aging.

A third gene involved in senescence in yeast, corresponding to UTH4 described above, has been identified and the nucleic acid sequence (SEQ ID NO. 3) and encoded amino acid sequence (SEQ ID NO. 4) are shown in FIGS. 16A–E. A partial sequence (nucleotides 3–108) of the UTH4 gene was obtained from transformed yeast cells, and a database search revealed the identity and sequence of the complete UTH4 gene. UTH4 contains eight "repeat" boxes which comprise approximately one-third of the gene sequence. A comparison of the eight boxes at the amino acid level reveals that they are about fifty percent homologous (FIG. 23). More striking, however, is a comparison of the UTH4 repeating-box sequence with similar box sequences of several other genes, identified in various databases as having regions of homology with the repeating region of UTH4, including the yeast YGL023 gene (Chen et al., *Yeast* 7:309–312 (1991), SEQ ID NO. 5, FIGS. 17A–E), the human D43951 gene (SEQ ID NO. 7, FIGS. 18A–G), the human D13645 gene (SEQ ID NO. 9, FIGS. 19A–C) and the Drosophila PUMILIO gene (Barker et al., *Genes and Development*, 6:2313–2326 (1992). A computer database search revealed that each of these genes contains a similar eight-box region, and a comparison of the YGL023, D93451, PUMILIO and UTH4 genes across this region indicates a conservation of greater than fifty percent (FIG. 24).

UTH4 appears to be similar to SIR4 in that deletion of the entire gene does not confer extended life span upon *S. cerevisiae*. However, a specific mutation of the UTH4 gene results in an increased life span in the yeast compared with wild-type life span. This mutation can be a single nucleotide change which results in either an amino acid change or generation of a stop codon resulting in a truncated protein. The Lengthening of Life Span by SIR4-42 Requires SIR3

Figure 12:
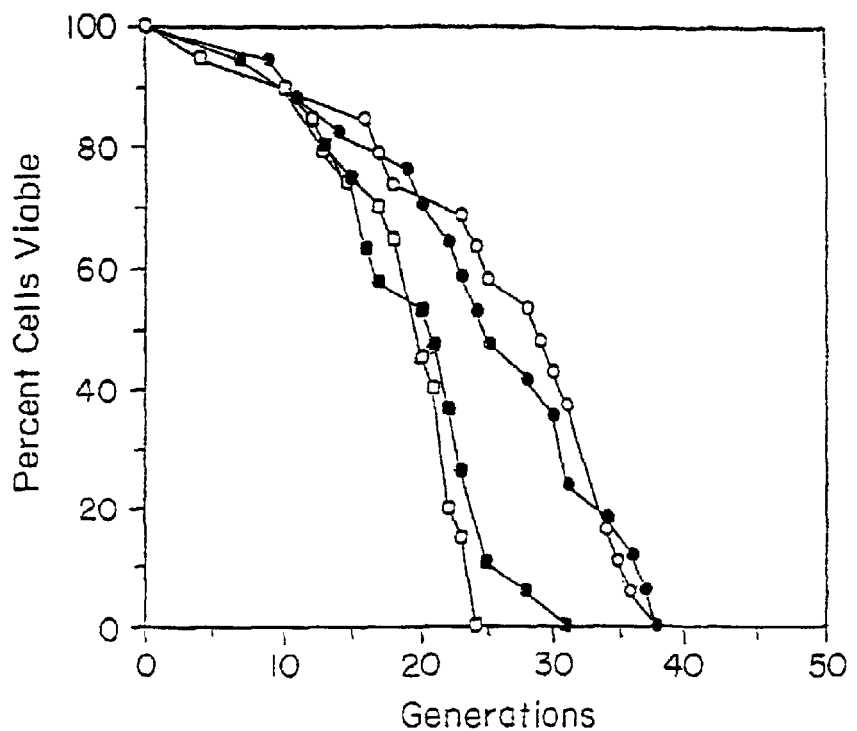
FIG. 12 is a graphic representation of mortality curves for 14c (SIR4, open squares), sir4-42 (closed circles), and the isogenic deletion in sir1 derivatives (sir4-42 Δsir1, open circles; SIR4 Δsir1, closed diamonds). Sample sizes were 20 cells (14c), 19 cells (SIR4 Δsir1), 18 cells (sir4-42), and 19 cells (sir4-42 Δsir1).
Figure 13:
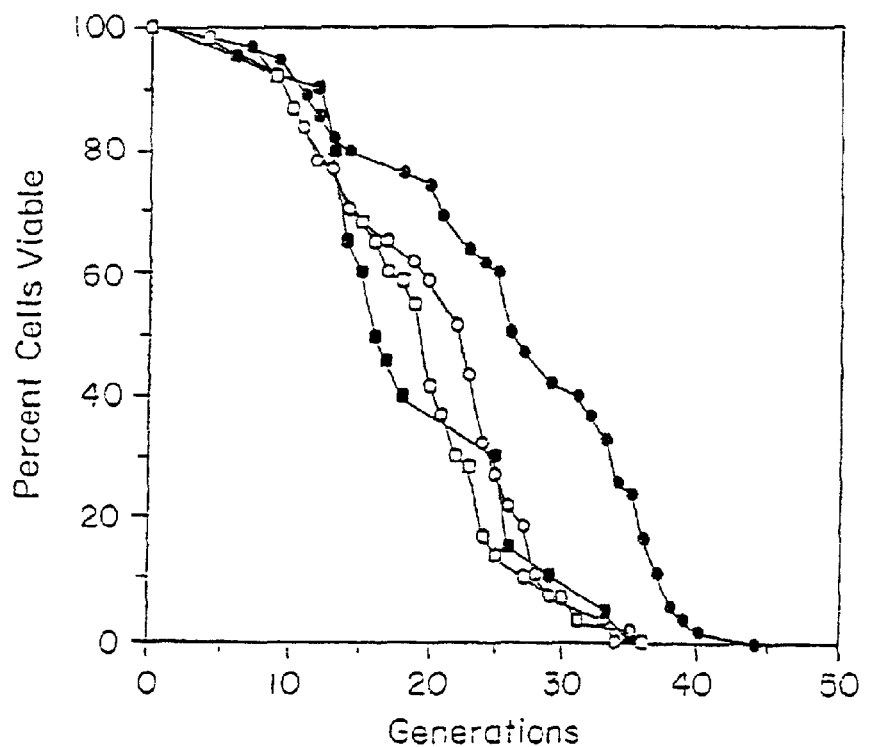
FIG. 13 is a graphic representation of mortality curves for 14c (SIR4, open squares), sir4-42 (closed circles), and the isogenic deletion in sir3 derivatives (sir4-42 Δsir3, open circles; SIR4 Δsir3, closed diamonds). Sample sizes were 60 cells (14c), 20 cells (SIR4 Δsir1), 19 cells (sir4-42), and 30 cells (sir4-42 Δsir1).

It was investigated whether sir4-42 acted alone or in concert with other members of the SIR complex. The activities of SIR2, SIR3, and SIR4 are closely coupled in that all are required for silencing at the HM loci and at telomeres (Aparicio, O. M. et al., *Cell* 66(6):1279–1287 (1991); Rine, J. and Herskowitz, I., *Genetics* 116:9–22 (1987)). The function of SIR1 is different in that it is only required at the HM loci (Aparicio, O. M. et al., *Cell* 66(6):1279–1287 (1991)), and even there, its requirement is not absolute (Pillus, L. and J. Rine, *Cell* 59:637–647 (1989)). To determine whether SIR3 and SIR1 were required for the extension of life span, the genes were disrupted in the sir4-42 mutant, and, as a control, in 14c. The sir1 deletion was generated using plasmid pJ123.2 which removes the C-terminal 335 amino acids from the 648 amino acid protein (Ivy, J. M. et al, *Mol. Cell.Biol.* 6:688–702 (1986)). The sir3 deletion was constructed by deleting 123 amino acids at the C-terminus of SIR3. The sir1 disruptions did not exert any effect on the sir4-42 mutant or its SIR4 parent (FIG. 12). In contrast, the sir3 disruption abolished the extension of life span conferred by sir4-42 (FIG. 13). This shortening of life span in the sir4-42 strain was specific because disruption of SIR3 did not alter the life span of the SIR4 parent (FIG. 13). Thus, the gain of function caused by sir4-42 appears to be an activity of the entire SIR complex, and not SIR4 alone.
Effects of the SIR4-42 Mutation on Telomeres Because the sir4-42 mutation results in a loss of activity at HM loci, it is possible that the mutation redirects the SIR complex to another chromosomal location, resulting in the observed extension in life span. One obvious possible location was telomeres, because loss of function mutations in SIR2, SIR3, or SIR4 relieve silencing at telomeres and also result in shorter telomeres (Aparicio, O. M. et al., *Cell* 66(6):1279–1287 (1991); Palladino, F. et al., *Cell* 75:543–555 (1993)). In mammalian cells, telomeres have been shown to shorten with age (Harley, C. B. et al., *Nature* 345:458–460 (1990)), and this shortening has been proposed as a causative agent of aging (Allsopp, R. C. et al., *PNAS, USA* 89:10114–10118 (1992); Olovnikov, A. M. *J. Theor. Biol.* 41:181–190 (1973)). If telomere shortening imposed a limit to life span, then excessive recruitment of SIR complex might counter aging by lengthening telomeres. Therefore, the length of telomeres in 14c and its Δsir4 and sir4-42 mutant derivatives was determined. Total genomic DNA was isolated, digested with XhoI, and separated on a 0.7% agarose gel and transferred to a GeneScreen Plus Hybridization Transfer Membrane (NEN Research Products). Hybridization and wash conditions were as suggested by the manufacturer. A plasmid containing 600 base pairs located within the conserved Y' region of yeast telomeres, supplied by V. Zakian, was nick translated (GIBCO BRL) and used as a probe (Chan, C. S. M. and B. K. Tye, *Cell* 33:563–573 (1983)). This probe overlapped the XhoI site and thus hybridized to fragments both telomere-proximal and telomere-distal to the restriction site. Most yeast telomeres contain the Y' region (Walmsley, R. M. et al., *Nature* 310:157–160 (1984)). Deletion of SIR4 resulted in a shortening of telomeres by approximately 50–100 bases (Palladino, F. et al., *Cell* 75:543–555 (1993)). Surprisingly, the length of telomeres in the sir4-42 mutant was indistinguishable from the Δsir4 mutant, indicating that the mutant behaved like the deletion with respect to activity at telomeres. Separate experiments confirmed that silencing at telomeres was also alleviated in the sir4-42 mutant just as in the Δsir4 strain (data not shown). Thus, the sir4-42 exhibits a loss of function phenotype. However, because sir4-42 extends life span and Δsir4 does not, the lengthened life span is probably unrelated to telomere length or silencing.

Expression Of The Carboxyl-Terminus of SIR4 Extends Life Span

Figure 14:
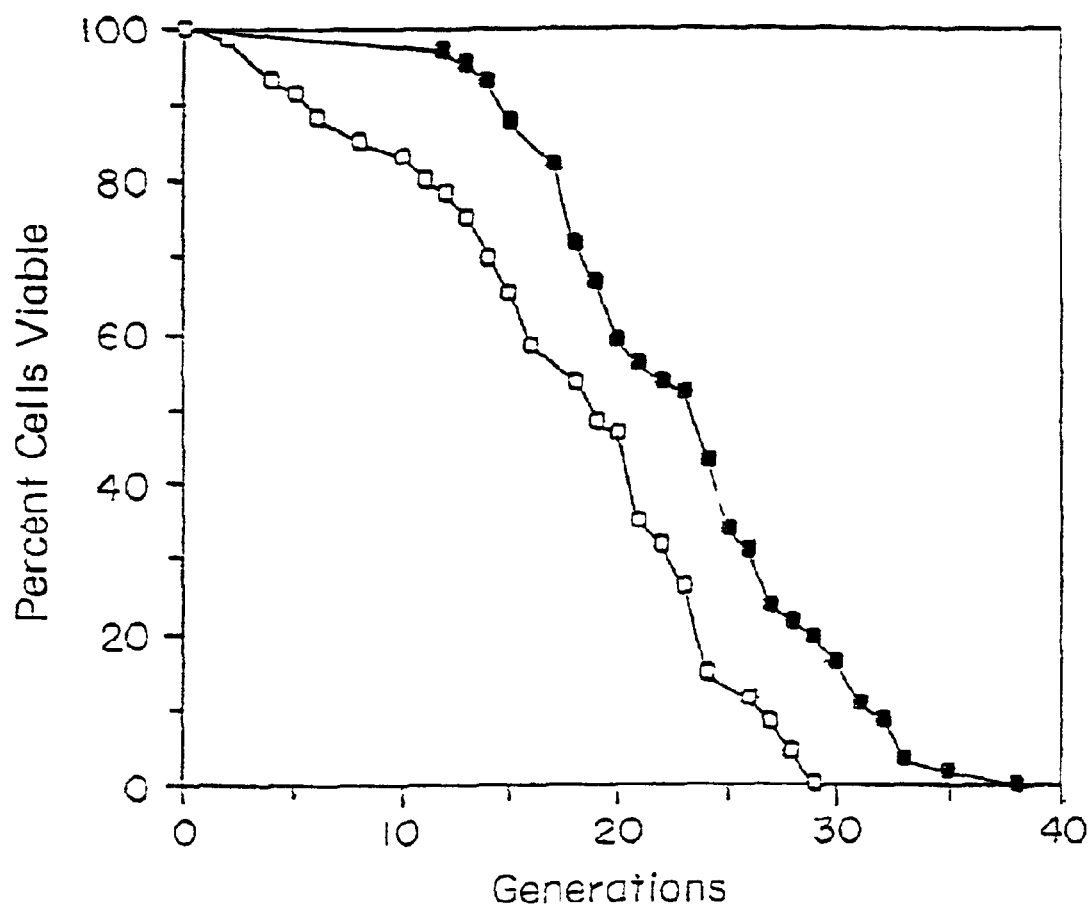
FIG. 14 is a graphic representation of the mortality curves for 14c (SIR4, open squares) and SIR4 plus anti-SIR4 (closed squares). Sample sizes were 50 cells (14c) and 46 cells (SIR4+Anti-SIR4).

Since the sir4-42 mutation removes the carboxyl-terminus of the protein, it is possible that this fragment of SIR4 localized the complex to HM loci and telomeres. Thus, overexpression of a carboxyl-terminal fragment of SIR4 might compete with the wild type protein for recruitment to HM loci and telomeres. A construct expressing only the carboxyl 154 residues of SIR4 has been shown to behave as an anti-SIR4 dominant negative mutant with respect to silencing at HM loci (Ivy, J. M. et al., *Mol. Cell.Biol.* 6:688–702 (1986); Marshall, M. et al, *Mol. Cell. Biol.* 7:4441–4452 (1987)). Therefore, a construct that expresses the carboxyl-terminal region of SIR4 (Ivy, J. et al., *Mol. Cell Biol.* 6:688–702 (1986)) was used to antagonize the native SIR4 protein and render cells sir4-. Transformation of this construct into 14c confirmed that it functioned as a dominant negative inhibitor of mating. The transformant was also stress resistant, as expected. Strikingly, the construct also extended the life span by about 30% (see FIG. 14). The strain labeled SIR4+Anti-SIR4 is 14c transformed with the plasmid pJH3A, a 2μ plasmid containing the C-terminal 154 amino acids of the SIR4 gene (Ivy, J. et al., Mol. Cell Biol. 6:688–702 (1986)).

Summary of Yeast Strains Described Above

Table 2 depicts the strain and genotype of all yeast strains described herein. All strains were generated in this study except BWG1-7A which is described in Guarente, L. and T. Mason, *Cell* 32:1279–1286 (1983)), and the mating testers CKy20 and CKy21 which were gifts of C. Kaiser. The terminology LEU2/sir4-42 in the strain BKy107 means the sir4-42 allele has been integrated at the LEU2 locus, for example.

TABLE 2

YEAST STRAINS USED IN THIS STUDY

| Strain | Genotype |
|---|---|
| BWG1-7A | Matα ade1-100 his4-519leu2-3,2-112 ura3-52 |
| PSY142 | Matα leu2-3,2-112lys2-801 ura3-52 |
| BKy1 | Matα ade1-100 his4-519 leu2-3,2-112 LYS2 ura3-52 |
| | Matα ADE HIS4 leu2-3,2-112 lys2-801 ura3-52 |
| BKy1-14a | Matα ade1-100 leu2-3,2-112 lys2-801 ura-3-52 |
| BKy1-14b | Matα leu2-3,2-112 ura3-52 |
| BKy1-14c | Matα ade1-100 his4-519 leu2-3,2-112 lys2-801 ura3-52 |
| BKy1-14d | Matα his4-519 leu2-3,2-112 ura3-52 |
| BKy5 | Matα ade1-100 his4-519 leu2-3,2-112 lys2-801 ura3-52 |
| BKy6 | Matα ade1-100 his4-519 leu2-3,2-112 lys2-801 ura3-52 |
| | Matα ade1-100 his4-519 leu2-3,2-112 lys2-801 ura3-52 |
| BKy17 | Matα ade1-100 his4-519 leu2-3,2-112 lys2-801 ura3-52 SIR4 |
| | Matα ade1-100 his4-519 leu2-3,2-112 lys2-801 ura3-52 sir4-42 |
| BKy21 | Matα ade1-100 his4-519 leu2-3,2-112 lys2-801 ura3-52 sir4-42 |
| BKy28 | Matα ade1-100 his4-519 leu2-3,2-112 lys2-801 ura3-52 sir4-42 |
| | Matα ade1-100 his4-519 leu2-3,2-112 lys2-801 ura3-52 sir4-42 |
| BKy30 | Matα ade1-100 his4-519 leu2-3,2-112 lys2-801 ura 3-52 SIR4/LEU2 |
| Bky100 | Matα ade1-100 his4-519 leu2-3,2-112 lys2-801 ura3-52 Ste4::URA3 |
| BKy101 | Matα ade1-100 his4-519 leu2-3,2-112 lys2-801 ura3-52 ste12::URA3 |
| BKy102 | Matα ade1-100 his4-519 leu2-3,2-112 lys2-801 ura3-52 sir1::LEU2 |
| BKy103 | Matα ade1-100 his4-519 leu2-3,2-112 lys2-801 ura3-52 sir3::URA3 |
| BKy104 | Matα ade1-100 his4-519 leu2-3,2-112 lys2-801 ura3-52 sir4::URA3 |
| BKY105 | Matα ade1-100 his4-519 leu2-3,2-112 lys2-801 ura3-52 sir4-42 sir1::LEU2 |
| BKy106 | Matα ade1-100 his4-519 leu2-3,2-112 lys2-801 ura3-52 sir4-42 sir3::URA3 |
| Bky107 | Matα ade1-100 his4-519 lys2-801 ura3-52 sir4::URA3 LEU2/ sir4-42 |
| BKy108 | Matα ade1-100 his4-519 leu2-3,2-112 ly2-801 sir4-42 URA3/ SIR4 |
| CKy20 | Matα arg1 tsm11 |
| CKy21 | Matα arg1 tsm11 |

Framework for Relating Silencing, Aging, Stress, and Telomeres

Table 3 summarizes the effects of three mutant alleles of SIR4 that alleviate silencing and also promote stress resistance.

TABLE 3

PHENOTYPES OF ALLELES

| Allele | Amino Acids | Mating | Stress Resistance | % Life Span Increase |
|---|---|---|---|---|
| SIR4 | 1–1358 | + | Sensitive | — |
| sir4-42 | 1–1237 | – | Resistant | 30–60% |
| sir4Δ | — | – | Resistant | none |
| SIR4 + Anti-SIR4 | 1–1358 + 1205–1358 | – | Resistant | 20–45% |

Deletion of SIR3 has effects indistinguishable from deletion of SIR4 (data not shown). Of all of these mutations, however, only sir4-42 extends life span. To explain these findings, it is proposed that a locus that is repressed by the SIR complex can promote resistance to stress when repression is eliminated. In principle, this locus could be linked to HML, HMR, a telomere, or reside at some other location. Linkage to HM loci is not plausible, however, because deletion of SIR1, which weakens repression at the HM loci, does not promote stress resistance. For simplicity, it is suggested that there is a telomere-linked, stress-resistant locus under SIR control.

It is further suggested that the lengthening of life span is due to a different locus, termed AGE, that is independent of effects at HM loci or telomeres. The repression of the "AGE" locus by SIR4 is essential to longevity, according to this view, and aging may result from a breakdown in the silencing of that locus. It is, of course, possible that silencing at more than one chromosomal region governs aging. In any case, the "AGE" locus is proposed to be unlinked to telomeres or HM loci because both the sir4-42 mutation and the Δsir4 eliminate silencing at HM loci and at telomeres, but only the sir4-42 allele extends life span. Further, the extension of life span by sir4-42 is semi-dominant in a strain also containing SIR4, indicating that it is a gain of function mutation with regard to life span. The function gained in the mutant must relate to the normal silencing activity of the SIR complex because the ability of sir4-42 to promote longevity requires the integrity of SIR3.

It is also suggested that the sir4-42 mutation prevents recruitment of the SIR complex to HML, HMR, and telomeres, rendering the complex more available for any other site of action in the cell. The carboxyl 121 residues that are missing in the sir4-42 mutant may be important in the recruitment of the SIR complex to these chromosomal sites. Consistent with the view that the carboxyl terminus of SIR4 helps localize the SIRs to HM loci and telomeres, overexpression of the carboxyl 163 residues of SIR4 is known to exert a dominant negative effect on repression at HM loci (Ivy, J. et al., *Mol. Cell Biol.* 6:688–702 (1986); Marshall, M. et al., *Mol. Cell. Biol.* 7:4441–4452 (1987)). Expression of this SIR4 fragment, in addition to blocking repression at HML and HMR, promoted longevity.

A breakdown in silencing by the SIR complex may be causally related to aging in *S. cerevisiae*. The identification of SIR4 as a gene that affects life span in yeast thus appears to relate telomeres and aging. However, as described above, telomeres in the sir4-42 strain, just as in the Δsir4 null mutant, are shorter than wild type. This suggests that telomere length is not causally related to aging. Nevertheless, it is theoretically possible that the mutation counters telomere shortening selectively in old cells.

Methods of Isolating Strains with Increased Life Span

The techniques described above can be used to isolate other yeast strains with increased life spans, and thereby to isolate other genes, from yeast and other cell types (e.g. vertebrate, mammalian) involved in senescence. Any budding yeast strain for which the life span is known can be utilized. The life span of the strain can be determined by calculating the mean number of generations before senescence in a sample of colonies of the strain of interest. A sample of the strain of interest is exposed to a mutagen, such as ethylmethane sulfonate (EMS), N-methyl-N'-nitro-N-nitrosoguanidine (MNNG), or ultraviolet irradiation. Mutants with increased life spans can then be isolated as follows.

STARVATION-RESISTANCE METHOD. Yeast cells that have been exposed to mutagen are plated with minimal nutrients (including carbon and nitrogen sources, as well as the amino acids and nucleotides that are required by the particular strain for growth). The minimal plates are replica-plated to plates lacking vital nutrients, such as nitrogen and carbon (the starvation plates). After incubation of the starvation plates at a temperature appropriate for growth, for several days, the starvation plates are replicated back to rich media plates. The rare colonies containing living cells when plated back onto rich medium (the "starvation resistant" colonies) are then examined to determine whether the life span is extended. Life span is calculated as described above. This method is particularly appropriate for short-lived strains, which are more sensitive to starvation.

CELL SURFACE LABELLING METHOD. This method takes advantage of the fact that the cell surface (including the cell membrane and cell wall) of a daughter cell in some budding yeast, such as *S. cerevisiae*, is fabricated entirely of new materials: when the cell surface of the mother cell is labelled, the surface of the daughter cells remains unlabelled. In one embodiment, the cell surface is labelled with biotin. When avidin linked to fluorescence is coupled to the biotin, the cell surface fluoresces. Alternatively, any other method of labelling the cell surface with a fluorescent marker is appropriate. Daughter cells remain unlabelled (will not fluoresce). Fluorescently labelled yeast cells are plated and cultured for a period of time greater than the life span of the non-mutant strain (as measured by time necessary for one cell division, multiplied by the number of divisions, or generations, in the life span). If desired, the yeast cells may be sampled at regular time intervals in order to monitor the plating efficiency of the cells; the efficiency will drop precipitously after the chronological life span has passed. The yeast cells are then subjected to fluorescence-activated cell sorting (FACS), to isolate the fluorescently labelled cells. The fluorescent cells are then replated; only mutants with increased life spans will grow.

TEMPERATURE-SENSITIVE METHOD. A temperature-sensitive mutant strain, in which the daughter cells die at the non-permissive temperature, is utilized. For example, yeast cells with a mutation in the mdm2-2 gene (also known as the ole-1 gene) (McConnell, S. et al., *J. Cell Biol.* 111:967–976 (1990)) bud forth living daughter cells at 30° C., but not at 37° C., because of a failure in appropriate organelle segregation at the higher temperature (mitochondria are not put into daughter cells). In such a temperature-sensitive mutant, the daughter cells bud off from the mother cell and die at the non-permissive temperature; the dead daughter cells remain near the mother cell. Therefore, each mother cell grown at the non-permissive temperature generates a microcolony of N cells, where N is equal to the number of generations in the life span of the mother cell. Mutant strains will display microcolonies wherein the number of cells is greater than N.

To isolate mutants, cells are plated at the permissive temperature. A sample of cells from each colony is then transferred to a plate to be grown at the non-permissive temperature. Microcolonies with cell number greater than N are indicative of mutants; cells from the colonies which have been identified as mutant can be selected from the plates grown at the permissive temperature. Alternatively, cells are plated directly at the non-permissive temperature, and grown for a period of time greater than the life span as measured by time necessary for one cell division, multiplied by the number of divisions, or generations, in the life span. If desired, the yeast cells may be sampled at regular time intervals in order to monitor the plating efficiency of the cells; the efficiency will drop precipitously after the chronological life span has passed. After this time, the plates are shifted back to the permissive temperature. Only longer-lived mutants will grow after the temperature shift.

Methods of Identifying Agents which Affect Life Span

The above-described methods for isolating mutant yeast cells with a longer life span can be employed to identify agents which alter the life span of a yeast strain. In this embodiment of the current invention, the yeast strain of interest, for which the life span is known or has been calculated, is exposed to the agent to be tested rather than subjected to a mutagen. The samples thus exposed are then examined for longer-lived colonies, using any of the methods described above. Colonies exhibiting a longer life span in the presence of the agent than in the absence of the agent are indicative of the ability of the agent to increase life span, or to postpone senescence. Agents include drugs, peptides, oligonucleotides, and genes encoding proteins that increase life span, such as genes isolated by the methods described below.

Methods of Isolating Genes Involved in Altering Life Span

Genes which contribute to senescence can be isolated by complementation analysis, or by isolation of DNA homologous to other genes known to contribute to senescence. In one embodiment of the current invention, cells from a budding yeast strain, such as 14c, in which the SIR4 gene has been mutated as described above, and which as a result have a longer life span, are utilized. The SIR4 gene can be mutated through site-specific mutagenesis, for example. A genomic DNA library generated from an organism of interest, including another yeast strain, bacteria, or mammals, is used to transform the yeast cells. The cells are then plated and grown. Those yeast cells which exhibit the usual life span of the yeast strain, rather than the longer life of the cells in which SIR4 is mutated, are selected. These cells contain DNA from the organism of interest which comprises a gene that contributes to senescence. The DNA from the organism of interest is then isolated from these yeast cells.

Genes which contribute to longer life span can also be isolated by complementation analysis, or by isolation of DNA homologous to other genes known to contribute to longer life span. In one embodiment of the current invention, cells from a budding yeast strain, such as 14c, are utilized. These cells should have a normal life span; i.e., the SIR4 gene should not be mutated. A genomic DNA library generated from an organism of interest, including another yeast strain, bacteria, or mammals, is used to transform the yeast cells. The cells are then plated and grown. Those yeast cells which exhibit a longer life span of the yeast strain, rather than the usual life span of the cells, are selected. These cells contain DNA from the organism of interest which comprises a gene that contributes to longer life span (i.e., a gene that increases life span). The DNA from the organism of interest is then isolated from these yeast cells. In another embodiment, genes in other organisms that are the functional equivalent of SIR4 in yeast can be investigated to determine whether a mutation corresponding to the SIR4 mutation (stop codon at amino acid 1237 of the encoded protein) results in a mutated gene that contributes to longer life span.

In another embodiment of the current invention, homologous genes can be isolated by hybridization. In one particular embodiment, a labelled DNA fragment comprising the SIR4 gene, the UTH1 gene or the UTH4 gene is used to probe cellular DNA from an organism of interest under high, medium or low hybridization stringency conditions, depending on the degree of homology sought. For description of appropriate stringency conditions, see Sambrook et al., eds., *Molecular Cloning: A Laboratory Manual*, 2nd ed., Cold Spring Harbor Laboratory Press, 1989, or Ausubel, F. M. et al., eds. *Current Protocols in Molecular Biology*, 1994. DNA hybridizing to the probe is isolated, and complementation analysis is performed to verify that the DNA comprises a gene which contributes to senescence. In one embodiment, DNA from an organism of interest is hybridized under high stringency conditions to DNA comprising a mutated SIR4 gene (i.e., a stop codon at amino acid 1237 of the encoded protein). Alternatively, labelled DNA comprising genes isolated by the complementation method described above can be used as the probe.

Homologous genes can also be found by computerized database searches to identify genes which include regions of homology to the SUN domains of the UTH1, NCA3 and SAG1 genes or to the repeating-box region of the UTH4, PUMILIO, YGL023, D13645 or D43951 genes. Homologous genes can also be found by the polymerase chain reaction (PCR) (see Sakai, R. K. et al., Science 230:1350–4 (1985), and Sakai, R. K. et al., Science 239: 487–91 (1988)). Synthetic oligonucleotide primers which comprise regions of the SIR4 gene or the UTH1 gene can be used. In one embodiment, synthetic oligonucleotide primers which comprise the region of the SIR4 gene that contains the mutation (the stop codon at amino acid 1237 of the encoded protein) are used. Alternatively, oligonucleotides can be patterned after any gene, such as those isolated by this method or any of the above methods, which contributes to senescence or to longer life span. The oligonucleotides are utilized in PCR to generate multiple copies of DNA of interest from a sample of genomic DNA from the organism of interest. The DNA multiplied in PCR is then isolated, and complementation analysis is performed to verify that the DNA comprises a functional gene which contributes to senescence or to longer life span. Once genes have been isolated using these methods, standard procedures can then be used to isolate the proteins encoded by the genes.

Methods of Increasing Life Span in Yeast

Because the sir4-42 mutation is a semi-dominant mutation, and because addition of "anti-SIR4" (residues 1205–1358 of SIR4) to yeast cells increases the life span by 20–45%, it is now possible to increase the life span of any cell by adding "anti-SIR4". For example, a plasmid which expresses residues 1205–1358 can be inserted into the cell of interest. Expression of the anti-SIR4 protein will increase the life span. The life span can also be increased by adding mutant SIR4 protein (protein produced by the mutated SIR4 gene, in which there is a stop codon at amino acid 1237 of the encoded protein). For example, a plasmid which expresses the mutant SIR4 protein can be inserted into the cell of interest. Alternatively, "anti-SIR4" protein or protein produced by the mutant SIR4 gene can be added to the cell, thereby increasing the cell's life span.

Equivalents

Those skilled in the art will recognize, or be able to ascertain using no more than routine experimentation, many equivalents to specific embodiments of the invention described specifically herein. Such equivalents are intended to be encompassed in the scope of the following claims.

SEQUENCE LISTING

```
<160> NUMBER OF SEQ ID NOS: 48

<210> SEQ ID NO 1
<211> LENGTH: 1946
<212> TYPE: DNA
<213> ORGANISM: Saccharomyces cerevisiae
<220> FEATURE:
<221> NAME/KEY: CDS
<222> LOCATION: (322)...(1671)
<223> OTHER INFORMATION: UTH1

<400> SEQUENCE: 1
tgaaaaagtg gaactagacc ccacgtcagc gggcctaggc ccttcaatgt gttagaatac      60
acagcgtgcc tagttcctgg tgcctggatc tcgaggccgc ggcactggaa aagcccttc     120 ttttccagat cgggaaacct aatgagtcca taaaaagaaa tgtagaggtg gtgttgacgt     180
tttgccgctt ttgggcaagt aggtctttct gcacggcccg gcccgggtcg tgcggaaaaa     240
gaaaaaagca gacaaaacaa aatttttcct tttttcgcc tttgtttctc ctgattcggg      300
tatataagtg aataccatct a atg tgt ttc ctt ctc gag acc tcg gcg tct      351
                        Met Cys Phe Leu Leu Glu Thr Ser Ala Ser
                          1               5                  10 ccc aga tca aag ctc agc aaa gat ttt aaa ccg caa ttt acg ctc ctt      399
Pro Arg Ser Lys Leu Ser Lys Asp Phe Lys Pro Gln Phe Thr Leu Leu
                15                  20                  25 tca tcg gta act aag aag aaa aaa aaa aaa gta cga cca cac aat ttc      447
Ser Ser Val Thr Lys Lys Lys Lys Lys Val Arg Pro His Asn Phe
         30                  35                  40 cag tgt att cat tcc tta aac ttc gtt tat ttt tta ttc att cat tca      495
Gln Cys Ile His Ser Leu Asn Phe Val Tyr Phe Leu Phe Ile His Ser
     45                  50                  55 ttt tta ttt gaa tat aac caa cta cta gtc ctt cct tta aac aaa aat      543
Phe Leu Phe Glu Tyr Asn Gln Leu Leu Val Leu Pro Leu Asn Lys Asn
 60                  65                  70
```

-continued

```
tta ccc tcc ctt aat ttt tca aga aat tcc agt atg aaa tta tcc gct    591
Leu Pro Ser Leu Asn Phe Ser Arg Asn Ser Ser Met Lys Leu Ser Ala
 75              80                  85                  90 cta tta gct tta tca gcc tcc acc gcc gtc ttg gcc gct cca gct gtc    639
Leu Leu Ala Leu Ser Ala Ser Thr Ala Val Leu Ala Ala Pro Ala Val
             95                  100                 105 cac cat agt gac aac cac cac cac aac gac aag cgt gcc gtt gtc acc    687
His His Ser Asp Asn His His His Asn Asp Lys Arg Ala Val Val Thr
                 110                 115                 120 gtt act cag tac gtc aac gca gac ggc gct gtt gtt att cca gct gcc    735
Val Thr Gln Tyr Val Asn Ala Asp Gly Ala Val Val Ile Pro Ala Ala
         125                 130                 135 acc acc gct acc tcg gcg gct gct gat gga aag gtc gag tct gtt gct    783
Thr Thr Ala Thr Ser Ala Ala Ala Asp Gly Lys Val Glu Ser Val Ala
 140                 145                 150 gct gcc acc act act ttg tcc tcg act gcc gcc gcc gct act acc tct    831
Ala Ala Thr Thr Thr Leu Ser Ser Thr Ala Ala Ala Ala Thr Thr Ser
155                 160                 165                 170 gcc gcc gcc tct tct tcc tcc tct tcc tct tcc tct tcc tct tct         879
Ala Ala Ala Ser Ser Ser Ser Ser Ser Ser Ser Ser Ser Ser Ser
                 175                 180                 185 tcc tct gtt ggt tct gga gat ttt gaa gat ggt acc att tcc tgt tct    927
Ser Ser Val Gly Ser Gly Asp Phe Glu Asp Gly Thr Ile Ser Cys Ser
             190                 195                 200 gat ttc cca tcc gga caa ggt gct gtc tcc ttg gac tgg tta ggt cta    975
Asp Phe Pro Ser Gly Gln Gly Ala Val Ser Leu Asp Trp Leu Gly Leu
         205                 210                 215 ggc ggc tgg gct tcc atc atg gac atg aac ggt aac acc gcc acc tct    1023
Gly Gly Trp Ala Ser Ile Met Asp Met Asn Gly Asn Thr Ala Thr Ser
 220                 225                 230 tgt caa gac gga tac tac tgt tct tac gct tgt tct cca ggt tac gct    1071
Cys Gln Asp Gly Tyr Tyr Cys Ser Tyr Ala Cys Ser Pro Gly Tyr Ala
235                 240                 245                 250 aag acc caa tgg cct tct gaa caa cct tcc gat ggt aga tcc gtt ggt    1119
Lys Thr Gln Trp Pro Ser Glu Gln Pro Ser Asp Gly Arg Ser Val Gly
                 255                 260                 265 ggt tta tac tgt aag aac ggt aaa tta tac cgt tcc aac acc gac act    1167
Gly Leu Tyr Cys Lys Asn Gly Lys Leu Tyr Arg Ser Asn Thr Asp Thr
             270                 275                 280 aac agt ttg tgt gta gaa ggt caa ggc tct gct caa gct gtt aac aag    1215
Asn Ser Leu Cys Val Glu Gly Gln Gly Ser Ala Gln Ala Val Asn Lys
         285                 290                 295 gtc tcc ggc tcc att gct atc tgt ggt acc gat tat cca ggt tct gaa    1263
Val Ser Gly Ser Ile Ala Ile Cys Gly Thr Asp Tyr Pro Gly Ser Glu
 300                 305                 310 aac atg gtc gtt cct acc gta gtt ggc gct ggt tcc tcc caa cca atc    1311
Asn Met Val Val Pro Thr Val Val Gly Ala Gly Ser Ser Gln Pro Ile
315                 320                 325                 330 aac gtc atc aag gag gac tcc tac tat caa tgg caa ggt aag aag acc    1359
Asn Val Ile Lys Glu Asp Ser Tyr Tyr Gln Trp Gln Gly Lys Lys Thr
                 335                 340                 345 tct gcc caa tac tac gtt aac aac gct ggt gtc tct gtg gaa gat ggt    1407
Ser Ala Gln Tyr Tyr Val Asn Asn Ala Gly Val Ser Val Glu Asp Gly
             350                 355                 360 tgt atc tgg ggt act gag ggt tcc ggt gtc ggt aac tgg gcc cca gtt    1455
Cys Ile Trp Gly Thr Glu Gly Ser Gly Val Gly Asn Trp Ala Pro Val
         365                 370                 375 gtc ttg ggt gct ggt tac act gat ggt atc act tac ttg tcc atc att    1503
Val Leu Gly Ala Gly Tyr Thr Asp Gly Ile Thr Tyr Leu Ser Ile Ile
```

-continued

```
                380               385                 390
cca aac cca aac aac aaa gaa gca cca aac ttt aac atc aag atc gtt    1551
Pro Asn Pro Asn Asn Lys Glu Ala Pro Asn Phe Asn Ile Lys Ile Val
395                 400                 405                 410 gcc acc gat ggc tct acc gtc aat ggt gct tgc tct tac gaa aat ggt    1599
Ala Thr Asp Gly Ser Thr Val Asn Gly Ala Cys Ser Tyr Glu Asn Gly
                415                 420                 425 gtc tac tct ggc tct ggc tct gac ggt tgt act gtt tca gtt act tct    1647
Val Tyr Ser Gly Ser Gly Ser Asp Gly Cys Thr Val Ser Val Thr Ser
            430                 435                 440 ggt tct gct aac ttt gtc ttc tac taggccttt ttccttgaat attgcaaata    1701
Gly Ser Ala Asn Phe Val Phe Tyr
            445                 450 agcttttgct agtactttt ttactccgtt catttatgg tttatttttc aattagttcg    1761
tttttccaca atacaaaaaa acacagtcct ttgtactatc cctttatt cattatttt    1821 tctttttaa gataccacta gatattatca tatatagcat attatataac ataaaaagtc    1881
aagaaaaaaa atgttttat cactttctat aactgcatat ctttttttgc atttcgaatg    1941
attgc                                                              1946
```

<210> SEQ ID NO 2
<211> LENGTH: 450
<212> TYPE: PRT
<213> ORGANISM: Saccharomyces cerevisiae
<220> FEATURE:
<221> NAME/KEY: VARIANT
<222> LOCATION: (1)...(441)
<223> OTHER INFORMATION: Xaa = Any Amino Acid

<400> SEQUENCE: 2

```
Met Cys Phe Leu Leu Glu Thr Ser Ala Ser Pro Arg Ser Lys Leu Ser
 1               5                  10                  15

Lys Asp Phe Lys Pro Gln Phe Thr Leu Leu Ser Ser Val Thr Lys Lys
            20                  25                  30

Lys Lys Lys Lys Val Arg Pro His Asn Phe Gln Cys Ile His Ser Leu
        35                  40                  45

Asn Phe Val Tyr Phe Leu Phe Ile His Ser Phe Leu Phe Glu Tyr Asn
    50                  55                  60

Gln Leu Leu Val Leu Pro Leu Asn Lys Asn Leu Pro Ser Leu Asn Phe
65                  70                  75                  80

Ser Arg Asn Ser Ser Met Lys Leu Ser Ala Leu Leu Ala Leu Ser Ala
                85                  90                  95

Ser Thr Ala Val Leu Ala Ala Pro Ala Val His His Ser Asp Asn His
            100                 105                 110

His His Asn Asp Lys Arg Ala Val Val Thr Val Thr Gln Tyr Val Asn
        115                 120                 125

Ala Asp Gly Ala Val Val Ile Pro Ala Ala Thr Thr Ala Thr Ser Ala
    130                 135                 140

Ala Ala Asp Gly Lys Val Glu Ser Val Ala Ala Thr Thr Thr Leu
145                 150                 155                 160

Ser Ser Thr Ala Ala Ala Thr Thr Ser Ala Ala Ala Ser Ser Ser
                165                 170                 175

Ser Ser Ser Ser Ser Ser Ser Ser Ser Ser Val Gly Ser Gly
            180                 185                 190

Asp Phe Glu Asp Gly Thr Ile Ser Cys Ser Asp Phe Pro Ser Gly Gln
        195                 200                 205
```

-continued

| | | | | | | | | | | | |
|---|---|---|---|---|---|---|---|---|---|---|---|
|Gly|Ala|Val|Ser|Leu|Asp|Trp|Leu|Gly|Leu|Gly|Gly|Trp|Ala|Ser|Ile|
| |210| | | | |215| | | |220| | | | | |

Met Asp Met Asn Gly Asn Thr Ala Thr Ser Cys Gln Asp Gly Tyr Tyr
225                 230                 235                 240

Cys Ser Tyr Ala Cys Ser Pro Gly Tyr Ala Lys Thr Gln Trp Pro Ser
            245                 250                 255

Glu Gln Pro Ser Asp Gly Arg Ser Val Gly Gly Leu Tyr Cys Lys Asn
        260                 265                 270

Gly Lys Leu Tyr Arg Ser Asn Thr Asp Thr Asn Ser Leu Cys Val Glu
    275                 280                 285

Gly Gln Gly Ser Ala Gln Ala Val Asn Lys Val Ser Gly Ser Ile Ala
290                 295                 300

Ile Cys Gly Thr Asp Tyr Pro Gly Ser Glu Asn Met Val Val Pro Thr
305                 310                 315                 320

Val Val Gly Ala Gly Ser Ser Gln Pro Ile Asn Val Ile Lys Glu Asp
            325                 330                 335

Ser Tyr Tyr Gln Trp Gln Gly Lys Lys Thr Ser Ala Gln Tyr Tyr Val
        340                 345                 350

Asn Asn Ala Gly Val Ser Val Glu Asp Gly Cys Ile Trp Gly Thr Glu
    355                 360                 365

Gly Ser Gly Val Gly Asn Trp Ala Pro Val Val Leu Gly Ala Gly Tyr
370                 375                 380

Thr Asp Gly Ile Thr Tyr Leu Ser Ile Ile Pro Asn Pro Asn Asn Lys
385                 390                 395                 400

Glu Ala Pro Asn Phe Asn Ile Lys Ile Val Ala Thr Asp Gly Ser Thr
            405                 410                 415

Val Asn Gly Ala Cys Ser Tyr Glu Asn Gly Val Tyr Ser Gly Ser Gly
        420                 425                 430

Ser Asp Gly Cys Thr Val Ser Val Thr Ser Gly Ser Ala Asn Phe Val
    435                 440                 445

Phe Tyr
450

<210> SEQ ID NO 3
<211> LENGTH: 3455
<212> TYPE: DNA
<213> ORGANISM: Saccharomyces cerevisiae
<220> FEATURE:
<221> NAME/KEY: CDS
<222> LOCATION: (663)...(3164)
<223> OTHER INFORMATION: UTH4

<400> SEQUENCE: 3
aagctttaac gggatcttct aacaacaaat agcataataa ccaaaaacca gcttcagtgg      60
gatcagccta tcgacacgcc ttttttagcg gtctaacaat ctccgtttat gtcgtatgga     120
atttctatac ttgaccctac cttatttctc gaatatgcct ataaggattt tctcgaaaga     180
agggcttcgg gaaagaggcg cctcaggcaa aaatgagcaa aaaaaaaaaa aaaagaaaa      240 gattcgaaga tctatgaaaa atttatgcag attcgttgag agttataagg attttactct     300
ttatggttat aggtttcatt ctaaaatcaa gcataaattt tgtgttttgt cttcctcttt     360
tcctgtcctc ttttttgcc atcctctgtc gccattgaag tcgaacttta tagatagatt      420
tactcttgat tctcacgcat ctcaggccac ctggacactg tacatggttg tgattgttct     480
ctttctcagt tatcgaaatt gatcctaggc ttatactcca aaatcggctc tgcacacgcc     540
ttatttttgt ggtttcactt tactaacaca acattctttt attcaatcag atcaataacg     600

```
aaccatttcc atctgccgac tcagcatcga ttttaactac gtctacatca ataactcct    660 ta atg tct tac aat cat cag cct caa cta tct att aac tcc gtc caa      707
   Met Ser Tyr Asn His Gln Pro Gln Leu Ser Ile Asn Ser Val Gln
   1           5                   10                  15 tca ctc ttg gag ccc gtg acc cct ccg cct ttg ggc cag atg aat aac     755
Ser Leu Leu Glu Pro Val Thr Pro Pro Leu Gly Gln Met Asn Asn
            20                  25                  30 aaa aga aac cat caa aag gct cat tcg ctt gat ctc tct ggt ttt aat     803
Lys Arg Asn His Gln Lys Ala His Ser Leu Asp Leu Ser Gly Phe Asn
                35                  40                  45 cag ttc ata tca tcg aca caa tct ccc ttg gct ttg atg aat aat aca     851
Gln Phe Ile Ser Ser Thr Gln Ser Pro Leu Ala Leu Met Asn Asn Thr
            50                  55                  60 tca aca tcg aat tct gct aac tct ttt tcc ccg aat cct aat gct gct     899
Ser Thr Ser Asn Ser Ala Asn Ser Phe Ser Pro Asn Pro Asn Ala Ala
65                  70                  75 agc aac tcc act ggg ctt tca gcc tca atg gca aat cct cca gcc att     947
Ser Asn Ser Thr Gly Leu Ser Ala Ser Met Ala Asn Pro Pro Ala Ile
80                  85                  90                  95 cta cca tta atc aat gag ttt gat ctg gaa atg gat ggt ccc agg aga     995
Leu Pro Leu Ile Asn Glu Phe Asp Leu Glu Met Asp Gly Pro Arg Arg
                100                 105                 110 aaa tca agc cac gat ttc acg gtt gtt gct cct tcg aac tct ggt gtc    1043
Lys Ser Ser His Asp Phe Thr Val Val Ala Pro Ser Asn Ser Gly Val
            115                 120                 125 aat acc tcc agt tta att atg gaa aca cca tcc tct tca gtg act cct    1091
Asn Thr Ser Ser Leu Ile Met Glu Thr Pro Ser Ser Ser Val Thr Pro
            130                 135                 140 gct gca tct ctc aga aat ttt agc aat agt aat aat gct gct tcc aaa    1139
Ala Ala Ser Leu Arg Asn Phe Ser Asn Ser Asn Asn Ala Ala Ser Lys
            145                 150                 155 tgt gga gtg gat aat tcg tca ttt ggt ttg agt agc tca acg tct tca    1187
Cys Gly Val Asp Asn Ser Ser Phe Gly Leu Ser Ser Ser Thr Ser Ser
160                 165                 170                 175 tct atg gtc gaa atc agc gca cta ccc ctt aga gat ctg gat tat atc    1235
Ser Met Val Glu Ile Ser Ala Leu Pro Leu Arg Asp Leu Asp Tyr Ile
            180                 185                 190 aaa ctt gcc act gac cag ttt ggc tgc cgt ttt ctt caa aaa aaa tta    1283
Lys Leu Ala Thr Asp Gln Phe Gly Cys Arg Phe Leu Gln Lys Lys Leu
            195                 200                 205 gaa acc ccc agt gaa tcc aat atg gtg aga gac ttg atg tat gaa caa    1331
Glu Thr Pro Ser Glu Ser Asn Met Val Arg Asp Leu Met Tyr Glu Gln
            210                 215                 220 att aag cca ttt ttc ttg gac ctt att ttg gat ccg ttc ggt aac tat    1379
Ile Lys Pro Phe Phe Leu Asp Leu Ile Leu Asp Pro Phe Gly Asn Tyr
            225                 230                 235 ttg gtt caa aaa cta tgc gat tat tta act gcc gag caa aag aca tta    1427
Leu Val Gln Lys Leu Cys Asp Tyr Leu Thr Ala Glu Gln Lys Thr Leu
240                 245                 250                 255 tta ata caa aca ata tat cca aat gtt ttc caa ata tca atc aat cag    1475
Leu Ile Gln Thr Ile Tyr Pro Asn Val Phe Gln Ile Ser Ile Asn Gln
            260                 265                 270 tac gga act cgt tcc tta cag aaa att ata gac act gtc gat aac gaa    1523
Tyr Gly Thr Arg Ser Leu Gln Lys Ile Ile Asp Thr Val Asp Asn Glu
            275                 280                 285 gtt caa atc gat ctc att att aag gga ttt tcc caa gaa ttt act tcg    1571
Val Gln Ile Asp Leu Ile Ile Lys Gly Phe Ser Gln Glu Phe Thr Ser
            290                 295                 300
```

```
att gag caa gtg gtt act ttg ata aac gat ctt aat ggt aac cat gtg    1619
Ile Glu Gln Val Val Thr Leu Ile Asn Asp Leu Asn Gly Asn His Val
    305                 310                 315 att caa aag tgt att ttc aaa ttc tcg cca tca aaa ttt ggt ttc atc    1667
Ile Gln Lys Cys Ile Phe Lys Phe Ser Pro Ser Lys Phe Gly Phe Ile
320                 325                 330                 335 ata gat gct att gta gaa caa aat aat atc att acc att tct acc cat    1715
Ile Asp Ala Ile Val Glu Gln Asn Asn Ile Ile Thr Ile Ser Thr His
                340                 345                 350 aaa cat ggt tgt tgc gta cta caa aaa tta cta agc gtt tgt act cta    1763
Lys His Gly Cys Cys Val Leu Gln Lys Leu Leu Ser Val Cys Thr Leu
                355                 360                 365 caa caa att ttc aaa att tct gtg aaa att gtg cag ttc ctt cct gga    1811
Gln Gln Ile Phe Lys Ile Ser Val Lys Ile Val Gln Phe Leu Pro Gly
            370                 375                 380 tta atc aac gat cag ttc ggt aat tat atc atc caa ttt ctg tta gat    1859
Leu Ile Asn Asp Gln Phe Gly Asn Tyr Ile Ile Gln Phe Leu Leu Asp
385                 390                 395 atc aaa gaa ttg gac ttt tac tta ttg gct gag tta ttt aac cgt tta    1907
Ile Lys Glu Leu Asp Phe Tyr Leu Leu Ala Glu Leu Phe Asn Arg Leu
400                 405                 410                 415 tcc aat gaa tta tgt caa cta tct tgt ttg aag ttc tcc tca aat gtt    1955
Ser Asn Glu Leu Cys Gln Leu Ser Cys Leu Lys Phe Ser Ser Asn Val
                420                 425                 430 gtg gaa aaa ttc att aaa aaa tta ttt aga atc att act gga ttt att    2003
Val Glu Lys Phe Ile Lys Lys Leu Phe Arg Ile Ile Thr Gly Phe Ile
                435                 440                 445 gtt aat aac aat ggg ggt gcc tcc caa agg act gca gtt gct tct gat    2051
Val Asn Asn Asn Gly Gly Ala Ser Gln Arg Thr Ala Val Ala Ser Asp
            450                 455                 460 gac gtg att aat gct tct atg aac att ctt ttg act acc att gat ata    2099
Asp Val Ile Asn Ala Ser Met Asn Ile Leu Leu Thr Thr Ile Asp Ile
465                 470                 475 ttc aca gtc aat tta aat gtg cta atc agg gat aat ttt ggt aat tat    2147
Phe Thr Val Asn Leu Asn Val Leu Ile Arg Asp Asn Phe Gly Asn Tyr
480                 485                 490                 495 gcg tta caa acg cta tta gac gtt aag aat tat tct cct ctg ctt gct    2195
Ala Leu Gln Thr Leu Leu Asp Val Lys Asn Tyr Ser Pro Leu Leu Ala
                500                 505                 510 tac aac aaa aat agt aac gca att ggg caa aac agc tct agt aca ttg    2243
Tyr Asn Lys Asn Ser Asn Ala Ile Gly Gln Asn Ser Ser Ser Thr Leu
                515                 520                 525 aat tac ggt aac ttt tgt aac gat ttt tca ttg aaa att ggt aac ttg    2291
Asn Tyr Gly Asn Phe Cys Asn Asp Phe Ser Leu Lys Ile Gly Asn Leu
            530                 535                 540 att gtc ctt aca aaa gaa tta ctt cca agt att aaa act aca tcc tat    2339
Ile Val Leu Thr Lys Glu Leu Leu Pro Ser Ile Lys Thr Thr Ser Tyr
545                 550                 555 gca aag aaa att aag ttg aaa gtt aaa gct tat gca gaa gcc aca ggt    2387
Ala Lys Lys Ile Lys Leu Lys Val Lys Ala Tyr Ala Glu Ala Thr Gly
560                 565                 570                 575 ata cca ttc act gac ata tct cct caa gtc act gca atg agt cat aac    2435
Ile Pro Phe Thr Asp Ile Ser Pro Gln Val Thr Ala Met Ser His Asn
                580                 585                 590 aat ctt caa acg att aac aac gaa aat aag aac ccc cat aac aaa aat    2483
Asn Leu Gln Thr Ile Asn Asn Glu Asn Lys Asn Pro His Asn Lys Asn
                595                 600                 605 agt cat aat cat aat cat aat cat aat cat aac cat gct cac aat aat    2531
Ser His Asn His Asn His Asn His Asn His Asn His Ala His Asn Asn
            610                 615                 620
```

```
aat aac aat aat aat caa aag agt cat acc cgt cat ttt tct tta cca    2579
Asn Asn Asn Asn Asn Gln Lys Ser His Thr Arg His Phe Ser Leu Pro
            625                 630                 635 gct aat gct tac cat aga aga agt aac agc tct gta acc aat aat ttc    2627
Ala Asn Ala Tyr His Arg Arg Ser Asn Ser Ser Val Thr Asn Asn Phe
640                 645                 650                 655 tca aac caa tat gca caa gat cag aaa att cac tct ccg caa caa att    2675
Ser Asn Gln Tyr Ala Gln Asp Gln Lys Ile His Ser Pro Gln Gln Ile
                660                 665                 670 atg aac ttc aac caa aac gca tat ccc tcg atg gga gca cct tct ttc    2723
Met Asn Phe Asn Gln Asn Ala Tyr Pro Ser Met Gly Ala Pro Ser Phe
            675                 680                 685 aat tct caa act aac cca cca ttg gta agc cat aac tcg tta caa aac    2771
Asn Ser Gln Thr Asn Pro Pro Leu Val Ser His Asn Ser Leu Gln Asn
        690                 695                 700 ttc gac aac cgc cag ttt gca aat tta atg gca cat cct aat tct gct    2819
Phe Asp Asn Arg Gln Phe Ala Asn Leu Met Ala His Pro Asn Ser Ala
705                 710                 715 gca cca atc cat tcg ttc tca tca tct aac att acc aat gtg aat cct    2867
Ala Pro Ile His Ser Phe Ser Ser Ser Asn Ile Thr Asn Val Asn Pro
720                 725                 730                 735 aat gtt tca agg gga ttt aag cag cct gga ttt atg atg aat gaa acc    2915
Asn Val Ser Arg Gly Phe Lys Gln Pro Gly Phe Met Met Asn Glu Thr
                740                 745                 750 gac aaa att aat gct aat cac ttc tcg cca tac tct aat gca aat agt    2963
Asp Lys Ile Asn Ala Asn His Phe Ser Pro Tyr Ser Asn Ala Asn Ser
            755                 760                 765 caa aac ttc aat gaa tct ttt gtg cct cgt atg caa tat caa acg gaa    3011
Gln Asn Phe Asn Glu Ser Phe Val Pro Arg Met Gln Tyr Gln Thr Glu
        770                 775                 780 ggt gca aac tgg gat tca agt ttg tca atg aag tcg cag cat att ggt    3059
Gly Ala Asn Trp Asp Ser Ser Leu Ser Met Lys Ser Gln His Ile Gly
785                 790                 795 caa ggc cca tat aat caa gtt aat atg agc cgc aac gct agt att tcc    3107
Gln Gly Pro Tyr Asn Gln Val Asn Met Ser Arg Asn Ala Ser Ile Ser
800                 805                 810                 815 aat atg cct gcc atg aat acc gct aga aca tct gat gaa ctt caa ttc    3155
Asn Met Pro Ala Met Asn Thr Ala Arg Thr Ser Asp Glu Leu Gln Phe
                820                 825                 830 act ttg cca taatactttt ttttctttct ttttcttccc ttcttactgt            3204
Thr Leu Pro acaaatattt tacgcagaaa tcaaagacaa agaaaaata aaaataaaa aataaaaat     3264 tcaactaagc aatgacgtcc tactaaagtc ccaaatttg agccggaaaa aaatggtaaa   3324
gcaaactatt gccatcttta tattttgtat tctgtttccg aacacgtatc caaaatcctc  3384
ccactgcctt tgcagggtta gcattgctcc ctaccaaaat gatctaattt ttttttgaat  3444
cgttttttgt c                                                      3455

<210> SEQ ID NO 4
<211> LENGTH: 834
<212> TYPE: PRT
<213> ORGANISM: Saccharomyces cerevisiae

<400> SEQUENCE: 4

Met Ser Tyr Asn His Gln Pro Gln Leu Ser Ile Asn Ser Val Gln Ser
1               5                   10                  15

Leu Leu Glu Pro Val Thr Pro Pro Leu Gly Gln Met Asn Asn Lys
            20                  25                  30
```

-continued

Arg Asn His Gln Lys Ala His Ser Leu Asp Leu Ser Gly Phe Asn Gln
            35                  40                  45

Phe Ile Ser Ser Thr Gln Ser Pro Leu Ala Leu Met Asn Asn Thr Ser
    50                  55                  60

Thr Ser Asn Ser Ala Asn Ser Phe Ser Pro Asn Pro Asn Ala Ala Ser
65                  70                  75                  80

Asn Ser Thr Gly Leu Ser Ala Ser Met Ala Asn Pro Ala Ile Leu
                85                  90                  95

Pro Leu Ile Asn Glu Phe Asp Leu Glu Met Asp Gly Pro Arg Arg Lys
            100                 105                 110

Ser Ser His Asp Phe Thr Val Val Ala Pro Ser Asn Ser Gly Val Asn
            115                 120                 125

Thr Ser Ser Leu Ile Met Glu Thr Pro Ser Ser Ser Val Thr Pro Ala
            130                 135                 140

Ala Ser Leu Arg Asn Phe Ser Asn Ser Asn Asn Ala Ala Ser Lys Cys
145                 150                 155                 160

Gly Val Asp Asn Ser Ser Phe Gly Leu Ser Ser Ser Thr Ser Ser Ser
                165                 170                 175

Met Val Glu Ile Ser Ala Leu Pro Leu Arg Asp Leu Asp Tyr Ile Lys
            180                 185                 190

Leu Ala Thr Asp Gln Phe Gly Cys Arg Phe Leu Gln Lys Lys Leu Glu
            195                 200                 205

Thr Pro Ser Glu Ser Asn Met Val Arg Asp Leu Met Tyr Glu Gln Ile
            210                 215                 220

Lys Pro Phe Phe Leu Asp Leu Ile Leu Asp Pro Phe Gly Asn Tyr Leu
225                 230                 235                 240

Val Gln Lys Leu Cys Asp Tyr Leu Thr Ala Glu Gln Lys Thr Leu Leu
                245                 250                 255

Ile Gln Thr Ile Tyr Pro Asn Val Phe Gln Ile Ser Ile Asn Gln Tyr
            260                 265                 270

Gly Thr Arg Ser Leu Gln Lys Ile Ile Asp Thr Val Asp Asn Glu Val
            275                 280                 285

Gln Ile Asp Leu Ile Ile Lys Gly Phe Ser Gln Glu Phe Thr Ser Ile
            290                 295                 300

Glu Gln Val Val Thr Leu Ile Asn Asp Leu Asn Gly Asn His Val Ile
305                 310                 315                 320

Gln Lys Cys Ile Phe Lys Phe Ser Pro Ser Lys Phe Gly Phe Ile Ile
                325                 330                 335

Asp Ala Ile Val Glu Gln Asn Asn Ile Thr Ile Ser Thr His Lys
            340                 345                 350

His Gly Cys Cys Val Leu Gln Lys Leu Leu Ser Val Cys Thr Leu Gln
            355                 360                 365

Gln Ile Phe Lys Ile Ser Val Lys Ile Val Gln Phe Leu Pro Gly Leu
            370                 375                 380

Ile Asn Asp Gln Phe Gly Asn Tyr Ile Ile Gln Phe Leu Leu Asp Ile
385                 390                 395                 400

Lys Glu Leu Asp Phe Tyr Leu Leu Ala Glu Leu Phe Asn Arg Leu Ser
                405                 410                 415

Asn Glu Leu Cys Gln Leu Ser Cys Leu Lys Phe Ser Ser Asn Val Val
            420                 425                 430

Glu Lys Phe Ile Lys Lys Leu Phe Arg Ile Ile Thr Gly Phe Ile Val
            435                 440                 445

```
Asn Asn Asn Gly Gly Ala Ser Gln Arg Thr Ala Val Ala Ser Asp Asp
    450                 455                 460

Val Ile Asn Ala Ser Met Asn Ile Leu Leu Thr Thr Ile Asp Ile Phe
465                 470                 475                 480

Thr Val Asn Leu Asn Val Leu Ile Arg Asp Asn Phe Gly Asn Tyr Ala
                485                 490                 495

Leu Gln Thr Leu Leu Asp Val Lys Asn Tyr Ser Pro Leu Leu Ala Tyr
            500                 505                 510

Asn Lys Asn Ser Asn Ala Ile Gly Gln Asn Ser Ser Thr Leu Asn
            515                 520                 525

Tyr Gly Asn Phe Cys Asn Asp Phe Ser Leu Lys Ile Gly Asn Leu Ile
    530                 535                 540

Val Leu Thr Lys Glu Leu Leu Pro Ser Ile Lys Thr Thr Ser Tyr Ala
545                 550                 555                 560

Lys Lys Ile Lys Leu Lys Val Lys Ala Tyr Ala Glu Ala Thr Gly Ile
                565                 570                 575

Pro Phe Thr Asp Ile Ser Pro Gln Val Thr Ala Met Ser His Asn Asn
            580                 585                 590

Leu Gln Thr Ile Asn Asn Glu Asn Lys Asn Pro His Asn Lys Asn Ser
            595                 600                 605

His Asn His Asn His Asn His Asn His Ala His Asn Asn Asn
    610                 615                 620

Asn Asn Asn Asn Gln Lys Ser His Thr Arg His Phe Ser Leu Pro Ala
625                 630                 635                 640

Asn Ala Tyr His Arg Arg Ser Asn Ser Ser Val Thr Asn Asn Phe Ser
                645                 650                 655

Asn Gln Tyr Ala Gln Asp Gln Lys Ile His Ser Pro Gln Gln Ile Met
            660                 665                 670

Asn Phe Asn Gln Asn Ala Tyr Pro Ser Met Gly Ala Pro Ser Phe Asn
    675                 680                 685

Ser Gln Thr Asn Pro Pro Leu Val Ser His Asn Ser Leu Gln Asn Phe
    690                 695                 700

Asp Asn Arg Gln Phe Ala Asn Leu Met Ala His Pro Asn Ser Ala Ala
705                 710                 715                 720

Pro Ile His Ser Phe Ser Ser Asn Ile Thr Asn Val Asn Pro Asn
                725                 730                 735

Val Ser Arg Gly Phe Lys Gln Pro Gly Phe Met Met Asn Glu Thr Asp
            740                 745                 750

Lys Ile Asn Ala Asn His Phe Ser Pro Tyr Ser Asn Ala Asn Ser Gln
    755                 760                 765

Asn Phe Asn Glu Ser Phe Val Pro Arg Met Gln Tyr Gln Thr Glu Gly
    770                 775                 780

Ala Asn Trp Asp Ser Ser Leu Ser Met Lys Ser Gln His Ile Gly Gln
785                 790                 795                 800

Gly Pro Tyr Asn Gln Val Asn Met Ser Arg Asn Ala Ser Ile Ser Asn
                805                 810                 815

Met Pro Ala Met Asn Thr Ala Arg Thr Ser Asp Glu Leu Gln Phe Thr
            820                 825                 830

Leu Pro

<210> SEQ ID NO 5
<211> LENGTH: 4000
<212> TYPE: DNA
<213> ORGANISM: Saccharomyces cerevisiae
```

-continued

```
<220> FEATURE:
<221> NAME/KEY: CDS
<222> LOCATION: (717)...(3380)
<223> OTHER INFORMATION: YGL023

<400> SEQUENCE: 5
gtgtcttcca tggagtgaat tgtgatttgt gaattatatc tgtccaatac cgttgccttg      60
ttgggagctc agatagaaaa gacatcttaa ttccagacag tctattctct gtctatttct     120
ctttgtgact gcaaatttta atttgtgacg ccttttctta ttactcatgt atttgtcact     180
cttgacgatt gttttttttc tatatttttt ttgttctggg gtcctccaga gaataaaaaa     240
taatgatcaa tatagtagat agtatagtta tattcttatt cgttgcacct tgtttaacaa     300
atcactcaga ctcaaagaga atatcggttg gttatctctc tccgaaggtg aacagcaaac     360
agtacctcac gtctttttt tgaatagttt ttttttttgt tgaaacagaa aaaaactttc     420
                                                                     [sic]

cttccgtata ttacattgta cattattttt attgtatttt agtttccaac gttaggattt     480
gagccgtcat taatattatt cgttttgta cactattcca gacgatttat ttttagtaca      540
                                                                     [sic]

cttaaaattc ctgttgatat tgtccactag ttctctttc atattttatt ttcgcttatt      600
                                                                     [sic]

ctttaggttc ttttaagagt ctctgttcat tttccgttct tactgtttct ttgtcctcga     660
tatcttttaa gaaagagaga actaagcgct gtaacatttt taagtggacc tacgtt atg     719
                                                                    Met
                                                                     1 tct aca aaa ggt ttg aaa gaa gaa atc gat gat gta cca tca gta gac       767
Ser Thr Lys Gly Leu Lys Glu Glu Ile Asp Asp Val Pro Ser Val Asp
         5                  10                  15 cct gtc gtt tca gaa aca gtc aat tct gct tta gag cag ttg caa cta       815
Pro Val Val Ser Glu Thr Val Asn Ser Ala Leu Glu Gln Leu Gln Leu
     20                  25                  30 gat gat cca gag gaa aac gcc acc tct aat gca ttt gcg aat aaa gtt       863
Asp Asp Pro Glu Glu Asn Ala Thr Ser Asn Ala Phe Ala Asn Lys Val
 35                  40                  45 tct caa gat tct caa ttc gct aat ggc cct ccg tcg caa atg ttt cca       911
Ser Gln Asp Ser Gln Phe Ala Asn Gly Pro Pro Ser Gln Met Phe Pro
 50                  55                  60                  65 cat cca caa atg atg ggt gga atg ggc ttc atg ccc tac tct caa atg       959
His Pro Gln Met Met Gly Gly Met Gly Phe Met Pro Tyr Ser Gln Met
             70                  75                  80 atg cag gtt cct cat aat cct tgt cca ttt ttt ccg ccc cct gat ttt      1007
Met Gln Val Pro His Asn Pro Cys Pro Phe Phe Pro Pro Pro Asp Phe
         85                  90                  95 aat gat cca aca gca cca ttg agt agc tcg ccc ttg aat gca ggc ggt      1055
Asn Asp Pro Thr Ala Pro Leu Ser Ser Ser Pro Leu Asn Ala Gly Gly
     100                 105                 110 cca cca atg tta ttc aag aat gac tca ctt cca ttt caa atg ctg tct      1103
Pro Pro Met Leu Phe Lys Asn Asp Ser Leu Pro Phe Gln Met Leu Ser
 115                 120                 125 tcg ggt gct gcg gta gca act caa ggt gga caa aat cta aac cca ttg      1151
Ser Gly Ala Ala Val Ala Thr Gln Gly Gly Gln Asn Leu Asn Pro Leu
130                 135                 140                 145 ata aat gac aat tca atg aag gta ttg cca atc gca tcg gct gat ccg      1199
Ile Asn Asp Asn Ser Met Lys Val Leu Pro Ile Ala Ser Ala Asp Pro
             150                 155                 160 tta tgg act cat tca aac gta cca gga tca gca tct gta gcc att gaa      1247
Leu Trp Thr His Ser Asn Val Pro Gly Ser Ala Ser Val Ala Ile Glu
         165                 170                 175 gaa acc acc gct act cta caa gaa agc cta cca tct aag ggc agg gag      1295
Glu Thr Thr Ala Thr Leu Gln Glu Ser Leu Pro Ser Lys Gly Arg Glu
```

-continued

```
                180                 185                 190
tct aat aat aag gct agt tcg ttc aga aga caa act ttt cat gct tta         1343
Ser Asn Asn Lys Ala Ser Ser Phe Arg Arg Gln Thr Phe His Ala Leu
    195                 200                 205 tca cca act gac ctt atc aat gcg gcc aac aat gta acc ttg tca aag         1391
Ser Pro Thr Asp Leu Ile Asn Ala Ala Asn Asn Val Thr Leu Ser Lys
210                 215                 220                 225 gac ttc caa tct gac atg cag aat ttt tct aag gct aag aaa ccg tct         1439
Asp Phe Gln Ser Asp Met Gln Asn Phe Ser Lys Ala Lys Lys Pro Ser
                230                 235                 240 gta gga gct aac aat act gca aaa acc aga act caa tcc ata tct ttt         1487
Val Gly Ala Asn Asn Thr Ala Lys Thr Arg Thr Gln Ser Ile Ser Phe
            245                 250                 255 gat aat act ccc tcc tca acg tca ttt ata ccc cca acc aat agt gtt         1535
Asp Asn Thr Pro Ser Ser Thr Ser Phe Ile Pro Pro Thr Asn Ser Val
        260                 265                 270 tct gag aaa tta tcc gat ttc aaa ata gaa acc tcg aag gag gat ttg         1583
Ser Glu Lys Leu Ser Asp Phe Lys Ile Glu Thr Ser Lys Glu Asp Leu
    275                 280                 285 att aat aaa act gca cca gct aaa aaa gag agt cct aca act tat ggt         1631
Ile Asn Lys Thr Ala Pro Ala Lys Lys Glu Ser Pro Thr Thr Tyr Gly
290                 295                 300                 305 gca gca tat cca tat ggg gga cct tta ctt caa cca aat cct att atg         1679
Ala Ala Tyr Pro Tyr Gly Gly Pro Leu Leu Gln Pro Asn Pro Ile Met
                310                 315                 320 cca ggc cac cca cat aat ata tcc tcc cct atc tat ggt att aga tca         1727
Pro Gly His Pro His Asn Ile Ser Ser Pro Ile Tyr Gly Ile Arg Ser
            325                 330                 335 cct ttt cct aat tct tat gaa atg ggc gcg caa ttt caa cct ttc tct         1775
Pro Phe Pro Asn Ser Tyr Glu Met Gly Ala Gln Phe Gln Pro Phe Ser
        340                 345                 350 ccg att tta aat cct acg agt cat tca cta aat gca aat tct cca att         1823
Pro Ile Leu Asn Pro Thr Ser His Ser Leu Asn Ala Asn Ser Pro Ile
    355                 360                 365 cct cta acc caa tcg cca att cat ctt gca cca gtt tta aac cct agt         1871
Pro Leu Thr Gln Ser Pro Ile His Leu Ala Pro Val Leu Asn Pro Ser
370                 375                 380                 385 tca aat tct gtt gcc ttt tca gat atg aag aat gat ggt ggt aag ccc         1919
Ser Asn Ser Val Ala Phe Ser Asp Met Lys Asn Asp Gly Gly Lys Pro
                390                 395                 400 acc acc gat aac gac aag gcg ggt cca aat gtt agg atg gat tta ata         1967
Thr Thr Asp Asn Asp Lys Ala Gly Pro Asn Val Arg Met Asp Leu Ile
            405                 410                 415 aat cct aat ctt ggg cca tca atg caa cct ttc cac ata tta cct ccc         2015
Asn Pro Asn Leu Gly Pro Ser Met Gln Pro Phe His Ile Leu Pro Pro
        420                 425                 430 cag caa aac acc ccc cct cct ccc tgg ctt tat agc act cca cct ccc         2063
Gln Gln Asn Thr Pro Pro Pro Pro Trp Leu Tyr Ser Thr Pro Pro Pro
    435                 440                 445 ttc aac gca atg gtt ccg cct cat ttg ttg gct caa aat cat atg ccg         2111
Phe Asn Ala Met Val Pro Pro His Leu Leu Ala Gln Asn His Met Pro
450                 455                 460                 465 tta atg aat agc gcc aat aat aaa cat cat ggt cgt aat aac aat agc         2159
Leu Met Asn Ser Ala Asn Asn Lys His His Gly Arg Asn Asn Asn Ser
                470                 475                 480 atg tca agt cat aat gac aat gac aac att ggt aat tct aat tac aac         2207
Met Ser Ser His Asn Asp Asn Asp Asn Ile Gly Asn Ser Asn Tyr Asn
            485                 490                 495 aat aaa gac aca ggt cgt tct aac gtt ggt aaa atg aaa aat atg aaa         2255
```

|   |   |   |   |   |   |   |   |   |   |   |   |   |   |   |   |
|---|---|---|---|---|---|---|---|---|---|---|---|---|---|---|---|
| Asn | Lys | Asp | Thr | Gly | Arg | Ser | Asn | Val | Gly | Lys | Met | Lys | Asn | Met | Lys |
|  | 500 |  |  |  | 505 |  |  |  | 510 |  |  |  |  |  |  |

```
aac agt tat cat ggc tac tat aat aac aat aat aat aat aat aat               2303
Asn Ser Tyr His Gly Tyr Tyr Asn Asn Asn Asn Asn Asn Asn Asn
    515                 520                 525 aac aat aat aat aat aac agt aat gct acc aac agc aac agc gcg gaa           2351
Asn Asn Asn Asn Asn Asn Ser Asn Ala Thr Asn Ser Asn Ser Ala Glu
530                 535                 540                 545 aaa caa cgt aaa att gag gag tcg tcg aga ttt gcg gac gca gtt tta           2399
Lys Gln Arg Lys Ile Glu Glu Ser Ser Arg Phe Ala Asp Ala Val Leu
                550                 555                 560 gac caa tat atc gga agt att cac tca ttg tgt aaa gac caa cat ggt           2447
Asp Gln Tyr Ile Gly Ser Ile His Ser Leu Cys Lys Asp Gln His Gly
            565                 570                 575 tgt cgt ttt ctg caa aag cag ttg gat att ctc ggc agt aag gcg gcg           2495
Cys Arg Phe Leu Gln Lys Gln Leu Asp Ile Leu Gly Ser Lys Ala Ala
        580                 585                 590 gac cga att ttt gaa gaa act aag gat tat acg gtt gaa ttg atg act           2543
Asp Arg Ile Phe Glu Glu Thr Lys Asp Tyr Thr Val Glu Leu Met Thr
    595                 600                 605 gat tca ttc ggt aat tat ttg atc cag aag cta ttg gaa gag gtt acc           2591
Asp Ser Phe Gly Asn Tyr Leu Ile Gln Lys Leu Leu Glu Glu Val Thr
610                 615                 620                 625 aca gaa caa aga atc gta ctc aca aaa ata tct tcc cct cat ttt gtc           2639
Thr Glu Gln Arg Ile Val Leu Thr Lys Ile Ser Ser Pro His Phe Val
                630                 635                 640 gaa att tcc tta aac cct cat ggt act agg gca tta caa aaa ctc att           2687
Glu Ile Ser Leu Asn Pro His Gly Thr Arg Ala Leu Gln Lys Leu Ile
            645                 650                 655 gaa tgc atc aaa aca gat gaa gaa gca cag att gtt gtt gat tct tta           2735
Glu Cys Ile Lys Thr Asp Glu Glu Ala Gln Ile Val Val Asp Ser Leu
        660                 665                 670 cgc cct tat act gtc cag ttg agt aag gat tta aat ggt aat cat gtt           2783
Arg Pro Tyr Thr Val Gln Leu Ser Lys Asp Leu Asn Gly Asn His Val
    675                 680                 685 att caa aaa tgt ttg caa agg ttg aag cct gaa aac ttc cag ttt atc           2831
Ile Gln Lys Cys Leu Gln Arg Leu Lys Pro Glu Asn Phe Gln Phe Ile
690                 695                 700                 705 ttt gac gca atc tct gat agc tgt att gat att gct act cat aga cac           2879
Phe Asp Ala Ile Ser Asp Ser Cys Ile Asp Ile Ala Thr His Arg His
                710                 715                 720 ggg tgt tgc gtt ttg caa cgt tgt cta gat cat ggg act aca gaa caa           2927
Gly Cys Cys Val Leu Gln Arg Cys Leu Asp His Gly Thr Thr Glu Gln
            725                 730                 735 tgt gac aat ctg tgt gat aag ttg cta gcc ctt gtt gat aaa tta act           2975
Cys Asp Asn Leu Cys Asp Lys Leu Leu Ala Leu Val Asp Lys Leu Thr
        740                 745                 750 ttg gat cca ttt ggc aac tat gtg gtg caa tat ata att acc aaa gag           3023
Leu Asp Pro Phe Gly Asn Tyr Val Val Gln Tyr Ile Ile Thr Lys Glu
    755                 760                 765 gct gag aag aac aaa tat gat tat acg cat aaa att gtc cac ctg ttg           3071
Ala Glu Lys Asn Lys Tyr Asp Tyr Thr His Lys Ile Val His Leu Leu
770                 775                 780                 785 aaa cca aga gcc atc gaa ctt tct atc cat aaa ttt gga tca aat gtg           3119
Lys Pro Arg Ala Ile Glu Leu Ser Ile His Lys Phe Gly Ser Asn Val
                790                 795                 800 att gaa aaa atc ttg aag aca gct att gtt tcg gag cca atg att ctg           3167
Ile Glu Lys Ile Leu Lys Thr Ala Ile Val Ser Glu Pro Met Ile Leu
            805                 810                 815
```

-continued

```
gaa att tta aat aat ggt ggc gag acg ggt att caa tca ttg ttg aat    3215
Glu Ile Leu Asn Asn Gly Gly Glu Thr Gly Ile Gln Ser Leu Leu Asn
        820                 825                 830 gat agc tac gga aat tac gtt tta cag aca gca tta gac att tct cat    3263
Asp Ser Tyr Gly Asn Tyr Val Leu Gln Thr Ala Leu Asp Ile Ser His
835                 840                 845 aag caa aat gac tat ctc tat aaa aga cta tca gag att gtg gcg cct    3311
Lys Gln Asn Asp Tyr Leu Tyr Lys Arg Leu Ser Glu Ile Val Ala Pro
850                 855                 860                 865 tta ctg gtg ggc ccc ata aga aat aca cct cat ggt aaa aga atc atc    3359
Leu Leu Val Gly Pro Ile Arg Asn Thr Pro His Gly Lys Arg Ile Ile
                870                 875                 880 gga atg tta cat tta gat tca tagttgatac atatatcctc agtttagctt       3410
Gly Met Leu His Leu Asp Ser
                885 tttttacgtt agcctcatat aatatctttt gtacaatact aaaatacatc attttttttt  3470 tcgttgagga tcaaatgaat atccaaagca aaaaaaatag gaattttcac tttatggtat  3530 actggtaaat agtgttgaag aaataagaga aggagatcgc cctagaaaac agaatgttct  3590 tatttaaata agtaaactca aaagaaaaaa aaaggaagg aagttttga gaacttttat    3650 ctatacaaac gtatacgttt aactatctgg ataaacgtcg ctccacagga tactgtagag  3710 gtcctcaaga tcaccgttat taacaaattc atcagtgtc cccaaattaa aactagttgc   3770 agaaaaattg ttactgttgt tgttgttaat attgttaata ttgttttat tgttgttgtt   3830 gttgatttca tttgtgttca taaatggtac ttgtactgaa gtgggtattt gctgctgagc  3890 attgattggt ttattagatt ggacttgcga attattttgc ccatttgttg gttgcgcgta  3950 atcgggattg atcatatcag acacggataa tgacctaaat gaaggcaatt             4000
```

<210> SEQ ID NO 6
<211> LENGTH: 888
<212> TYPE: PRT
<213> ORGANISM: Saccharomyces cerevisiae

<400> SEQUENCE: 6

```
Met Ser Thr Lys Gly Leu Lys Glu Glu Ile Asp Asp Val Pro Ser Val
1               5                   10                  15

Asp Pro Val Val Ser Glu Thr Val Asn Ser Ala Leu Glu Gln Leu Gln
            20                  25                  30

Leu Asp Asp Pro Glu Glu Asn Ala Thr Ser Asn Ala Phe Ala Asn Lys
        35                  40                  45

Val Ser Gln Asp Ser Gln Phe Ala Asn Gly Pro Pro Ser Gln Met Phe
    50                  55                  60

Pro His Pro Gln Met Met Gly Gly Met Gly Phe Met Pro Tyr Ser Gln
65                  70                  75                  80

Met Met Gln Val Pro His Asn Pro Cys Pro Phe Phe Pro Pro Asp
                85                  90                  95

Phe Asn Asp Pro Thr Ala Pro Leu Ser Ser Pro Leu Asn Ala Gly
            100                 105                 110

Gly Pro Pro Met Leu Phe Lys Asn Asp Ser Leu Pro Phe Gln Met Leu
        115                 120                 125

Ser Ser Gly Ala Ala Val Ala Thr Gln Gly Gly Gln Asn Leu Asn Pro
    130                 135                 140

Leu Ile Asn Asp Asn Ser Met Lys Val Leu Pro Ile Ala Ser Ala Asp
145                 150                 155                 160

Pro Leu Trp Thr His Ser Asn Val Pro Gly Ser Ala Ser Val Ala Ile
```

-continued

```
            165                 170                 175
Glu Glu Thr Thr Ala Thr Leu Gln Ser Leu Pro Ser Lys Gly Arg
            180                 185                 190
Glu Ser Asn Asn Lys Ala Ser Ser Phe Arg Arg Gln Thr Phe His Ala
            195                 200                 205
Leu Ser Pro Thr Asp Leu Ile Asn Ala Ala Asn Asn Val Thr Leu Ser
            210                 215                 220
Lys Asp Phe Gln Ser Asp Met Gln Asn Phe Ser Lys Ala Lys Lys Pro
225                 230                 235                 240
Ser Val Gly Ala Asn Asn Thr Ala Lys Thr Arg Thr Gln Ser Ile Ser
                245                 250                 255
Phe Asp Asn Thr Pro Ser Ser Thr Ser Phe Ile Pro Pro Thr Asn Ser
                260                 265                 270
Val Ser Glu Lys Leu Ser Asp Phe Lys Ile Glu Thr Ser Lys Glu Asp
                275                 280                 285
Leu Ile Asn Lys Thr Ala Pro Ala Lys Lys Glu Ser Pro Thr Thr Tyr
            290                 295                 300
Gly Ala Ala Tyr Pro Tyr Gly Gly Pro Leu Leu Gln Pro Asn Pro Ile
305                 310                 315                 320
Met Pro Gly His Pro His Asn Ile Ser Ser Pro Ile Tyr Gly Ile Arg
                325                 330                 335
Ser Pro Phe Pro Asn Ser Tyr Glu Met Gly Ala Gln Phe Gln Pro Phe
                340                 345                 350
Ser Pro Ile Leu Asn Pro Thr Ser His Ser Leu Asn Ala Asn Ser Pro
            355                 360                 365
Ile Pro Leu Thr Gln Ser Pro Ile His Leu Ala Pro Val Leu Asn Pro
            370                 375                 380
Ser Ser Asn Ser Val Ala Phe Ser Asp Met Lys Asn Asp Gly Gly Lys
385                 390                 395                 400
Pro Thr Thr Asp Asn Asp Lys Ala Gly Pro Asn Val Arg Met Asp Leu
                405                 410                 415
Ile Asn Pro Asn Leu Gly Pro Ser Met Gln Pro Phe His Ile Leu Pro
                420                 425                 430
Pro Gln Gln Asn Thr Pro Pro Pro Trp Leu Tyr Ser Thr Pro Pro
            435                 440                 445
Pro Phe Asn Ala Met Val Pro Pro His Leu Leu Ala Gln Asn His Met
            450                 455                 460
Pro Leu Met Asn Ser Ala Asn Asn Lys His His Gly Arg Asn Asn Asn
465                 470                 475                 480
Ser Met Ser Ser His Asn Asp Asn Asp Asn Ile Gly Asn Ser Asn Tyr
                485                 490                 495
Asn Asn Lys Asp Thr Gly Arg Ser Asn Val Gly Lys Met Lys Asn Met
            500                 505                 510
Lys Asn Ser Tyr His Gly Tyr Tyr Asn Asn Asn Asn Asn Asn Asn
            515                 520                 525
Asn Asn Asn Asn Asn Asn Ser Asn Ala Thr Asn Ser Asn Ser Ala
            530                 535                 540
Glu Lys Gln Arg Lys Ile Glu Glu Ser Arg Phe Ala Asp Ala Val
545                 550                 555                 560
Leu Asp Gln Tyr Ile Gly Ser Ile His Ser Leu Cys Lys Asp Gln His
                565                 570                 575
Gly Cys Arg Phe Leu Gln Lys Gln Leu Asp Ile Leu Gly Ser Lys Ala
                580                 585                 590
```

```
Ala Asp Arg Ile Phe Glu Glu Thr Lys Asp Tyr Thr Val Glu Leu Met
            595                 600                 605

Thr Asp Ser Phe Gly Asn Tyr Leu Ile Gln Lys Leu Leu Glu Glu Val
610                 615                 620

Thr Thr Glu Gln Arg Ile Val Leu Thr Lys Ile Ser Ser Pro His Phe
625                 630                 635                 640

Val Glu Ile Ser Leu Asn Pro His Gly Thr Arg Ala Leu Gln Lys Leu
                645                 650                 655

Ile Glu Cys Ile Lys Thr Asp Glu Glu Ala Gln Ile Val Val Asp Ser
            660                 665                 670

Leu Arg Pro Tyr Thr Val Gln Leu Ser Lys Asp Leu Asn Gly Asn His
        675                 680                 685

Val Ile Gln Lys Cys Leu Gln Arg Leu Lys Pro Glu Asn Phe Gln Phe
    690                 695                 700

Ile Phe Asp Ala Ile Ser Asp Ser Cys Ile Asp Ile Ala Thr His Arg
705                 710                 715                 720

His Gly Cys Cys Val Leu Gln Arg Cys Leu Asp His Gly Thr Thr Glu
                725                 730                 735

Gln Cys Asp Asn Leu Cys Asp Lys Leu Leu Ala Leu Val Asp Lys Leu
            740                 745                 750

Thr Leu Asp Pro Phe Gly Asn Tyr Val Val Gln Tyr Ile Ile Thr Lys
        755                 760                 765

Glu Ala Glu Lys Asn Lys Tyr Asp Tyr Thr His Lys Ile Val His Leu
    770                 775                 780

Leu Lys Pro Arg Ala Ile Glu Leu Ser Ile His Lys Phe Gly Ser Asn
785                 790                 795                 800

Val Ile Glu Lys Ile Leu Lys Thr Ala Ile Val Ser Glu Pro Met Ile
                805                 810                 815

Leu Glu Ile Leu Asn Asn Gly Gly Glu Thr Gly Ile Gln Ser Leu Leu
            820                 825                 830

Asn Asp Ser Tyr Gly Asn Tyr Val Leu Gln Thr Ala Leu Asp Ile Ser
        835                 840                 845

His Lys Gln Asn Asp Tyr Leu Tyr Lys Arg Leu Ser Glu Ile Val Ala
    850                 855                 860

Pro Leu Leu Val Gly Pro Ile Arg Asn Thr Pro His Gly Lys Arg Ile
865                 870                 875                 880

Ile Gly Met Leu His Leu Asp Ser
                885

<210> SEQ ID NO 7
<211> LENGTH: 5319
<212> TYPE: DNA
<213> ORGANISM: Homo sapiens
<220> FEATURE:
<221> NAME/KEY: CDS
<222> LOCATION: (57)...(3614)
<223> OTHER INFORMATION: D43951

<400> SEQUENCE: 7
gaagatcggg gggctgaaat ccatcttcat cctaccgctc cgcccgtgtt ggtgga atg    59
                                                              Met
                                                                1 agc gtt gca tgt gtc ttg aag aga aaa gca gtg ctt tgg cag gac tct    107
Ser Val Ala Cys Val Leu Lys Arg Lys Ala Val Leu Trp Gln Asp Ser
          5                  10                  15 ttc agc ccc cac ctg aaa cat cac cct caa gaa cca gct aat ccc aac    155
```

```
                                              -continued

Phe Ser Pro His Leu Lys His His Pro Gln Glu Pro Ala Asn Pro Asn
         20                  25                  30 atg cct gtt gtt ttg aca tct gga aca ggg tcg caa gcg cag cca caa    203
Met Pro Val Val Leu Thr Ser Gly Thr Gly Ser Gln Ala Gln Pro Gln
 35                  40                  45 cca gct gca aat cag gct ctt gca gct ggg act cac tcc agc cct gtc    251
Pro Ala Ala Asn Gln Ala Leu Ala Ala Gly Thr His Ser Ser Pro Val
 50                  55                  60                  65 cca gga tct ata gga gtt gca ggc cgt tcc cag gac gac gct atg gtg    299
Pro Gly Ser Ile Gly Val Ala Gly Arg Ser Gln Asp Asp Ala Met Val
             70                  75                  80 gac tac ttc ttt cag agg cag cat ggt gag cag ctt ggg gga gga gga    347
Asp Tyr Phe Phe Gln Arg Gln His Gly Glu Gln Leu Gly Gly Gly Gly
                 85                  90                  95 agt gga gga ggc ggc tat aat aat agc aaa cat cga tgg cct act ggg    395
Ser Gly Gly Gly Gly Tyr Asn Asn Ser Lys His Arg Trp Pro Thr Gly
        100                 105                 110 gat aac att cat gca gaa cat cag gtg cgt tcc atg gat gaa ctg aat    443
Asp Asn Ile His Ala Glu His Gln Val Arg Ser Met Asp Glu Leu Asn
        115                 120                 125 cat gat ttt caa gca ctt gct ctg gag gga aga gcg atg gga gag cag    491
His Asp Phe Gln Ala Leu Ala Leu Glu Gly Arg Ala Met Gly Glu Gln
130                 135                 140                 145 ctc ttg cca ggt aaa aag ttt tgg gaa aca gat gaa tcc agc aaa gat    539
Leu Leu Pro Gly Lys Lys Phe Trp Glu Thr Asp Glu Ser Ser Lys Asp
                150                 155                 160 gga cca aaa gga ata ttc ctg ggt gat caa tgg cga gac agt gcc tgg    587
Gly Pro Lys Gly Ile Phe Leu Gly Asp Gln Trp Arg Asp Ser Ala Trp
            165                 170                 175 gga aca tca gat cat tca gtt tcc cag cca atc atg gtg cag aga aga    635
Gly Thr Ser Asp His Ser Val Ser Gln Pro Ile Met Val Gln Arg Arg
        180                 185                 190 cct ggt cag agt ttc cat gtg aac agt gag gtc aat tct gta ctg tcc    683
Pro Gly Gln Ser Phe His Val Asn Ser Glu Val Asn Ser Val Leu Ser
    195                 200                 205 cca cga tcg gag agt ggg gga cta ggc gtt agc atg gtg gag tat gtg    731
Pro Arg Ser Glu Ser Gly Gly Leu Gly Val Ser Met Val Glu Tyr Val
210                 215                 220                 225 ttg agc tca tcc ccg ggc gat tcc tgt cta aga aaa gga gga ttt ggc    779
Leu Ser Ser Ser Pro Gly Asp Ser Cys Leu Arg Lys Gly Gly Phe Gly
                230                 235                 240 cca agg gat gca gac agt gat gaa aac gac aaa ggt gaa aag aag aac    827
Pro Arg Asp Ala Asp Ser Asp Glu Asn Asp Lys Gly Glu Lys Lys Asn
            245                 250                 255 aag ggt acg ttt gat gga gat aag cta gga gat ttg aag gag gag ggt    875
Lys Gly Thr Phe Asp Gly Asp Lys Leu Gly Asp Leu Lys Glu Glu Gly
        260                 265                 270 gat gtg atg gac aag acc aat ggt tta cca gtg cag aat ggg att gat    923
Asp Val Met Asp Lys Thr Asn Gly Leu Pro Val Gln Asn Gly Ile Asp
    275                 280                 285 gca gac gtc aaa gat ttt agc cgt acc cct ggt aat tgc cag aac tct    971
Ala Asp Val Lys Asp Phe Ser Arg Thr Pro Gly Asn Cys Gln Asn Ser
290                 295                 300                 305 gct aat gaa gtg gat ctt ctg ggt cca aac cag aat ggt tct gag ggc    1019
Ala Asn Glu Val Asp Leu Leu Gly Pro Asn Gln Asn Gly Ser Glu Gly
                310                 315                 320 tta gcc cag ctg acc agc acc aat ggt gcc aag cct gtg gag gat ttc    1067
Leu Ala Gln Leu Thr Ser Thr Asn Gly Ala Lys Pro Val Glu Asp Phe
            325                 330                 335
```

```
                                                    -continued tcc aac atg gag tcc cag agt gtc ccc ttg gac ccc atg gaa cat gtg      1115
Ser Asn Met Glu Ser Gln Ser Val Pro Leu Asp Pro Met Glu His Val
        340                 345                 350 ggc atg gag cct ctt cag ttt gat tat tca ggc acg cag gta cct gtg      1163
Gly Met Glu Pro Leu Gln Phe Asp Tyr Ser Gly Thr Gln Val Pro Val
355                 360                 365 gac tca gca gca gca act gtg gga ctt ttt gac tac aat tct caa caa      1211
Asp Ser Ala Ala Ala Thr Val Gly Leu Phe Asp Tyr Asn Ser Gln Gln
370                 375                 380                 385 cag ctg ttc caa aga cct aat gcg ctt gct gtc cag cag ttg aca gct      1259
Gln Leu Phe Gln Arg Pro Asn Ala Leu Ala Val Gln Gln Leu Thr Ala
                390                 395                 400 gct cag cag cag cag tat gca ctg gca gct gct cat cag ccg cac atc      1307
Ala Gln Gln Gln Gln Tyr Ala Leu Ala Ala Ala His Gln Pro His Ile
            405                 410                 415 ggt tta gct ccc gct gcg ttt gtc ccc aat cca tac atc atc agc gct      1355
Gly Leu Ala Pro Ala Ala Phe Val Pro Asn Pro Tyr Ile Ile Ser Ala
        420                 425                 430 gct ccc cca ggg acg gac ccc tac aca gct gga ttg gct gca gca gcg      1403
Ala Pro Pro Gly Thr Asp Pro Tyr Thr Ala Gly Leu Ala Ala Ala Ala
435                 440                 445 aca cta ggc cca gct gtg gtc cct cac cag tat tat gga gtt act ccc      1451
Thr Leu Gly Pro Ala Val Val Pro His Gln Tyr Tyr Gly Val Thr Pro
450                 455                 460                 465 tgg gga gtc tac cct gcc agt ctt ttc cag cag caa gct gcc gct gcc      1499
Trp Gly Val Tyr Pro Ala Ser Leu Phe Gln Gln Gln Ala Ala Ala Ala
                470                 475                 480 gct gca gca act aat tca gct aat caa cag acc acc cca cag gct cag      1547
Ala Ala Ala Thr Asn Ser Ala Asn Gln Gln Thr Thr Pro Gln Ala Gln
            485                 490                 495 caa gga cag cag cag gtt ctc cgt gga gga gcc agc caa cgt cct ttg      1595
Gln Gly Gln Gln Gln Val Leu Arg Gly Gly Ala Ser Gln Arg Pro Leu
        500                 505                 510 acc cca aac cag aac cag cag gga cag caa acg gat ccc ctt gtg gca      1643
Thr Pro Asn Gln Asn Gln Gln Gly Gln Gln Thr Asp Pro Leu Val Ala
515                 520                 525 gct gca gca gtg aat tct gcc ctt gca ttt gga caa ggt ctg gca gca      1691
Ala Ala Ala Val Asn Ser Ala Leu Ala Phe Gly Gln Gly Leu Ala Ala
530                 535                 540                 545 ggc atg cca ggt tat ccg gtg ttg gct cct gct gct tac tat gac caa      1739
Gly Met Pro Gly Tyr Pro Val Leu Ala Pro Ala Ala Tyr Tyr Asp Gln
                550                 555                 560 act ggt gcc ctt gta gtg aat gca ggc gcg aga aat ggt ctt gga gct      1787
Thr Gly Ala Leu Val Val Asn Ala Gly Ala Arg Asn Gly Leu Gly Ala
            565                 570                 575 cct gtt cga ctt gta gct cct gcc cca gtc atc att agt tcc tca gct      1835
Pro Val Arg Leu Val Ala Pro Ala Pro Val Ile Ile Ser Ser Ser Ala
        580                 585                 590 gca caa gca gct gtt gca gca gcc gca gct tca gca aat gga gca gct      1883
Ala Gln Ala Ala Val Ala Ala Ala Ala Ser Ala Asn Gly Ala Ala
595                 600                 605 ggt ggt ctt gct gga aca aca aat gga cca ttt cgc cct tta gga aca      1931
Gly Gly Leu Ala Gly Thr Thr Asn Gly Pro Phe Arg Pro Leu Gly Thr
610                 615                 620                 625 cag cag cct cag ccc cag ccc cag cag ccc aat aac aac ctg gca          1979
Gln Gln Pro Gln Pro Gln Pro Gln Gln Pro Asn Asn Asn Leu Ala
                630                 635                 640 tcc agt tct ttc tac ggc aac aac tct ctg aac agc aat tca cag agc      2027
Ser Ser Ser Phe Tyr Gly Asn Asn Ser Leu Asn Ser Asn Ser Gln Ser
            645                 650                 655
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| agc | tcc | ctc | ttc | tcc | cag | ggc | tct | gcc | cag | cct | gcc | aac | aca | tcc | ttg | 2075 |
| Ser | Ser | Leu | Phe | Ser | Gln | Gly | Ser | Ala | Gln | Pro | Ala | Asn | Thr | Ser | Leu |      |
|     |     | 660 |     |     |     | 665 |     |     |     | 670 |     |     |     |     |     |      |
| gga | ttc | gga | agt | agc | agt | tct | ctc | ggc | gcc | acc | ctg | gga | tcc | gcc | ctt | 2123 |
| Gly | Phe | Gly | Ser | Ser | Ser | Ser | Leu | Gly | Ala | Thr | Leu | Gly | Ser | Ala | Leu |      |
|     | 675 |     |     |     |     | 680 |     |     |     |     | 685 |     |     |     |     |      |
| gga | ggg | ttt | gga | aca | gca | gtt | gca | aac | tcc | aac | act | ggc | agt | ggc | tcc | 2171 |
| Gly | Gly | Phe | Gly | Thr | Ala | Val | Ala | Asn | Ser | Asn | Thr | Gly | Ser | Gly | Ser |      |
| 690 |     |     |     |     | 695 |     |     |     |     | 700 |     |     |     |     | 705 |      |
| cgc | cgt | gac | tcc | ctg | act | ggc | agc | agt | gac | ctt | tat | aag | agg | aca | tcg | 2219 |
| Arg | Arg | Asp | Ser | Leu | Thr | Gly | Ser | Ser | Asp | Leu | Tyr | Lys | Arg | Thr | Ser |      |
|     |     |     |     | 710 |     |     |     |     | 715 |     |     |     |     | 720 |     |      |
| agc | agc | ttg | acc | ccc | att | gga | cac | agt | ttt | tat | aac | ggc | ctt | agc | ttt | 2267 |
| Ser | Ser | Leu | Thr | Pro | Ile | Gly | His | Ser | Phe | Tyr | Asn | Gly | Leu | Ser | Phe |      |
|     |     |     |     | 725 |     |     |     |     | 730 |     |     |     |     | 735 |     |      |
| tcc | tcc | tct | cct | gga | ccc | gtg | ggc | atg | cct | ctc | cct | agt | cag | gga | cca | 2315 |
| Ser | Ser | Ser | Pro | Gly | Pro | Val | Gly | Met | Pro | Leu | Pro | Ser | Gln | Gly | Pro |      |
|     |     |     | 740 |     |     |     |     | 745 |     |     |     |     | 750 |     |     |      |
| gga | cat | tca | cag | aca | cca | cct | cct | tcc | ctc | tct | tca | cat | gga | tcc | tct | 2363 |
| Gly | His | Ser | Gln | Thr | Pro | Pro | Pro | Ser | Leu | Ser | Ser | His | Gly | Ser | Ser |      |
|     |     | 755 |     |     |     |     | 760 |     |     |     |     | 765 |     |     |     |      |
| tca | agc | tta | aac | ctg | gga | gga | ctc | acg | aat | ggc | agt | gga | aga | tac | atc | 2411 |
| Ser | Ser | Leu | Asn | Leu | Gly | Gly | Leu | Thr | Asn | Gly | Ser | Gly | Arg | Tyr | Ile |      |
| 770 |     |     |     |     | 775 |     |     |     |     | 780 |     |     |     |     | 785 |      |
| tct | gct | gct | cca | ggc | gct | gaa | gcc | aag | tac | cgc | agt | gca | agc | agc | gcc | 2459 |
| Ser | Ala | Ala | Pro | Gly | Ala | Glu | Ala | Lys | Tyr | Arg | Ser | Ala | Ser | Ser | Ala |      |
|     |     |     |     | 790 |     |     |     |     | 795 |     |     |     |     | 800 |     |      |
| tcc | agc | ctc | ttc | agc | ccg | agc | agc | act | ctt | ttc | tct | tcc | tct | cgt | ttg | 2507 |
| Ser | Ser | Leu | Phe | Ser | Pro | Ser | Ser | Thr | Leu | Phe | Ser | Ser | Ser | Arg | Leu |      |
|     |     |     | 805 |     |     |     |     | 810 |     |     |     |     | 815 |     |     |      |
| cga | tat | gga | atg | tct | gat | gtc | atg | cct | tct | ggc | agg | agc | agg | ctt | ttg | 2555 |
| Arg | Tyr | Gly | Met | Ser | Asp | Val | Met | Pro | Ser | Gly | Arg | Ser | Arg | Leu | Leu |      |
|     |     | 820 |     |     |     |     | 825 |     |     |     |     | 830 |     |     |     |      |
| gaa | gat | ttt | cga | aac | aac | cgg | tac | ccc | aat | tta | caa | ctg | cgg | gag | att | 2603 |
| Glu | Asp | Phe | Arg | Asn | Asn | Arg | Tyr | Pro | Asn | Leu | Gln | Leu | Arg | Glu | Ile |      |
| 835 |     |     |     |     | 840 |     |     |     |     | 845 |     |     |     |     |     |      |
| gct | gga | cat | ata | atg | gaa | ttt | tcc | caa | gac | cag | cat | ggg | tcc | aga | ttc | 2651 |
| Ala | Gly | His | Ile | Met | Glu | Phe | Ser | Gln | Asp | Gln | His | Gly | Ser | Arg | Phe |      |
| 850 |     |     |     |     | 855 |     |     |     |     | 860 |     |     |     |     | 865 |      |
| att | cag | ctg | aaa | ctg | gag | cgt | gcc | aca | cca | gct | gag | cgc | cag | ctt | gtc | 2699 |
| Ile | Gln | Leu | Lys | Leu | Glu | Arg | Ala | Thr | Pro | Ala | Glu | Arg | Gln | Leu | Val |      |
|     |     |     | 870 |     |     |     |     | 875 |     |     |     |     | 880 |     |     |      |
| ttc | aat | gaa | atc | ctc | cag | gct | gcc | tac | caa | ctc | atg | gtg | gat | gtg | ttt | 2747 |
| Phe | Asn | Glu | Ile | Leu | Gln | Ala | Ala | Tyr | Gln | Leu | Met | Val | Asp | Val | Phe |      |
|     |     |     |     | 885 |     |     |     |     | 890 |     |     |     |     | 895 |     |      |
| ggt | aat | tac | gtc | att | cag | aag | ttc | ttt | gaa | ttt | ggc | agt | ctt | gaa | cag | 2795 |
| Gly | Asn | Tyr | Val | Ile | Gln | Lys | Phe | Phe | Glu | Phe | Gly | Ser | Leu | Glu | Gln |      |
|     |     | 900 |     |     |     |     | 905 |     |     |     |     | 910 |     |     |     |      |
| aag | ctg | gct | ttg | gca | gaa | cgg | att | cga | ggc | cac | gtc | ctg | tca | ttg | gca | 2843 |
| Lys | Leu | Ala | Leu | Ala | Glu | Arg | Ile | Arg | Gly | His | Val | Leu | Ser | Leu | Ala |      |
|     | 915 |     |     |     |     | 920 |     |     |     |     | 925 |     |     |     |     |      |
| cta | cag | atg | tat | ggc | tgc | cgt | gtt | atc | cag | aaa | gct | ctt | gag | ttt | att | 2891 |
| Leu | Gln | Met | Tyr | Gly | Cys | Arg | Val | Ile | Gln | Lys | Ala | Leu | Glu | Phe | Ile |      |
| 930 |     |     |     |     | 935 |     |     |     |     | 940 |     |     |     |     | 945 |      |
| cct | tca | gac | cag | cag | aat | gag | atg | gtt | cgg | gaa | cta | gat | ggc | cat | gtc | 2939 |
| Pro | Ser | Asp | Gln | Gln | Asn | Glu | Met | Val | Arg | Glu | Leu | Asp | Gly | His | Val |      |
|     |     |     |     | 950 |     |     |     |     | 955 |     |     |     |     | 960 |     |      |
| ttg | aag | tgt | gtg | aaa | gat | cag | aat | ggc | aat | cac | gtg | gtt | cag | aaa | tgc | 2987 |
| Leu | Lys | Cys | Val | Lys | Asp | Gln | Asn | Gly | Asn | His | Val | Val | Gln | Lys | Cys |      |

-continued

```
                965                 970                 975
att gaa tgt gta cag ccc cag tct ttg caa ttt atc atc gat gcg ttt    3035
Ile Glu Cys Val Gln Pro Gln Ser Leu Gln Phe Ile Ile Asp Ala Phe
        980                 985                 990 aag gga cag gta ttt gcc tta tcc aca cat cct tat ggc tgc cga gtg    3083
Lys Gly Gln Val Phe Ala Leu Ser Thr His Pro Tyr Gly Cys Arg Val
995                 1000                1005 att cag aga atc ctg gag cac tgt ctc cct gac cag aca ctc cct att    3131
Ile Gln Arg Ile Leu Glu His Cys Leu Pro Asp Gln Thr Leu Pro Ile
    1010                1015                1020                1025 tta gag gag ctt cac cag cac aca gag cag ctt gta cag gat caa tat    3179
Leu Glu Glu Leu His Gln His Thr Glu Gln Leu Val Gln Asp Gln Tyr
                1030                1035                1040 gga aat tat gta atc caa cat gta ctg gag cac ggt cgt cct gag gat    3227
Gly Asn Tyr Val Ile Gln His Val Leu Glu His Gly Arg Pro Glu Asp
            1045                1050                1055 aaa agc aaa att gta gca gaa atc cga ggc aat gta ctt gta ttg agt    3275
Lys Ser Lys Ile Val Ala Glu Ile Arg Gly Asn Val Leu Val Leu Ser
        1060                1065                1070 cag cac aaa ttt gca agc aat gtt gtg gag aag tgt gtt act cac gcc    3323
Gln His Lys Phe Ala Ser Asn Val Val Glu Lys Cys Val Thr His Ala
    1075                1080                1085 tca cgt acg gag cgc gct gtg ctc atc gat gag gtg tgc acc atg aac    3371
Ser Arg Thr Glu Arg Ala Val Leu Ile Asp Glu Val Cys Thr Met Asn
1090                1095                1100                1105 gac ggt ccc cac agt gcc tta tac acc atg atg aag gac cag tat gcc    3419
Asp Gly Pro His Ser Ala Leu Tyr Thr Met Met Lys Asp Gln Tyr Ala
                1110                1115                1120 aac tac gtg gtc cag aag atg att gac gtg gcg gag cca ggc cag cgg    3467
Asn Tyr Val Val Gln Lys Met Ile Asp Val Ala Glu Pro Gly Gln Arg
            1125                1130                1135 aag atc gtc atg cat aag atc cgg ccc cac atc gca act ctt cgt aag    3515
Lys Ile Val Met His Lys Ile Arg Pro His Ile Ala Thr Leu Arg Lys
        1140                1145                1150 tac acc tat ggc aag cac att ctg gcc aag ctg gag aag tac tac atg    3563
Tyr Thr Tyr Gly Lys His Ile Leu Ala Lys Leu Glu Lys Tyr Tyr Met
    1155                1160                1165 aag aac ggt gtt gac tta ggg ccc atc tgt ggc ccc cct aat ggt atc    3611
Lys Asn Gly Val Asp Leu Gly Pro Ile Cys Gly Pro Pro Asn Gly Ile
1170                1175                1180                1185 atc tgaggcagtg tcacccgctg ttccctcatt cccgctgacc tcactggccc         3664
Ile actggcaaat ccaaccagca accagaaatg ttctagtgta gagtctgaga cgggcaagtg   3724
gttgctccag gattactccc tcctccaaaa aaggaatcaa atccacgagt ggaaaagcct   3784
ttgtaaattt aatttttatta cacataacat gtactatttt ttttaattga ctaattgccc  3844
tgctgtttta ctggtgtata ggatacttgt acataggtaa ccaatgtaca tgggaggcca   3904
catattttgt tcactgttgt atctatattt cacatgtgga aactttcagg gtggttggtt   3964
taacaaaaaa aaaaagcttt aaaaaaaaaa gaaaaaaagg aaaaggtttt tagctcattt   4024
gcctggccgg caagttttgc aaatagctct tccccacctc ctcatttttag taaaaaacaa  4084 acaaaaacaa aaaacctga gaagtttgaa ttgtagttaa atgacccaa actggcattt    4144 aacactgttt ataaaaaata tatatatata tatatatata taatgaaaaa ggtttcagag   4204
ttgctaaagc ttcagtttgt gacattaagt ttatgaaatt ctaaaaaatg cctttttttgg  4264 agactatatt atgctgaaga aggctgttcg tgaggaggag atgcgagcac ccagaacgtc   4324
```

-continued

```
ttttgaggct gggcgggtgt gattgtttac tgcctactgg attttttttct attaacattg    4384 aaaggtaaaa tctgattatt tagcatgaga aaaaaaatcc aactctgctt ttggtcttgc    4444
ttctataaat atatagtgta tacttggtgt agactttgca tatatacaaa tttgtagtat    4504
tttcttgttt tgatgtctaa tctgtatcta aatgtaccc tagtagtcga acatactttt    4564
gattgtacaa ttgtacattt gtatacctgt aatgtaaatg tggagaagtt tgaatcaaca    4624
taaacacgtt ttttggtaag aaaagagaat tagccagccc tgtgcattca gtgtatattc    4684 tcaccttta tggtcgtagc atatagtgtt gtatattgta aattgtaatt tcaaccagaa    4744 gtaaatttt ttgtttgaa ggataaaatg ttctttatac agcctagtta atgtttaaaa    4804
agaaaaaaat agcttggttt tatttgtcat ctagtctcaa gtatagcgag attctttcta    4864
aatgttattc aagattgagt tctcactagt gttttttaa tcctaaaaaaa gtaatgtttt    4924 gattttgtga cagtcaaaag gacgtgcaaa agtctagcct tgcccgagct ttccttacaa    4984
tcagagcccc tctcaccttg taaagtgtga atcgcccttc ccttttgtac agaagatgaa    5044
ctgtattttg cattttgtct acttgtaagt gaatgtaaca tactgtcaat tttccttgtt    5104
tgaatataga attgtaacac tacacggtgt acatttccag agccttgtgt atatttccaa    5164
tgaacttttt tgcaagcaca cttgtaacca tatgtgtata attaacaaac ctgtgtatgc    5224
ttatgcctgg gcaactattt tttgtaactc ttgtgtagat tgtctctaaa caatgtgtga    5284
tctttatttt gaaaaataca gaactttgga atctg                               5319
```

<210> SEQ ID NO 8
<211> LENGTH: 1186
<212> TYPE: PRT
<213> ORGANISM: Homo sapiens

<400> SEQUENCE: 8

```
Met Ser Val Ala Cys Val Leu Lys Arg Lys Ala Val Leu Trp Gln Asp
  1               5                  10                  15

Ser Phe Ser Pro His Leu Lys His Pro Gln Glu Pro Ala Asn Pro
             20                  25                  30

Asn Met Pro Val Val Leu Thr Ser Gly Thr Gly Ser Gln Ala Gln Pro
         35                  40                  45

Gln Pro Ala Ala Asn Gln Ala Leu Ala Ala Gly Thr His Ser Ser Pro
     50                  55                  60

Val Pro Gly Ser Ile Gly Val Ala Gly Arg Ser Gln Asp Asp Ala Met
 65                  70                  75                  80

Val Asp Tyr Phe Phe Gln Arg Gln His Gly Glu Gln Leu Gly Gly Gly
                 85                  90                  95

Gly Ser Gly Gly Gly Gly Tyr Asn Asn Ser Lys His Arg Trp Pro Thr
            100                 105                 110

Gly Asp Asn Ile His Ala Glu His Gln Val Arg Ser Met Asp Glu Leu
        115                 120                 125

Asn His Asp Phe Gln Ala Leu Ala Leu Glu Gly Arg Ala Met Gly Glu
    130                 135                 140

Gln Leu Leu Pro Gly Lys Lys Phe Trp Glu Thr Asp Glu Ser Ser Lys
145                 150                 155                 160

Asp Gly Pro Lys Gly Ile Phe Leu Gly Asp Gln Trp Arg Asp Ser Ala
                165                 170                 175

Trp Gly Thr Ser Asp His Ser Val Ser Gln Pro Ile Met Val Gln Arg
            180                 185                 190

Arg Pro Gly Gln Ser Phe His Val Asn Ser Glu Val Asn Ser Val Leu
```

-continued

```
            195                 200                 205
Ser Pro Arg Ser Glu Ser Gly Gly Leu Gly Val Ser Met Val Glu Tyr
    210                 215                 220

Val Leu Ser Ser Ser Pro Gly Asp Ser Cys Leu Arg Lys Gly Gly Phe
225                 230                 235                 240

Gly Pro Arg Asp Ala Asp Ser Asp Glu Asn Asp Lys Gly Glu Lys Lys
                245                 250                 255

Asn Lys Gly Thr Phe Asp Gly Asp Lys Leu Gly Asp Leu Lys Glu Glu
                260                 265                 270

Gly Asp Val Met Asp Lys Thr Asn Gly Leu Pro Val Gln Asn Gly Ile
            275                 280                 285

Asp Ala Asp Val Lys Asp Phe Ser Arg Thr Pro Gly Asn Cys Gln Asn
        290                 295                 300

Ser Ala Asn Glu Val Asp Leu Leu Gly Pro Asn Gln Asn Gly Ser Glu
305                 310                 315                 320

Gly Leu Ala Gln Leu Thr Ser Thr Asn Gly Ala Lys Pro Val Glu Asp
                325                 330                 335

Phe Ser Asn Met Glu Ser Gln Ser Val Pro Leu Asp Pro Met Glu His
                340                 345                 350

Val Gly Met Glu Pro Leu Gln Phe Asp Tyr Ser Gly Thr Gln Val Pro
            355                 360                 365

Val Asp Ser Ala Ala Ala Thr Val Gly Leu Phe Asp Tyr Asn Ser Gln
        370                 375                 380

Gln Gln Leu Phe Gln Arg Pro Asn Ala Leu Ala Val Gln Gln Leu Thr
385                 390                 395                 400

Ala Ala Gln Gln Gln Gln Tyr Ala Leu Ala Ala Ala His Gln Pro His
                405                 410                 415

Ile Gly Leu Ala Pro Ala Ala Phe Val Pro Asn Pro Tyr Ile Ile Ser
                420                 425                 430

Ala Ala Pro Pro Gly Thr Asp Pro Tyr Thr Ala Gly Leu Ala Ala Ala
            435                 440                 445

Ala Thr Leu Gly Pro Ala Val Val Pro His Gln Tyr Tyr Gly Val Thr
        450                 455                 460

Pro Trp Gly Val Tyr Pro Ala Ser Leu Phe Gln Gln Gln Ala Ala Ala
465                 470                 475                 480

Ala Ala Ala Ala Thr Asn Ser Ala Asn Gln Gln Thr Thr Pro Gln Ala
                485                 490                 495

Gln Gln Gly Gln Gln Gln Val Leu Arg Gly Gly Ala Ser Gln Arg Pro
            500                 505                 510

Leu Thr Pro Asn Gln Asn Gln Gln Gly Gln Gln Thr Asp Pro Leu Val
        515                 520                 525

Ala Ala Ala Ala Val Asn Ser Ala Leu Ala Phe Gly Gln Gly Leu Ala
    530                 535                 540

Ala Gly Met Pro Gly Tyr Pro Val Leu Ala Pro Ala Ala Tyr Tyr Asp
545                 550                 555                 560

Gln Thr Gly Ala Leu Val Val Asn Ala Gly Ala Arg Asn Gly Leu Gly
                565                 570                 575

Ala Pro Val Arg Leu Val Ala Pro Ala Pro Val Ile Ile Ser Ser Ser
            580                 585                 590

Ala Ala Gln Ala Ala Val Ala Ala Ala Ala Ser Ala Asn Gly Ala
        595                 600                 605

Ala Gly Gly Leu Ala Gly Thr Thr Asn Gly Pro Phe Arg Pro Leu Gly
    610                 615                 620
```

```
Thr Gln Gln Pro Gln Pro Gln Pro Gln Gln Pro Asn Asn Asn Leu
625                 630                 635                 640

Ala Ser Ser Ser Phe Tyr Gly Asn Asn Ser Leu Asn Ser Asn Ser Gln
            645                 650                 655

Ser Ser Ser Leu Phe Ser Gln Gly Ser Ala Gln Pro Ala Asn Thr Ser
            660                 665                 670

Leu Gly Phe Gly Ser Ser Ser Leu Gly Ala Thr Leu Gly Ser Ala
        675                 680                 685

Leu Gly Gly Phe Gly Thr Ala Val Ala Asn Ser Asn Thr Gly Ser Gly
        690                 695                 700

Ser Arg Arg Asp Ser Leu Thr Gly Ser Ser Asp Leu Tyr Lys Arg Thr
705                 710                 715                 720

Ser Ser Ser Leu Thr Pro Ile Gly His Ser Phe Tyr Asn Gly Leu Ser
            725                 730                 735

Phe Ser Ser Ser Pro Gly Pro Val Gly Met Pro Leu Pro Ser Gln Gly
            740                 745                 750

Pro Gly His Ser Gln Thr Pro Pro Ser Leu Ser Ser His Gly Ser
        755                 760                 765

Ser Ser Ser Leu Asn Leu Gly Gly Leu Thr Asn Gly Ser Gly Arg Tyr
770                 775                 780

Ile Ser Ala Ala Pro Gly Ala Glu Ala Lys Tyr Arg Ser Ala Ser Ser
785                 790                 795                 800

Ala Ser Ser Leu Phe Ser Pro Ser Ser Thr Leu Phe Ser Ser Ser Arg
            805                 810                 815

Leu Arg Tyr Gly Met Ser Asp Val Met Pro Ser Gly Arg Ser Arg Leu
        820                 825                 830

Leu Glu Asp Phe Arg Asn Asn Arg Tyr Pro Asn Leu Gln Leu Arg Glu
        835                 840                 845

Ile Ala Gly His Ile Met Glu Phe Ser Gln Asp Gln His Gly Ser Arg
850                 855                 860

Phe Ile Gln Leu Lys Leu Glu Arg Ala Thr Pro Ala Glu Arg Gln Leu
865                 870                 875                 880

Val Phe Asn Glu Ile Leu Gln Ala Ala Tyr Gln Leu Met Val Asp Val
            885                 890                 895

Phe Gly Asn Tyr Val Ile Gln Lys Phe Glu Phe Gly Ser Leu Glu
        900                 905                 910

Gln Lys Leu Ala Leu Ala Glu Arg Ile Arg Gly His Val Leu Ser Leu
        915                 920                 925

Ala Leu Gln Met Tyr Gly Cys Arg Val Ile Gln Lys Ala Leu Glu Phe
930                 935                 940

Ile Pro Ser Asp Gln Gln Asn Glu Met Val Arg Glu Leu Asp Gly His
945                 950                 955                 960

Val Leu Lys Cys Val Lys Asp Gln Asn Gly Asn His Val Val Gln Lys
            965                 970                 975

Cys Ile Glu Cys Val Gln Pro Gln Ser Leu Gln Phe Ile Ile Asp Ala
            980                 985                 990

Phe Lys Gly Gln Val Phe Ala Leu Ser Thr His Pro Tyr Gly Cys Arg
        995                 1000                1005

Val Ile Gln Arg Ile Leu Glu His Cys Leu Pro Asp Gln Thr Leu Pro
        1010                1015                1020

Ile Leu Glu Glu Leu His Gln His Thr Glu Gln Leu Val Gln Asp Gln
1025                1030                1035                1040
```

```
Tyr Gly Asn Tyr Val Ile Gln His Val Leu Glu His Gly Arg Pro Glu
            1045                1050                1055

Asp Lys Ser Lys Ile Val Ala Glu Ile Arg Gly Asn Val Leu Val Leu
            1060                1065                1070

Ser Gln His Lys Phe Ala Ser Asn Val Val Glu Lys Cys Val Thr His
            1075                1080                1085

Ala Ser Arg Thr Glu Arg Ala Val Leu Ile Asp Glu Val Cys Thr Met
            1090                1095                1100

Asn Asp Gly Pro His Ser Ala Leu Tyr Thr Met Met Lys Asp Gln Tyr
1105                1110                1115                1120

Ala Asn Tyr Val Val Gln Lys Met Ile Asp Val Ala Glu Pro Gly Gln
            1125                1130                1135

Arg Lys Ile Val Met His Lys Ile Arg Pro His Ile Ala Thr Leu Arg
            1140                1145                1150

Lys Tyr Thr Tyr Gly Lys His Ile Leu Ala Lys Leu Glu Lys Tyr Tyr
            1155                1160                1165

Met Lys Asn Gly Val Asp Leu Gly Pro Ile Cys Gly Pro Pro Asn Gly
            1170                1175                1180

Ile Ile
1185

<210> SEQ ID NO 9
<211> LENGTH: 2112
<212> TYPE: DNA
<213> ORGANISM: Homo sapiens
<220> FEATURE:
<221> NAME/KEY: CDS
<222> LOCATION: (419)...(1942)
<223> OTHER INFORMATION: D13645

<400> SEQUENCE: 9
ggaagttaaa gggaaaaagc aattcacagg aaagagtaca aagacagcac aagaaaaaaa      60
cagatttcat aaaaatagtg attctggttc ttcaaagaca tttccaacaa ggaaagttgc     120
taaagaaggt ggacctaaag tcacatctag aactttgag aaaagtatca caaaacttgg     180 gaaaagggt gtaaagcagt tcaagaataa gcagcaaggg gacaaatcac caaagaacaa     240
attccagccg gcaaataaat tcaacaagaa gagaaaattc cagccagatg gtagaagcga     300
tgaatcagca gccaagaagc ccaaatggga tgacttcaaa agaagaagaa aagaactgaa     360
gcaaagcaga caactcagtg ataaaaccaa ctatgacatt gttgttcggg caaagcag     418 atg tgg gag att tta aga aga aaa gac tgt gac aaa gaa aaa aga gta     466 aag tta atg agt gat ttg cag aag ttg att caa ggg aaa att aaa act     514
Met Trp Glu Ile Leu Arg Arg Lys Asp Cys Asp Lys Glu Lys Arg Val
1               5                   10                  15 att gca ttt gca cac gat tca act cgt gtg atc cag tgt tac att cag     562
Lys Leu Met Ser Asp Leu Gln Lys Leu Ile Gln Gly Lys Ile Lys Thr
            20                  25                  30 tat ggt aat gaa gaa cag aga aaa cag gct ttt gaa gaa ttg cga gat     610
Ile Ala Phe Ala His Asp Ser Thr Arg Val Ile Gln Cys Tyr Ile Gln
        35                  40                  45 gat ttg gtt gag tta agt aaa gcc aaa tat tcg aga aat att gtt aag     658
Tyr Gly Asn Glu Glu Gln Arg Lys Gln Ala Phe Glu Glu Leu Arg Asp
    50                  55                  60 aaa ttt ctc atg tat gga agt aaa cca cag att gca gag ata atc aga     706
Asp Leu Val Glu Leu Ser Lys Ala Lys Tyr Ser Arg Asn Ile Val Lys
65                  70                  75                  80 agt ttt aaa ggc cac gtg agg aag atg ctg cgg cat gcg gaa gca tca     754
```

```
                 Lys Phe Leu Met Tyr Gly Ser Lys Pro Gln Ile Ala Glu Ile Ile Arg
                                     85                  90                  95 gcc atc gtg gag tac gca tac aat gac aaa gcc att ttg gag cag agg            802
Ser Phe Lys Gly His Val Arg Lys Met Leu Arg His Ala Glu Ala Ser
            100                 105                 110 aac atg ctg acg gaa gag ctc tat ggg aac aca ttt cag ctt tac aag            850
Ala Ile Val Glu Tyr Ala Tyr Asn Asp Lys Ala Ile Leu Glu Gln Arg
            115                 120                 125 tca gca gat cac cga act ctg gac aaa gtg tta gag gta cag cca gaa            898
Asn Met Leu Thr Glu Glu Leu Tyr Gly Asn Thr Phe Gln Leu Tyr Lys
130                 135                 140 aaa tta gaa ctt att atg gat gaa atg aaa cag att cta act cca atg            946
Ser Ala Asp His Arg Thr Leu Asp Lys Val Leu Glu Val Gln Pro Glu
145                 150                 155                 160 gcc caa aag gaa gct gtg att aag cac tca ttg gtg cat aaa gta ttc            994
Lys Leu Glu Leu Ile Met Asp Glu Met Lys Gln Ile Leu Thr Pro Met
            165                 170                 175 ttg gac ttt ttt acc tat gca ccc ccc aaa ctc aga tca gaa atg att           1042
Ala Gln Lys Glu Ala Val Ile Lys His Ser Leu Val His Lys Val Phe
            180                 185                 190 gaa gcc atc cgc gaa gcg gtg gtc tac ctg gca cac aca cac gat ggc           1090
Leu Asp Phe Phe Thr Tyr Ala Pro Pro Lys Leu Arg Ser Glu Met Ile
            195                 200                 205 gcc aga gtg gcc atg cac tgc ctg tgg cat ggc acg ccc aag gac agg           1138
Glu Ala Ile Arg Glu Ala Val Val Tyr Leu Ala His Thr His Asp Gly
            210                 215                 220 aaa gtg att gtg aaa aca atg aag act tat gtt gaa aag gtg gct aat           1186
Ala Arg Val Ala Met His Cys Leu Trp His Gly Thr Pro Lys Asp Arg
225                 230                 235                 240 ggc caa tac tcc cat ttg gtt tta ctg gcg gca ttt gat tgt att gat           1234
Lys Val Ile Val Lys Thr Met Lys Thr Tyr Val Glu Lys Val Ala Asn
            245                 250                 255 gat act aag ctt gtg aag cag ata atc ata tca gaa att atc agt tca           1282
Gly Gln Tyr Ser His Leu Val Leu Leu Ala Ala Phe Asp Cys Ile Asp
            260                 265                 270 ttg cct agc ata gta aat gac aaa tat gga agg aag gtc cta ttg tac           1330
Asp Thr Lys Leu Val Lys Gln Ile Ile Ile Ser Glu Ile Ile Ser Ser
            275                 280                 285 tta cta agc ccc aga gat cct gca cat aca gta cga gaa atc att gaa           1378
Leu Pro Ser Ile Val Asn Asp Lys Tyr Gly Arg Lys Val Leu Leu Tyr
            290                 295                 300 gtt ctg caa aaa gga gat gga aat gca cac agt aag aaa gat aca gag           1426
Leu Leu Ser Pro Arg Asp Pro Ala His Thr Val Arg Glu Ile Ile Glu
305                 310                 315                 320 gtc cgc aga cgg gag ctc cta gaa tcc att tct cca gct ttg tta agc           1474
Val Leu Gln Lys Gly Asp Gly Asn Ala His Ser Lys Lys Asp Thr Glu
            325                 330                 335 tac ctg caa gaa cac gcc caa gaa gtg gtg cta gat aag tct gcg tgt           1522
Val Arg Arg Arg Glu Leu Leu Glu Ser Ile Ser Pro Ala Leu Leu Ser
            340                 345                 350 gtg ttg gtg tct gac att ctg gga tct gcc act gga gac gtt cag cct           1570
Tyr Leu Gln Glu His Ala Gln Glu Val Val Leu Asp Lys Ser Ala Cys
            355                 360                 365 acc atg aat gcc atc gcc agc ttg gca gca aca gga ctg cat cct ggt           1618
Val Leu Val Ser Asp Ile Leu Gly Ser Ala Thr Gly Asp Val Gln Pro
            370                 375                 380 ggc aag gac gga gag ctt cac att gca gaa cat cct gca gga cat cta           1666
Thr Met Asn Ala Ile Ala Ser Leu Ala Ala Thr Gly Leu His Pro Gly
385                 390                 395                 400
```

-continued

```
gtt ctg aag tgg tta ata gag caa gat aaa aag atg aaa gaa aat ggg      1714
Gly Lys Asp Gly Glu Leu His Ile Ala Glu His Pro Ala Gly His Leu
            405                 410                 415 aga gaa ggt tgt ttt gca aaa aca ctt gta gag cat gtt ggt atg aag      1762
Val Leu Lys Trp Leu Ile Glu Gln Asp Lys Lys Met Lys Glu Asn Gly
        420                 425                 430 aac ctg aag tcc tgg gct agt gta aat cga ggt gcc att att ctt tct      1810
Arg Glu Gly Cys Phe Ala Lys Thr Leu Val Glu His Val Gly Met Lys
    435                 440                 445 agc ctc ctc cag agt tgt gac ctg gaa gtt gca aac aaa gtc aaa gct      1858
Asn Leu Lys Ser Trp Ala Ser Val Asn Arg Gly Ala Ile Ile Leu Ser
450                 455                 460 gca ctg aaa agc ttg att cct aca ctg gaa aaa acc aaa agc acc agc      1906
Ser Leu Leu Gln Ser Cys Asp Leu Glu Val Ala Asn Lys Val Lys Ala
465                 470                 475                 480 aaa gga ata gaa att cta ctt gaa aaa ctg agc aca taggtggaaa           1952
Ala Leu Lys Ser Leu Ile Pro Thr Leu Glu Lys Thr Lys Ser Thr Ser
            485                 490                 495 gagttaagag caagatggaa tgattttttc tgttctctgt tctgtttccc aatgcagaaa    2012
Lys Gly Ile Glu Ile Leu Leu Glu Lys Leu Ser Thr
            500                 505 agaagggta gggtccacca tactggtaat tggggtactc tgtatatgtg tttcttcttt     2072
gtatacgaat ctatttatat aaattgtttt tttaaatggt                          2112

<210> SEQ ID NO 10
<211> LENGTH: 508
<212> TYPE: PRT
<213> ORGANISM: Homo sapiens

<400> SEQUENCE: 10

Met Trp Glu Ile Leu Arg Arg Lys Asp Cys Asp Lys Glu Lys Arg Val
  1               5                  10                  15

Lys Leu Met Ser Asp Leu Gln Lys Leu Ile Gln Gly Lys Ile Lys Thr
             20                  25                  30

Ile Ala Phe Ala His Asp Ser Thr Arg Val Ile Gln Cys Tyr Ile Gln
         35                  40                  45

Tyr Gly Asn Glu Glu Gln Arg Lys Gln Ala Phe Glu Glu Leu Arg Asp
     50                  55                  60

Asp Leu Val Glu Leu Ser Lys Ala Lys Tyr Ser Arg Asn Ile Val Lys
65                   70                  75                  80

Lys Phe Leu Met Tyr Gly Ser Lys Pro Gln Ile Ala Glu Ile Ile Arg
                 85                  90                  95

Ser Phe Lys Gly His Val Arg Lys Met Leu Arg His Ala Glu Ala Ser
            100                 105                 110

Ala Ile Val Glu Tyr Ala Tyr Asn Asp Lys Ala Ile Leu Glu Gln Arg
        115                 120                 125

Asn Met Leu Thr Glu Glu Leu Tyr Gly Asn Thr Phe Gln Leu Tyr Lys
    130                 135                 140

Ser Ala Asp His Arg Thr Leu Asp Lys Val Leu Glu Val Gln Pro Glu
145                 150                 155                 160

Lys Leu Glu Leu Ile Met Asp Glu Met Lys Gln Ile Leu Thr Pro Met
                165                 170                 175

Ala Gln Lys Glu Ala Val Ile Lys His Ser Leu Val His Lys Val Phe
            180                 185                 190

Leu Asp Phe Phe Thr Tyr Ala Pro Pro Lys Leu Arg Ser Glu Met Ile
        195                 200                 205
```

-continued

| | | | | | | | | | | | |
|---|---|---|---|---|---|---|---|---|---|---|---|
|Glu|Ala|Ile|Arg|Glu|Ala|Val|Val|Tyr|Leu|Ala|His|Thr|His|Asp|Gly|
| |210| | | |215| | | |220| | | | | | |
|Ala|Arg|Val|Ala|Met|His|Cys|Leu|Trp|His|Gly|Thr|Pro|Lys|Asp|Arg|
|225| | | | |230| | | | |235| | | | |240|
|Lys|Val|Ile|Val|Lys|Thr|Met|Lys|Thr|Tyr|Val|Glu|Lys|Val|Ala|Asn|
| | | | |245| | | | |250| | | | |255| |
|Gly|Gln|Tyr|Ser|His|Leu|Val|Leu|Leu|Ala|Ala|Phe|Asp|Cys|Ile|Asp|
| | | |260| | | | |265| | | | |270| | |
|Asp|Thr|Lys|Leu|Val|Lys|Gln|Ile|Ile|Ile|Ser|Glu|Ile|Ile|Ser|Ser|
| | |275| | | | |280| | | | |285| | | |
|Leu|Pro|Ser|Ile|Val|Asn|Asp|Lys|Tyr|Gly|Arg|Lys|Val|Leu|Leu|Tyr|
| |290| | | | |295| | | | |300| | | | |
|Leu|Leu|Ser|Pro|Arg|Asp|Pro|Ala|His|Thr|Val|Arg|Glu|Ile|Ile|Glu|
|305| | | | |310| | | | |315| | | | |320|
|Val|Leu|Gln|Lys|Gly|Asp|Gly|Asn|Ala|His|Ser|Lys|Lys|Asp|Thr|Glu|
| | | | |325| | | | |330| | | | |335| |
|Val|Arg|Arg|Arg|Glu|Leu|Leu|Glu|Ser|Ile|Ser|Pro|Ala|Leu|Leu|Ser|
| | | |340| | | | |345| | | | |350| | |
|Tyr|Leu|Gln|Glu|His|Ala|Gln|Glu|Val|Val|Leu|Asp|Lys|Ser|Ala|Cys|
| | |355| | | | |360| | | | |365| | | |
|Val|Leu|Val|Ser|Asp|Ile|Leu|Gly|Ser|Ala|Thr|Gly|Asp|Val|Gln|Pro|
| |370| | | | |375| | | | |380| | | | |
|Thr|Met|Asn|Ala|Ile|Ala|Ser|Leu|Ala|Ala|Thr|Gly|Leu|His|Pro|Gly|
|385| | | | |390| | | | |395| | | | |400|
|Gly|Lys|Asp|Gly|Glu|Leu|His|Ile|Ala|Glu|His|Pro|Ala|Gly|His|Leu|
| | | | |405| | | | |410| | | | |415| |
|Val|Leu|Lys|Trp|Leu|Ile|Glu|Gln|Asp|Lys|Lys|Met|Lys|Glu|Asn|Gly|
| | | |420| | | | |425| | | | |430| | |
|Arg|Glu|Gly|Cys|Phe|Ala|Lys|Thr|Leu|Val|Glu|His|Val|Gly|Met|Lys|
| | |435| | | | |440| | | | |445| | | |
|Asn|Leu|Lys|Ser|Trp|Ala|Ser|Val|Asn|Arg|Gly|Ala|Ile|Ile|Leu|Ser|
| |450| | | | |455| | | | |460| | | | |
|Ser|Leu|Leu|Gln|Ser|Cys|Asp|Leu|Glu|Val|Ala|Asn|Lys|Val|Lys|Ala|
|465| | | | |470| | | | |475| | | | |480|
|Ala|Leu|Lys|Ser|Leu|Ile|Pro|Thr|Leu|Glu|Lys|Thr|Lys|Ser|Thr|Ser|
| | | | |485| | | | |490| | | | |495| |
|Lys|Gly|Ile|Glu|Ile|Leu|Leu|Glu|Lys|Leu|Ser|Thr| | | | |
| | | | |500| | | | |505| | | | | | |

<210> SEQ ID NO 11
<211> LENGTH: 2457
<212> TYPE: DNA
<213> ORGANISM: Saccharomyces cerevisiae
<220> FEATURE:
<221> NAME/KEY: CDS
<222> LOCATION: (645)...(1655)
<223> OTHER INFORMATION: NCA3

<400> SEQUENCE: 11

| | | | | | |
|---|---|---|---|---|---|
|ggatccctct|gtgaggccga|ttatgcaggc|ctagacccgc|acgtgaccac|ttcgagagca|60|
|agttgcctgc|gagtttctct|gcccgaggaa|aaagaaatgg|aggcaattta|cttaatatgg|120|
|tatgagagga|tcttttgacg|gcaaatagat|gcgccatctc|cgagaaaaaa|tctagacaat|180|
|aacagcgaca|attaacctaa|agaggataga|agatcgagca|aaaaaatttt|ttaatatggg|240|
|gtcagtggcg|atattatact|ataggagtta|aagagtaagt|tgagtgtaag|gtggtagaat|300|

-continued

```
tatgattgaa ctccgaaact aagcgccgat tatgggtggc aaagcggaca gcttttgata      360
tataatcgat cgctctcgta gttgatatcc tctctcttgc ttatcttttc ctgtatatag      420
tatatgtgta catacagata cgaatatacc tcagttagtt tgttttaaca ttaaatattc      480
aacagttgcc agtagcaaaa agaatatatc cattcatttc gagcttttc gtctcattac       540 tgatatccaa ctaacagtct cctcatagac ggtaccttac tttcctttaa tattaaaata     600
ctagtatagt cgcacatact taactcgtct ctctctaaca cata atg aaa att tcc      656
                                                  Met Lys Ile Ser
                                                    1 gca gct tta ata ttg tct tcc ctt tct tct gtc gca ttt tct gcc cct       704
Ala Ala Leu Ile Leu Ser Ser Leu Ser Ser Val Ala Phe Ser Ala Pro
 5                  10                  15                  20 gca cct gct cca gcg gac agt cat cat gaa gat cat cac aaa gat gaa       752
Ala Pro Ala Pro Ala Asp Ser His His Glu Asp His His Lys Asp Glu
                25                  30                  35 aaa cca gcg gtt gtc act gtc act caa tac ata gat tcc aat gcc gct       800
Lys Pro Ala Val Val Thr Val Thr Gln Tyr Ile Asp Ser Asn Ala Ala
        40                  45                  50 act agt act gta gaa tct gct gct act acc act aca ttg tcc tca tct       848
Thr Ser Thr Val Glu Ser Ala Ala Thr Thr Thr Thr Leu Ser Ser Ser
    55                  60                  65 gag aag gat acc tct gaa cag aag cgt gat ggc gga ttc caa gat ggt       896
Glu Lys Asp Thr Ser Glu Gln Lys Arg Asp Gly Gly Phe Gln Asp Gly
 70                  75                  80 act gtc aaa tgt tcg gac ttc cct tct gta aac ggt ata gtt tcc ttg       944
Thr Val Lys Cys Ser Asp Phe Pro Ser Val Asn Gly Ile Val Ser Leu
85                  90                  95                 100 gac tgg cta gga ttt ggt gga tgg gcc tct gtc atg gac atg gat gcc       992
Asp Trp Leu Gly Phe Gly Gly Trp Ala Ser Val Met Asp Met Asp Ala
                105                 110                 115 aac act tcg tcc gaa tgt aag gat ggc tac tac tgt tct tat gca tgt      1040
Asn Thr Ser Ser Glu Cys Lys Asp Gly Tyr Tyr Cys Ser Tyr Ala Cys
                120                 125                 130 gaa cct gga atg tca aag act caa tgg cct tct gac caa cca agc gat      1088
Glu Pro Gly Met Ser Lys Thr Gln Trp Pro Ser Asp Gln Pro Ser Asp
        135                 140                 145 ggt aaa tct gtt ggt ggt ctt tat tgt aaa aat ggt tac ttg tac cgt      1136
Gly Lys Ser Val Gly Gly Leu Tyr Cys Lys Asn Gly Tyr Leu Tyr Arg
150                 155                 160 acc aac act gat acc agc gat tta tgt tct acg gat gaa aca tct gct      1184
Thr Asn Thr Asp Thr Ser Asp Leu Cys Ser Thr Asp Glu Thr Ser Ala
165                 170                 175                 180 aag gcc att aac aaa aag tct gac tcc att gct cta tgt agg acg gat      1232
Lys Ala Ile Asn Lys Lys Ser Asp Ser Ile Ala Leu Cys Arg Thr Asp
                185                 190                 195 tac cca gga tct gaa aac atg gtg att ccc aca gtg gtt gat ggt gga      1280
Tyr Pro Gly Ser Glu Asn Met Val Ile Pro Thr Val Val Asp Gly Gly
        200                 205                 210 gat tca caa cca att tca gtc gtt gat gaa gac act tat tat caa tgg      1328
Asp Ser Gln Pro Ile Ser Val Val Asp Glu Asp Thr Tyr Tyr Gln Trp
        215                 220                 225 cag ggt aaa aag act tct gct cag tac tat att aac aac gcc ggt gta      1376
Gln Gly Lys Lys Thr Ser Ala Gln Tyr Tyr Ile Asn Asn Ala Gly Val
230                 235                 240 tct gca gaa gat ggg tgc att tgg ggt act tct ggt tcg gat gtc ggc      1424
Ser Ala Glu Asp Gly Cys Ile Trp Gly Thr Ser Gly Ser Asp Val Gly
245                 250                 255                 260 aac tgg gct cca cta gtg tta ggt gct ggt tcc act aat gga gaa aca      1472
```

```
Asn Trp Ala Pro Leu Val Leu Gly Ala Gly Ser Thr Asn Gly Glu Thr
                265                 270                 275
tac ttg tcg ttg att cca aac ccc aac agt aac caa gct gcc aac ttt    1520
Tyr Leu Ser Leu Ile Pro Asn Pro Asn Ser Asn Gln Ala Ala Asn Phe
                280                 285                 290
aac gtt aaa ata gtt gca tcc gat ggc gct aac gtt cag ggc agc tgt    1568
Asn Val Lys Ile Val Ala Ser Asp Gly Ala Asn Val Gln Gly Ser Cys
                295                 300                 305
gcg tat gaa gat ggc tct ttc acc gga gat ggt tcc gat ggt tgc aca    1616
Ala Tyr Glu Asp Gly Ser Phe Thr Gly Asp Gly Ser Asp Gly Cys Thr
            310                 315                 320
gtt tct gtt tta tct gga tct gct gaa ttt gtt ttc tat taagtcactc     1665
Val Ser Val Leu Ser Gly Ser Ala Glu Phe Val Phe Tyr
325                 330                 335 ttcttttcgg taaagaatg tcttgtattt tgataccctc aattcccctt attattcttt   1725
ttcttccgct ctctatttat tattatacat tgggattccg ttatatttt ctcctttcag   1785 ttcattttac ttcttaaaaa gtttcgttga tcgctattat gctatggatt caaagatttt  1845
cttttctctc tcttcaaggt gtactctgca ttacggtttt ctttagttcg tttattttt   1905 ttttgttaac aaggtgtttg tatacatata tataaatata tggaaatatt atagtgttta  1965
ttttgttact tcctgcgagt tgcaacagaa ctaacaagat gccatgctgt ttttttcat   2025 tttttggcta taaaaataac agtatcctag tccttgtgtt cggctttaaa atggaattgc  2085 aaacccata attccttctt cacaccgaac aaaccgccta gtagtcgatt ttcagagact   2145
ctaatgcttt gaatataatt ttttcttca aaaatttcct taagcgtgct atcgaatgag   2205
tagacatcaa tcaagagttt catggtctcc ccgtatttgc cgctgcttct aatatttttg  2265
gagtgtagca tagcccaatc aatcaaatct tcgataatgc cacttttac atatacacga   2325 cgacaaccca cagtagtaac actcatgact aaattttcat cagtacttaa tgtcatgtta  2385
ggggctaacg aaatcaatgc aatgggcgtt tctctataaa cgatgatatg cgtattgttc  2445
accactggat cc                                                      2457

<210> SEQ ID NO 12
<211> LENGTH: 337
<212> TYPE: PRT
<213> ORGANISM: Saccharomyces cerevisiae

<400> SEQUENCE: 12

Met Lys Ile Ser Ala Ala Leu Ile Leu Ser Ser Leu Ser Ser Val Ala
1               5                   10                  15

Phe Ser Ala Pro Ala Pro Ala Pro Ala Asp Ser His His Glu Asp His
                20                  25                  30

His Lys Asp Glu Lys Pro Ala Val Val Thr Val Thr Gln Tyr Ile Asp
            35                  40                  45

Ser Asn Ala Ala Thr Ser Thr Val Glu Ser Ala Ala Thr Thr Thr Thr
        50                  55                  60

Leu Ser Ser Ser Glu Lys Asp Thr Ser Glu Gln Lys Arg Asp Gly Gly
65                  70                  75                  80

Phe Gln Asp Gly Thr Val Lys Cys Ser Asp Phe Pro Ser Val Asn Gly
                85                  90                  95

Ile Val Ser Leu Asp Trp Leu Gly Phe Gly Gly Trp Ala Ser Val Met
                100                 105                 110

Asp Met Asp Ala Asn Thr Ser Ser Glu Cys Lys Asp Gly Tyr Tyr Cys
            115                 120                 125
```

```
Ser Tyr Ala Cys Glu Pro Gly Met Ser Lys Thr Gln Trp Pro Ser Asp
        130                 135                 140

Gln Pro Ser Asp Gly Lys Ser Val Gly Gly Leu Tyr Cys Lys Asn Gly
145                 150                 155                 160

Tyr Leu Tyr Arg Thr Asn Thr Asp Thr Ser Asp Leu Cys Ser Thr Asp
                165                 170                 175

Glu Thr Ser Ala Lys Ala Ile Asn Lys Lys Ser Asp Ser Ile Ala Leu
            180                 185                 190

Cys Arg Thr Asp Tyr Pro Gly Ser Glu Asn Met Val Ile Pro Thr Val
        195                 200                 205

Val Asp Gly Gly Asp Ser Gln Pro Ile Ser Val Val Asp Glu Asp Thr
    210                 215                 220

Tyr Tyr Gln Trp Gln Gly Lys Lys Thr Ser Ala Gln Tyr Tyr Ile Asn
225                 230                 235                 240

Asn Ala Gly Val Ser Ala Glu Asp Gly Cys Ile Trp Gly Thr Ser Gly
                245                 250                 255

Ser Asp Val Gly Asn Trp Ala Pro Leu Val Leu Gly Ala Gly Ser Thr
            260                 265                 270

Asn Gly Glu Thr Tyr Leu Ser Leu Ile Pro Asn Pro Asn Ser Asn Gln
        275                 280                 285

Ala Ala Asn Phe Asn Val Lys Ile Val Ala Ser Asp Gly Ala Asn Val
    290                 295                 300

Gln Gly Ser Cys Ala Tyr Glu Asp Gly Ser Phe Thr Gly Asp Gly Ser
305                 310                 315                 320

Asp Gly Cys Thr Val Ser Val Leu Ser Gly Ser Ala Glu Phe Val Phe
                325                 330                 335

Tyr
```

```
<210> SEQ ID NO 13
<211> LENGTH: 2150
<212> TYPE: DNA
<213> ORGANISM: Saccharomyces cerevisiae
<220> FEATURE:
<221> NAME/KEY: CDS
<222> LOCATION: (563)...(1987)
<223> OTHER INFORMATION: SAG1

<400> SEQUENCE: 13
tgtttagtgc tacccaacta cttacattcc tttaaaaacc acaatattta agttaacctg     60
agctttattt ttagtaagtt atttaccaca atttttctca tacacctttta caatccgtat   120 tgccatgaat accaaggctt gctcagcttc tgcagcagtt caacccttc caataccgcc    180 aatgcgtcct caaaacgtta gtttagtcgt gctcaaccgc tattttttggt tttatcttcg   240 tttctttctc ctgaacgaca ttcgtcacga aaattgcggc ggaaaatttc ctgatgcgga    300 cacttttttcc cgatccggac atgcctttt ttggcgtttc gcgtcagtca atagaagttt    360
cagatctaca ttaggaagaa ccagaaaata gccattaatg ctttcagcat agcacagcat    420
agcagctgtg tatatcttaa ataagatgta gactggtttg catttggaaa ggttttgtgt    480
aagaaaagca atacttgagg taaaacaaga gaaaaaaaaa cactttacta actaatatcc    540
aatcctttat ttttttgcag aa atg aaa ttc tca act gcc gtt act acg ttg     592
                        Met Lys Phe Ser Thr Ala Val Thr Thr Leu
                         1               5                  10 att agt tct ggt gcc atc gtg tct gct tta cca cac gtg gat gtt cac     640
Ile Ser Ser Gly Ala Ile Val Ser Ala Leu Pro His Val Asp Val His
            15                  20                  25
```

-continued

| | | |
|---|---|---|
| caa gaa gat gcc cac caa cat aag agg gcc gtt gcg tac aaa tac gtt<br>Gln Glu Asp Ala His Gln His Lys Arg Ala Val Ala Tyr Lys Tyr Val<br>            30                35                  40 | 688 |
| tac gaa act gtt gtt gtc gat tct gat ggc cac act gta act cct gct<br>Tyr Glu Thr Val Val Val Asp Ser Asp Gly His Thr Val Thr Pro Ala<br>     45                     50                  55 | 736 |
| gct tca gaa gtc gct act gct gct acc tct gct atc att aca aca tct<br>Ala Ser Glu Val Ala Thr Ala Ala Thr Ser Ala Ile Ile Thr Thr Ser<br>60                     65                  70 | 784 |
| gtg ttg gct cca acc tcc tcc gca gcc gct ggg ata gcc gct tcc att<br>Val Leu Ala Pro Thr Ser Ser Ala Ala Ala Gly Ile Ala Ala Ser Ile<br>75                     80                  85                  90 | 832 |
| gct gtt tca tct gct gcc tta gcc aag aat gag aaa atc tct gat gcc<br>Ala Val Ser Ser Ala Ala Leu Ala Lys Asn Glu Lys Ile Ser Asp Ala<br>                   95                 100                105 | 880 |
| gct gca tct gcc act gcc tca aca tct caa ggg gca tcc tcc tcc tcc<br>Ala Ala Ser Ala Thr Ala Ser Thr Ser Gln Gly Ala Ser Ser Ser Ser<br>                110               115                120 | 928 |
| tcc tcc tcc tcg gca act tct acc cta gaa agc agc tct gtt tct tca<br>Ser Ser Ser Ser Ala Thr Ser Thr Leu Glu Ser Ser Ser Val Ser Ser<br>125                    130                135 | 976 |
| tct agt gaa gaa gct gct cca aca tct act gtc gtg tca act tct tcc<br>Ser Ser Glu Glu Ala Ala Pro Thr Ser Thr Val Val Ser Thr Ser Ser<br>140                   145                150 | 1024 |
| gca acc caa tct agt gct tct tct gcc act aaa tct agt act tct tcc<br>Ala Thr Gln Ser Ser Ala Ser Ser Ala Thr Lys Ser Ser Thr Ser Ser<br>155                  160               165               170 | 1072 |
| act tca cca tct act tct act tct act tcc act tct tct act tcc tct<br>Thr Ser Pro Ser Thr Ser Thr Ser Thr Ser Thr Ser Thr Ser Ser Ser<br>                   175                180               185 | 1120 |
| tcc tct tcc tcc tcc tcc tcc tct tct tct tct tct tct ggc agt ggt<br>Ser Ser Ser Ser Ser Ser Ser Ser Ser Ser Ser Ser Ser Gly Ser Gly<br>                190               195                200 | 1168 |
| agt atc tac ggt gat ttg gcc gac ttt tca ggc cca agt gag aaa ttc<br>Ser Ile Tyr Gly Asp Leu Ala Asp Phe Ser Gly Pro Ser Glu Lys Phe<br>               205                210               215 | 1216 |
| caa gac ggc act att cca tgt gac aaa ttc cca tct ggt caa ggt gtc<br>Gln Asp Gly Thr Ile Pro Cys Asp Lys Phe Pro Ser Gly Gln Gly Val<br>220                  225               230 | 1264 |
| att tct att gac tgg att ggc gag ggt gga tgg tcc ggt gtg gaa aac<br>Ile Ser Ile Asp Trp Ile Gly Glu Gly Gly Trp Ser Gly Val Glu Asn<br>235                  240               245              250 | 1312 |
| acc gac act tcc act ggc ggt tca tgc aag gag ggg tcc tac tgt tcc<br>Thr Asp Thr Ser Thr Gly Gly Ser Cys Lys Glu Gly Ser Tyr Cys Ser<br>                255               260               265 | 1360 |
| tac tcc tgc caa cca ggt atg tct aag acc caa tgg cca tcc gat caa<br>Tyr Ser Cys Gln Pro Gly Met Ser Lys Thr Gln Trp Pro Ser Asp Gln<br>                270               275               280 | 1408 |
| cca tct gac ggt aga tct gtc ggg ggt ttg ttg tgt aaa aat ggt tat<br>Pro Ser Asp Gly Arg Ser Val Gly Gly Leu Leu Cys Lys Asn Gly Tyr<br>          285                290               295 | 1456 |
| ttg tac cgt tct aac act gac gcg gat tac tta tgt gaa tgg ggt gtc<br>Leu Tyr Arg Ser Asn Thr Asp Ala Asp Tyr Leu Cys Glu Trp Gly Val<br>300                  305               310 | 1504 |
| gag gct gcc tat gtt gtt tct aaa cta agc aag ggt gtc gcc att tgc<br>Glu Ala Ala Tyr Val Val Ser Lys Leu Ser Lys Gly Val Ala Ile Cys<br>315                  320               325              330 | 1552 |
| aga acc gac tac ccg ggc act gaa aac atg gtt atc cca acc tat gtt<br>Arg Thr Asp Tyr Pro Gly Thr Glu Asn Met Val Ile Pro Thr Tyr Val<br>                335               340               345 | 1600 |

```
gaa ggg ggt agc tct ttg cca ttg acc gtt gtt gac caa gat act tac    1648
Glu Gly Gly Ser Ser Leu Pro Leu Thr Val Val Asp Gln Asp Thr Tyr
            350                 355                 360 ttt act tgg gaa ggc aaa aag aca tct gct caa tac tac gtt aat aac    1696
Phe Thr Trp Glu Gly Lys Lys Thr Ser Ala Gln Tyr Tyr Val Asn Asn
365                 370                 375 gcc ggc gtc tca gtt gaa gat ggg tgt atc tgg ggt act tct gga tct    1744
Ala Gly Val Ser Val Glu Asp Gly Cys Ile Trp Gly Thr Ser Gly Ser
        380                 385                 390 ggt att ggt aac tgg gca cca tta aac ttt ggt gct ggc tcc act ggt    1792
Gly Ile Gly Asn Trp Ala Pro Leu Asn Phe Gly Ala Gly Ser Thr Gly
395                 400                 405                 410 gga gtc aca tac tta tca ttg att cct aac cca aac aac agc gac gca    1840
Gly Val Thr Tyr Leu Ser Leu Ile Pro Asn Pro Asn Asn Ser Asp Ala
            415                 420                 425 ttg aac tac aac gtc aag ata gtt gct gct gat gat tca tcc aat gtc    1888
Leu Asn Tyr Asn Val Lys Ile Val Ala Ala Asp Asp Ser Ser Asn Val
        430                 435                 440 atc ggt gaa tgt gtt tac gaa aat ggt gag ttc tct ggc ggt gct gac    1936
Ile Gly Glu Cys Val Tyr Glu Asn Gly Glu Phe Ser Gly Gly Ala Asp
                445                 450                 455 ggg tgt acc gtc tct gtt act tcc ggt aaa gct cat ttc gtc tta tac    1984
Gly Cys Thr Val Ser Val Thr Ser Gly Lys Ala His Phe Val Leu Tyr
460                 465                 470 aat taagctacgt gactactact tttccttttt tttttctttt ttcgaacaca         2037
Asn
475 tctcaccccc tatacctcac acaatcacta tggtcccctt ttcttttttac cgatatttat  2097 actgtccacc ttttcttttt cgttaatggc ctcaatgttt ctgtaccatt atc         2150

<210> SEQ ID NO 14
<211> LENGTH: 475
<212> TYPE: PRT
<213> ORGANISM: Saccharomyces cerevisiae

<400> SEQUENCE: 14

Met Lys Phe Ser Thr Ala Val Thr Thr Leu Ile Ser Ser Gly Ala Ile
1               5                   10                  15

Val Ser Ala Leu Pro His Val Asp Val His Gln Glu Asp Ala His Gln
            20                  25                  30

His Lys Arg Ala Val Ala Tyr Lys Tyr Val Tyr Glu Thr Val Val Val
        35                  40                  45

Asp Ser Asp Gly His Thr Val Thr Pro Ala Ala Ser Glu Val Ala Thr
    50                  55                  60

Ala Ala Thr Ser Ala Ile Ile Thr Thr Ser Val Leu Ala Pro Thr Ser
65                  70                  75                  80

Ser Ala Ala Ala Gly Ile Ala Ala Ser Ile Ala Val Ser Ser Ala Ala
                85                  90                  95

Leu Ala Lys Asn Glu Lys Ile Ser Asp Ala Ala Ser Ala Thr Ala
            100                 105                 110

Ser Thr Ser Gln Gly Ala Ser Ser Ser Ser Ser Ser Ala Thr
        115                 120                 125

Ser Thr Leu Glu Ser Ser Val Ser Ser Ser Glu Glu Ala Ala
    130                 135                 140

Pro Thr Ser Thr Val Val Ser Thr Ser Ala Thr Gln Ser Ser Ala
145                 150                 155                 160
```

-continued

```
Ser Ser Ala Thr Lys Ser Ser Thr Ser Ser Thr Ser Pro Ser Thr Ser
            165                 170                 175

Thr Ser Thr Ser Thr Ser Ser Thr Ser Ser Ser Ser Ser Ser Ser Ser
            180                 185                 190

Ser Ser Ser Ser Ser Ser Gly Ser Gly Ser Ile Tyr Gly Asp Leu
        195                 200                 205

Ala Asp Phe Ser Gly Pro Ser Glu Lys Phe Gln Asp Gly Thr Ile Pro
210                 215                 220

Cys Asp Lys Phe Pro Ser Gly Gln Gly Val Ile Ser Ile Asp Trp Ile
225                 230                 235                 240

Gly Glu Gly Gly Trp Ser Gly Val Glu Asn Thr Asp Thr Ser Thr Gly
                    245                 250                 255

Gly Ser Cys Lys Glu Gly Ser Tyr Cys Ser Tyr Ser Cys Gln Pro Gly
            260                 265                 270

Met Ser Lys Thr Gln Trp Pro Ser Asp Gln Pro Ser Asp Gly Arg Ser
            275                 280                 285

Val Gly Gly Leu Leu Cys Lys Asn Gly Tyr Leu Tyr Arg Ser Asn Thr
        290                 295                 300

Asp Ala Asp Tyr Leu Cys Glu Trp Gly Val Glu Ala Ala Tyr Val Val
305                 310                 315                 320

Ser Lys Leu Ser Lys Gly Val Ala Ile Cys Arg Thr Asp Tyr Pro Gly
                    325                 330                 335

Thr Glu Asn Met Val Ile Pro Thr Tyr Val Glu Gly Gly Ser Ser Leu
            340                 345                 350

Pro Leu Thr Val Val Asp Gln Asp Thr Tyr Phe Thr Trp Glu Gly Lys
            355                 360                 365

Lys Thr Ser Ala Gln Tyr Tyr Val Asn Asn Ala Gly Val Ser Val Glu
        370                 375                 380

Asp Gly Cys Ile Trp Gly Thr Gly Ser Gly Ile Gly Asn Trp Ala
385                 390                 395                 400

Pro Leu Asn Phe Gly Ala Gly Ser Thr Gly Gly Val Thr Tyr Leu Ser
                    405                 410                 415

Leu Ile Pro Asn Pro Asn Asn Ser Asp Ala Leu Asn Tyr Asn Val Lys
            420                 425                 430

Ile Val Ala Ala Asp Asp Ser Ser Asn Val Ile Gly Glu Cys Val Tyr
        435                 440                 445

Glu Asn Gly Glu Phe Ser Gly Gly Ala Asp Gly Cys Thr Val Ser Val
    450                 455                 460

Thr Ser Gly Lys Ala His Phe Val Leu Tyr Asn
465                 470                 475
```

<210> SEQ ID NO 15
<211> LENGTH: 145
<212> TYPE: PRT
<213> ORGANISM: Saccharomyces cerevisiae
<220> FEATURE:
<221> NAME/KEY: VARIANT
<222> LOCATION: (1)...(145)
<223> OTHER INFORMATION: Xaa = Any Amino Acid

<400> SEQUENCE: 15

```
Thr Asp Tyr Pro Gly Xaa Glu Asn Met Val Xaa Pro Thr Xaa Val Xaa
  1               5                  10                  15

Xaa Gly Xaa Ser Xaa Pro Xaa Xaa Val Xaa Xaa Xaa Asp Xaa Tyr Xaa
             20                  25                  30

Xaa Trp Xaa Gly Lys Lys Thr Ser Ala Gln Tyr Tyr Xaa Asn Asn Xaa
```

-continued

```
                    35                  40                  45
Gly Val Ser Xaa Glu Asp Gly Cys Ile Trp Gly Thr Xaa Gly Ser Xaa
         50                  55                  60

Xaa Gly Asn Trp Ala Pro Xaa Xaa Gly Ala Xaa Xaa Thr Xaa Gly
 65                  70                  75                  80

Xaa Thr Tyr Leu Ser Xaa Ile Pro Asn Pro Asn Xaa Xaa Xaa Ala Xaa
                 85                  90                  95

Asn Xaa Asn Xaa Lys Ile Val Ala Xaa Asp Xaa Xaa Xaa Xaa Val Xaa
            100                 105                 110

Gly Xaa Cys Xaa Tyr Glu Xaa Gly Xaa Xaa Xaa Gly Xaa Gly Xaa Asp
            115                 120                 125

Gly Cys Thr Val Ser Val Xaa Ser Gly Xaa Ala Xaa Phe Val Xaa Tyr
        130                 135                 140

Xaa
145

<210> SEQ ID NO 16
<211> LENGTH: 60
<212> TYPE: PRT
<213> ORGANISM: Saccharomyces cerevisiae

<400> SEQUENCE: 16

Ser Leu Ile Pro Asn Pro Asn Asn Gly Asn Ala Leu Asn Phe Asn Val
  1               5                  10                  15

Lys Ile Val Ala Ala Asp Asp Ser Ser Thr Val Asn Gly Glu Cys Ile
             20                  25                  30

Tyr Glu Asn Gly Ser Phe Ser Ser Gly Gly Ser Asp Gly Cys Thr Val
         35                  40                  45

Ser Val Thr Ala Gly Lys Ala Lys Phe Val Leu Tyr
     50                  55                  60

<210> SEQ ID NO 17
<211> LENGTH: 16
<212> TYPE: PRT
<213> ORGANISM: Saccharomyces cerevisiae

<400> SEQUENCE: 17

Leu Ala Thr Asp Gln Phe Gly Cys Arg Phe Leu Gln Lys Lys Leu Glu
  1               5                  10                  15

<210> SEQ ID NO 18
<211> LENGTH: 16
<212> TYPE: PRT
<213> ORGANISM: Saccharomyces cerevisiae

<400> SEQUENCE: 18

Leu Ile Leu Asp Pro Phe Gly Asn Tyr Leu Val Asp Lys Ile Cys Asp
  1               5                  10                  15

<210> SEQ ID NO 19
<211> LENGTH: 16
<212> TYPE: PRT
<213> ORGANISM: Saccharomyces cerevisiae

<400> SEQUENCE: 19

Ile Ser Ile Asn Gln Tyr Gly Thr Arg Ser Leu Gln Lys Ile Ile Asp
  1               5                  10                  15

<210> SEQ ID NO 20
<211> LENGTH: 15
```

-continued

```
<212> TYPE: PRT
<213> ORGANISM: Saccharomyces cerevisiae

<400> SEQUENCE: 20

Leu Ile Asn Asp Ile Asn Gly His Val Ile Gln Lys Cys Ile Phe
1               5                   10                  15

<210> SEQ ID NO 21
<211> LENGTH: 16
<212> TYPE: PRT
<213> ORGANISM: Saccharomyces cerevisiae

<400> SEQUENCE: 21

Ile Ser Thr His Lys His Gly Cys Cys Val Leu Gln Lys Ile Leu Ser
1               5                   10                  15

<210> SEQ ID NO 22
<211> LENGTH: 16
<212> TYPE: PRT
<213> ORGANISM: Saccharomyces cerevisiae

<400> SEQUENCE: 22

Leu Ile Asn Asp Gln Phe Gly Asn Tyr Ile Ile Gln Phe Ile Leu Asp
1               5                   10                  15

<210> SEQ ID NO 23
<211> LENGTH: 16
<212> TYPE: PRT
<213> ORGANISM: Saccharomyces cerevisiae

<400> SEQUENCE: 23

Leu Ser Cys Leu Lys Phe Ser Ser Asn Val Val Glu Lys Phe Ile Lys
1               5                   10                  15

<210> SEQ ID NO 24
<211> LENGTH: 16
<212> TYPE: PRT
<213> ORGANISM: Saccharomyces cerevisiae

<400> SEQUENCE: 24

Leu Ile Arg Asp Asn Phe Gly Asn Tyr Ala Leu Gln Thr Leu Leu Asp
1               5                   10                  15

<210> SEQ ID NO 25
<211> LENGTH: 16
<212> TYPE: PRT
<213> ORGANISM: Saccharomyces cerevisiae

<400> SEQUENCE: 25

Leu Cys Lys Asp Gln His Gly Cys Arg Phe Leu Gln Lys Gln Leu Asp
1               5                   10                  15

<210> SEQ ID NO 26
<211> LENGTH: 16
<212> TYPE: PRT
<213> ORGANISM: Saccharomyces cerevisiae

<400> SEQUENCE: 26

Leu Met Thr Asp Ser Phe Gly Asn Tyr Leu Ile Gln Lys Leu Leu Glu
1               5                   10                  15

<210> SEQ ID NO 27
<211> LENGTH: 16
<212> TYPE: PRT
<213> ORGANISM: Saccharomyces cerevisiae
```

```
<400> SEQUENCE: 27

Ile Ser Leu Asn Pro His Gly Thr Arg Ala Leu Gln Lys Leu Ile Glu
1               5                   10                  15

<210> SEQ ID NO 28
<211> LENGTH: 16
<212> TYPE: PRT
<213> ORGANISM: Saccharomyces cerevisiae

<400> SEQUENCE: 28

Leu Ser Lys Asp Leu Asn Gly Asn His Val Ile Gln Lys Cys Leu Gln
1               5                   10                  15

<210> SEQ ID NO 29
<211> LENGTH: 16
<212> TYPE: PRT
<213> ORGANISM: Saccharomyces cerevisiae

<400> SEQUENCE: 29

Ile Ala Thr His Arg His Gly Cys Cys Val Leu Gln Arg Cys Leu Asp
1               5                   10                  15

<210> SEQ ID NO 30
<211> LENGTH: 16
<212> TYPE: PRT
<213> ORGANISM: Saccharomyces cerevisiae

<400> SEQUENCE: 30

Leu Thr Leu Asp Pro Phe Gly Asn Tyr Val Val Gln Tyr Ile Ile Thr
1               5                   10                  15

<210> SEQ ID NO 31
<211> LENGTH: 16
<212> TYPE: PRT
<213> ORGANISM: Saccharomyces cerevisiae

<400> SEQUENCE: 31

Leu Ser Ile His Lys Phe Gly Ser Asn Val Ile Glu Lys Ile Ile Lys
1               5                   10                  15

<210> SEQ ID NO 32
<211> LENGTH: 16
<212> TYPE: PRT
<213> ORGANISM: Saccharomyces cerevisiae

<400> SEQUENCE: 32

Leu Leu Asn Asp Ser Tyr Gly Asn Tyr Val Leu Gln Thr Ala Leu Asp
1               5                   10                  15

<210> SEQ ID NO 33
<211> LENGTH: 16
<212> TYPE: PRT
<213> ORGANISM: Drosophila

<400> SEQUENCE: 33

Phe Ser Gln Asp Gln His Gly Ser Arg Phe Ile Gln Gln Lys Leu Glu
1               5                   10                  15

<210> SEQ ID NO 34
<211> LENGTH: 16
<212> TYPE: PRT
<213> ORGANISM: Drosophila

<400> SEQUENCE: 34
```

Leu Met Thr Asp Val Phe Gly Asn Tyr Val Ile Gln Lys Phe Phe Glu
 1               5                  10                  15

<210> SEQ ID NO 35
<211> LENGTH: 16
<212> TYPE: PRT
<213> ORGANISM: Drosophila

<400> SEQUENCE: 35

Leu Ala Leu Gln Met Tyr Gly Leu Arg Val Ile Gln Lys Ala Leu Glu
 1               5                  10                  15

<210> SEQ ID NO 36
<211> LENGTH: 16
<212> TYPE: PRT
<213> ORGANISM: Drosophila

<400> SEQUENCE: 36

Cys Val Lys Asp Gln Asn Gly Asn His Val Val Gln Lys Cys Ile Glu
 1               5                  10                  15

<210> SEQ ID NO 37
<211> LENGTH: 16
<212> TYPE: PRT
<213> ORGANISM: Drosophila

<400> SEQUENCE: 37

Leu Ser Thr His Pro Tyr Gly Cys Arg Val Ile Gln Arg Ile Leu Glu
 1               5                  10                  15

<210> SEQ ID NO 38
<211> LENGTH: 16
<212> TYPE: PRT
<213> ORGANISM: Drosophila

<400> SEQUENCE: 38

Leu Ile Gln Asp Gln Tyr Gly Asn Tyr Val Ile Gln His Val Leu Glu
 1               5                  10                  15

<210> SEQ ID NO 39
<211> LENGTH: 16
<212> TYPE: PRT
<213> ORGANISM: Drosophila

<400> SEQUENCE: 39

Leu Ser Gln His Lys Phe Ala Ser Asn Val Val Glu Lys Cys Val Thr
 1               5                  10                  15

<210> SEQ ID NO 40
<211> LENGTH: 16
<212> TYPE: PRT
<213> ORGANISM: Drosophila

<400> SEQUENCE: 40

Met Met Lys Asp Gln Tyr Ala Asn Tyr Val Val Gln Lys Met Ile Asp
 1               5                  10                  15

<210> SEQ ID NO 41
<211> LENGTH: 16
<212> TYPE: PRT
<213> ORGANISM: Homo sapiens

<400> SEQUENCE: 41

Phe Ser Gln Asp Gln His Gly Ser Arg Phe Ile Gln Leu Lys Leu Glu

```
<210> SEQ ID NO 42
<211> LENGTH: 16
<212> TYPE: PRT
<213> ORGANISM: Homo sapiens

<400> SEQUENCE: 42

Leu Met Arg Asp Val Phe Gly Asn Tyr Val Ile Gln Lys Phe Phe Glu
 1               5                  10                  15

<210> SEQ ID NO 43
<211> LENGTH: 16
<212> TYPE: PRT
<213> ORGANISM: Homo sapiens

<400> SEQUENCE: 43

Leu Ala Leu Gln Met Tyr Gly Leu Arg Val Ile Gln Lys Ala Leu Glu
 1               5                  10                  15

<210> SEQ ID NO 44
<211> LENGTH: 16
<212> TYPE: PRT
<213> ORGANISM: Homo sapiens

<400> SEQUENCE: 44

Cys Val Lys Asp Gln Asn Gly Asn His Val Gln Lys Cys Ile Glu
 1               5                  10                  15

<210> SEQ ID NO 45
<211> LENGTH: 16
<212> TYPE: PRT
<213> ORGANISM: Homo sapiens

<400> SEQUENCE: 45

Leu Ser Thr His Pro Tyr Gly Cys Arg Val Ile Gln Arg Ile Leu Glu
 1               5                  10                  15

<210> SEQ ID NO 46
<211> LENGTH: 16
<212> TYPE: PRT
<213> ORGANISM: Homo sapiens

<400> SEQUENCE: 46

Leu Val Gln Asp Gln Tyr Gly Asn Tyr Val Ile Gln His Val Leu Glu
 1               5                  10                  15

<210> SEQ ID NO 47
<211> LENGTH: 16
<212> TYPE: PRT
<213> ORGANISM: Homo sapiens

<400> SEQUENCE: 47

Val Leu Ser Gln His Phe Ala Ser Asn Val Val Glu Lys Cys Val Thr
 1               5                  10                  15

<210> SEQ ID NO 48
<211> LENGTH: 16
<212> TYPE: PRT
<213> ORGANISM: Homo sapiens

<400> SEQUENCE: 48

Met Met Lys Asp Gln Tyr Ala Asn Tyr Val Val Gln Lys Met Ile Asp
 1               5                  10                  15
```

The invention claimed is:

1. A method of identifying an agent that alters the lifespan of a eukaryotic cell, the method comprising:
   a) providing a eukaryotic cell characterized by a first replicative capacity;
   b) contacting the eukaryotic cell with an agent to provide a treated eukaryotic cell, wherein the agent is a drug;
   c) evaluating a phenotype of the treated eukaryotic cell, in the presence of the agent, wherein the phenotype is stress survival; and
   d) evaluating replicative capacity of the treated eukaryotic cell in the presence of the agent, wherein modulation of the phenotype and replicative capacity, relative to a corresponding phenotype and capacity of a eukaryotic cell not contacted with the agent, identifies the agent as an agent that alters the lifespan of a eukaryotic cell.

2. The method of claim 1 wherein the phenotype is a function of growth to higher saturation density than the cells provided in (a).

3. The method of claim 1 wherein the phenotype is heat shock resistance.

4. The method of claim 1 wherein the phenotype is starvation resistance.

5. The method of claim 1 wherein the phenotype is paraquat resistance.

6. The method of claim 1 wherein the phenotype is caffeine resistance.

7. The method of claim 1 wherein the eukaryotic cell is a yeast cell.

8. The method of claim 1 wherein the eukaryotic cell is a genetically-altered eukaryotic cell which has a different replicative capacity relative to a reference eukaryotic cell.

9. The method of claim 1 wherein the step d) of evaluating comprises: (i) calculating the number of divisions of the treated eukaryotic cell, and (ii) comparing the number of divisions in (i) with the average number of divisions for the eukaryotic cell in the absence of the agent to be tested.

10. A method of identifying an agent that alters the lifespan of a eukaryotic cell, the method comprising:
    a) providing a eukaryotic cell characterized by a first replicative capacity;
    b) contacting the eukaryotic cell with an agent to provide a treated eukaryotic cell, wherein the agent is a peptide;
    c) evaluating a phenotype of the treated eukaryotic cell, in the presence of the agent, wherein the phenotype is stress survival; and
    d) evaluating replicative capacity of the treated eukaryotic cell in the presence of the agent, wherein modulation of the phenotype and replicative capacity, relative to a corresponding phenotype and capacity of a eukaryotic cell not contacted with the agent, identifies the agent as an agent that alters the lifespan of a eukaryotic cell.

11. The method of claim 10 wherein the phenotype is a function of growth to higher saturation density than the cells provided in (a).

12. The method of claim 10 wherein the phenotype is heat shock resistance.

13. The method of claim 10 wherein the phenotype is starvation resistance.

14. The method of claim 10 wherein the phenotype is paraquat resistance.

15. The method of claim 10 wherein the phenotype is caffeine resistance.

16. The method of claim 10 wherein the eukaryotic cell is a yeast cell.

17. The method of claim 10 wherein the eukaryotic cell is a genetically-altered eukaryotic cell which has a different replicative capacity relative to a reference eukaryotic cell.

18. The method of claim 10 wherein the step d) of evaluating comprises: (i) calculating the number of divisions of the treated eukaryotic cell, and (ii) comparing the number of divisions in (i) with the average number of divisions for the eukaryotic cell in the absence of the agent to be tested.

19. A method of identifying an agent that alters the lifespan of a eukaryotic cell, the method comprising:
    a) providing a eukaryotic cell characterized by a first replicative capacity;
    b) contacting the eukaryotic cell with an agent to provide a treated eukaryotic cell, wherein the agent is an oligonucleotide;
    c) evaluating a phenotype of the treated eukaryotic cell, in the presence of the agent, wherein the phenotype is stress survival; and
    d) evaluating replicative capacity of the treated eukaryotic cell in the presence of the agent, wherein modulation of the phenotype and replicative capacity, relative to a corresponding phenotype and capacity of a eukaryotic cell not contacted with the agent, identifies the agent as an agent that alters the lifespan of a eukaryotic cell.

20. The method of claim 19 wherein the phenotype is a function of growth to higher saturation density than the cells provided in (a).

21. The method of claim 19 wherein the phenotype is heat shock resistance.

22. The method of claim 19 wherein the phenotype is starvation resistance.

23. The method of claim 19 wherein the phenotype is paraquat resistance.

24. The method of claim 19 wherein the phenotype is caffeine resistance.

25. The method of claim 19 wherein the eukaryotic cell is a yeast cell.

26. The method of claim 19 wherein the eukaryotic cell is a genetically-altered eukaryotic cell which has a different replicative capacity relative to a reference eukaryotic cell.

27. The method of claim 19 wherein the step d) of evaluating comprises: (i) calculating the number of divisions of the treated eukaryotic cell, and (ii) comparing the number of divisions in (i) with the average number of divisions for the eukaryotic cell in the absence of the agent to be tested.

28. A method of identifying an agent that alters the lifespan of a eukaryotic cell, the method comprising:
    a) providing a eukaryotic cell characterized by a first replicative capacity;
    b) contacting the eukaryotic cell with an agent to provide a treated eukaryotic cell, wherein the agent is other than a gene;
    c) evaluating a phenotype of the treated eukaryotic cell, in the presence of the agent, wherein the phenotype is stress survival; and
    d) evaluating replicative capacity of the treated eukaryotic cell in the presence of the agent, wherein modulation of the phenotype and replicative capacity, relative to a corresponding phenotype and capacity of a eukaryotic cell not contacted with the agent, identifies the agent as an agent that alters the lifespan of a eukaryotic cell.

29. The method of claim 28 wherein the phenotype is a function of growth to higher saturation density than the cells provided in (a).

30. The method of claim 23 wherein the phenotype is heat shock resistance.

31. The method of claim 28 wherein the phenotype is starvation resistance.

32. The method of claim 28 wherein the phenotype is paraquat resistance.

33. The method of claim 28 wherein the phenotype is caffeine resistance.

34. The method of claim 28 wherein the eukaryotic cell is a yeast cell.

35. The method of claim 28 wherein the eukaryotic cell is a genetically-altered eukaryotic cell which has a different replicative capacity relative to a reference eukaryotic cell.

36. The method of claim 28 wherein the step d) of evaluating comprises: (i) calculating the number of divisions of the treated eukaryotic cell, and (ii) comparing the number of divisions in (i) with the average number of divisions for the eukaryotic cell in the absence of the agent to be tested.

37. The method of claims 8, 17, 26, or 35 wherein the genetically altered eukaryotic cell comprises a mutation in a chromosomal gene.

38. The method of claim 37 wherein the step d) of evaluating comprises: (i) calculating the number of divisions of the treated eukaryotic cell, and (ii) comparing the number of divisions in (i) with the average number of divisions for the eukaryotic cell in the absence of the agent to be tested.

39. The method of claims 1, 10, 19, or 28 wherein the treated eukaryotic cell is labeled on the cell surface, and the step c) of evaluating comprises detecting the labeled, treated eukaryotic cell.

40. The method of claim 39 wherein the treated eukaryotic cell is fluorescently labeled.

41. The method of claims 1, 10, 19, or 28 wherein the treated eukaryotic cell is cultured for a period of time greater than time sufficient for the first replicative capacity.

42. The method of claims 4, 13, 22, or 31 wherein the step c) of evaluating comprises maintaining the treated eukaryotic cell under starvation conditions.

43. The method of claims 7, 16, 25, or 34 wherein the phenotype is heat shock resistance.

44. The method of claims 7, 16, 25, or 34 wherein the phenotype is starvation resistance.

45. The method of claims 8, 17, 26, 35, 9, 18, 27, or 36 wherein the phenotype is heat shock resistance.

46. The method of claims 8, 17, 26, 35, 9, 18, 27, or 36 wherein the phenotype is starvation resistance.

47. The method of claims 8, 17, 26, 35, 9, 18, 27, or 36 wherein the phenotype is paraquat resistance.

48. The method of claims 8, 17, 26, 35, 9, 18, 27, or 36 wherein the phenotype is caffeine resistance.

* * * * *

UNITED STATES PATENT AND TRADEMARK OFFICE
CERTIFICATE OF CORRECTION

PATENT NO. : 6,787,300 B2 Page 1 of 1
DATED : September 7, 2004
INVENTOR(S) : Leonard P. Guarente, Nicanor Austriaco, Jr. and Brian Kennedy It is certified that error appears in the above-identified patent and that said Letters Patent is hereby corrected as shown below:

Title page,
Item [56], References Cited, OTHER PUBLICATIONS, "Cristofalo et al." reference, delete ":367-374" and replace with -- 24:367-374 --.

Column 94,
Line 62, delete "of claim 23" and replace with -- of claim 28 --.

Signed and Sealed this

Twenty-second Day of November, 2005

JON W. DUDAS
*Director of the United States Patent and Trademark Office*